US009409865B2

(12) United States Patent
Albrecht et al.

(10) Patent No.: US 9,409,865 B2
(45) Date of Patent: Aug. 9, 2016

(54) MODULATORS OF METHYL MODIFYING ENZYMES, COMPOSITIONS AND USES THEREOF

(71) Applicant: Constellation Pharmaceuticals, Inc., Cambridge, MA (US)

(72) Inventors: Brian K. Albrecht, Cambridge, MA (US); James Edmund Audia, Chicago, IL (US); Alexandre Gagnon, Beaconsfield (CA); Jean-Christophe Harmange, Andover, MA (US); Christopher G. Nasveschuk, Stoneham, MA (US)

(73) Assignee: Constellation Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/707,874

(22) Filed: May 8, 2015

(65) Prior Publication Data
US 2015/0315148 A1 Nov. 5, 2015

Related U.S. Application Data

(62) Division of application No. 14/358,455, filed as application No. PCT/US2012/065797 on Nov. 19, 2012, now Pat. No. 9,051,269.

(60) Provisional application No. 61/593,807, filed on Feb. 1, 2012, provisional application No. 61/561,823, filed on Nov. 18, 2011.

(51) Int. Cl.
| | |
|---|---|
| *C07D 213/62* | (2006.01) |
| *C07D 213/64* | (2006.01) |
| *C07D 213/81* | (2006.01) |
| *C07D 405/12* | (2006.01) |
| *C07D 401/12* | (2006.01) |

(52) U.S. Cl.
CPC ............ *C07D 213/64* (2013.01); *C07D 213/81* (2013.01); *C07D 401/12* (2013.01); *C07D 405/12* (2013.01)

(58) Field of Classification Search
CPC .................................................... C07D 213/64
USPC ........................................................ 546/261
See application file for complete search history.

(56) References Cited

U.S. PATENT DOCUMENTS

| | | | |
|---|---|---|---|
| 4,738,971 A | 4/1988 | Eriksoo et al. | |
| 5,308,854 A | 5/1994 | Hoffman, Jr. et al. | |
| 7,838,520 B2 | 11/2010 | Delorme et al. | |
| 8,410,088 B2 | 4/2013 | Kuntz et al. | |
| 9,206,128 B2 * | 12/2015 | Albrecht | C07D 221/18 |
| 2003/0207875 A1 | 11/2003 | Gymer et al. | |
| 2003/0229081 A1 | 12/2003 | Maduskuie | |
| 2005/0266473 A1 | 12/2005 | Zhang et al. | |
| 2006/0035938 A1 | 2/2006 | Bladh et al. | |
| 2007/0155744 A1 | 7/2007 | Jones et al. | |
| 2008/0027050 A1 | 1/2008 | Terauchi et al. | |
| 2008/0227826 A1 | 9/2008 | Frechette et al. | |
| 2008/0280917 A1 | 11/2008 | Albrecht et al. | |
| 2009/0029991 A1 | 1/2009 | Stokes et al. | |
| 2009/0075833 A1 | 3/2009 | Chinnaiyan et al. | |
| 2010/0069630 A1 | 3/2010 | Lee et al. | |
| 2010/0222420 A1 | 9/2010 | Chinnaiyan et al. | |
| 2010/0261743 A1 | 10/2010 | Londregan et al. | |
| 2010/0298270 A1 | 11/2010 | Keana et al. | |
| 2011/0105509 A1 | 5/2011 | Kaila et al. | |
| 2011/0212946 A1 | 9/2011 | Barrow et al. | |
| 2012/0071418 A1 | 3/2012 | Copeland et al. | |
| 2013/0040906 A1 | 2/2013 | Kuntz et al. | |
| 2013/0230511 A1 | 9/2013 | Heymach et al. | |
| 2014/0107122 A1 | 4/2014 | Kuntz et al. | |

FOREIGN PATENT DOCUMENTS

| | | |
|---|---|---|
| WO | 03/020722 A1 | 3/2003 |
| WO | 03/079986 A2 | 10/2003 |
| WO | 2007/014838 A1 | 2/2007 |
| WO | 2009/087285 A1 | 7/2009 |
| WO | 2009/153721 A1 | 12/2009 |
| WO | 2011/131741 A1 | 10/2011 |
| WO | 2011/140324 A1 | 11/2011 |
| WO | 2011/140325 A1 | 11/2011 |
| WO | 2012/005805 A1 | 1/2012 |
| WO | 2012/068589 A2 | 5/2012 |
| WO | 2012/075080 A1 | 6/2012 |
| WO | 2013/039988 A1 | 3/2013 |
| WO | 2013/049770 A2 | 4/2013 |
| WO | 2013/067296 A1 | 5/2013 |
| WO | 2013/067300 A1 | 5/2013 |
| WO | 2013/067302 A1 | 5/2013 |
| WO | 2013/075083 A1 | 5/2013 |

(Continued)

OTHER PUBLICATIONS

Knutson, et al., "A Selective Inhibitor of EZH2 Blocks H3K27 Methylation and Kills Mutant Lymphoma Cells," Nature Chemical Biology, 8(11), 2012, 890-896.

McCabe, et al., "EZH2 Inhibition as a Therapeutic Strategy for Lymphoma with EZH2-Activating Mutations," Nature, 492(7427), 2012, 108-112.

Qi, et al., "Selective Inhibition of Ezh2 by a Small Molecule Inhibitor Blocks Tumor Cells Proliferation," Proceedings of the National Academy of Sciences of the United States of America, 109(52), 2012, 21360-21365.

Spannhoff, et al., "The Emerging Therapeutic Potential of Histone Methyltransferase and Demethylase Inhibitors," Chem Med Chem, 2009, 4:1568-1582.

Verma, et al., "Identification of Potent, Selective, Cell-Active Inhibitors of the Histone Lysine Methyltransferase EZH2," ACS Medicinal Chemistry Letters, 3(12), 2012, 1091-1096.

*Primary Examiner* — Nizal Chandrakumar
(74) *Attorney, Agent, or Firm* — McCarter & English, LLP; Steven G. Davis; Michael J. DeGrazia

(57) ABSTRACT

Agents for modulating methyl modifying enzymes, compositions and uses thereof are provided herein.

3 Claims, No Drawings

(56) References Cited

FOREIGN PATENT DOCUMENTS

| WO | 2013/075084 | A1 | 5/2013 |
| WO | 2013/120104 | A2 | 8/2013 |
| WO | 2013/138361 | A1 | 9/2013 |
| WO | 2013/155317 | A1 | 10/2013 |
| WO | 2013/155464 | A1 | 10/2013 |
| WO | 2013/173441 | A2 | 11/2013 |
| WO | 2014/049488 | A1 | 4/2014 |
| WO | 2014/062720 | A2 | 4/2014 |

* cited by examiner

MODULATORS OF METHYL MODIFYING ENZYMES, COMPOSITIONS AND USES THEREOF

CROSS-REFERENCE TO RELATED APPLICATIONS

This application is divisional of U.S. application Ser. No. 14/358,455, filed May 15, 2014, which is a 35 U.S.C. §371 National Stage filing of International Application No. PCT/US2012/065797, filed Nov. 19, 2012, which claims the benefit of U.S. Provisional Ser. Nos. 61/561,823, filed Nov. 18, 2011, and 61/593,807, filed Feb. 1, 2012. The entire contents of each of the aforementioned applications are incorporated herein by reference.

BACKGROUND OF THE INVENTION

Eukaryotic chromatin is composed of macromolecular complexes called nucleosomes. A nucleosome has 147 base pairs of DNA wrapped around a protein octamer having two subunits of each of histone protein H2A, H2B, H3, and H4. Histone proteins are subject to post-translational modifications which in turn affect chromatin structure and gene expression. One type of post-translational modification found on histones is methylation of lysine and arginine residues. Histone methylation plays a critical role in the regulation of gene expression in eukaryotes. Methylation affects chromatin structure and has been linked to both activation and repression of transcription (Zhang and Reinberg, Genes Dev. 15:2343-2360, 2001). Enzymes that catalyze attachment and removal of methyl groups from histones are implicated in gene silencing, embryonic development, cell proliferation, and other processes.

SUMMARY OF THE INVENTION

The present disclosure encompasses the recognition that methyl modifying enzymes are an attractive target for modulation, given their role in the regulation of diverse biological processes. It has now been found that compounds of this invention, and pharmaceutically acceptable compositions thereof, are effective as agents that stimulate activity of histone methyl modifying enzymes, including histone methylases and histone demethylases. Such compounds have the general formula I:

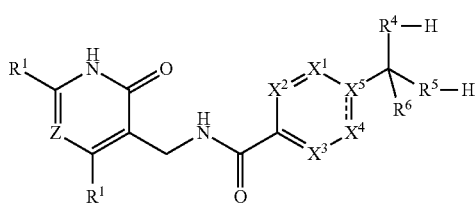

or a pharmaceutically acceptable salt thereof, wherein each variable is as defined herein.

Compounds of the present invention, and pharmaceutically acceptable compositions thereof, are useful for treating a variety of diseases, disorders or conditions, associated with a methyl modifying enzyme. Such diseases, disorders, or conditions include those described herein.

Compounds provided by this invention are also useful for the study of methyl modifying enzymes in biological and pathological phenomena; the study of intracellular signal transduction pathways mediated by methyl modifying enzymes and the comparative evaluation of new methyl modifying enzyme modulators.

DETAILED DESCRIPTION OF CERTAIN EMBODIMENTS

I. General Description of Compounds of the Invention

In certain embodiments, the present invention provides a compound of formula I:

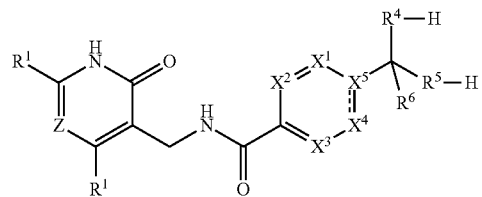

or a pharmaceutically acceptable salt thereof, wherein:

$Z$ is $=C(R^2)-$ or $=N-$;

each of $X^1$, $X^2$ and $X^3$ is independently selected from $=N-$ and $=C(R^3)-$;

$X^4$ is selected from $=N-$, $-C(=O)-$ and $=C(R^3)-$;

$X^5$ is $=C-$ or

no more than two of $X^1$, $X^2$, $X^3$, $X^4$, and $X^5$ are $=N-$ or

each $R^1$ and $R^2$ is independently selected from hydrogen, halo, $-OH$, $-CN$, $C_1$-$C_4$ alkyl, $-O-(C_1$-$C_4$ alkyl), $N(R^7)_2$, $-(C_0$-$C_4$ alkylene)-aryl, $-(C_0$-$C_4$ alkylene)-heteroaryl, $-(C_0$-$C_4$ alkylene)-heterocyclyl, $-(C_0$-$C_4$ alkylene)-carbocyclyl, $-O-(C_0$-$C_4$ alkylene)-aryl, $-O-(C_0$-$C_4$ alkylene)-heteroaryl, $-O-(C_0$-$C_4$ alkylene)-heterocyclyl, $-O-(C_0$-$C_4$ alkylene)-carbocyclyl; or one $R^1$ and $R^2$ are taken together with atoms to which they are bound to form an aryl, heteroaryl, heterocyclyl, or carbocyclyl;

each $R^3$ is independently selected from hydrogen, halo, $-OH$, $-CN$, $C_1$-$C_4$ alkyl, $C_2$-$C_4$ alkenyl or alkynyl, $-O-(C_1$-$C_4$ alkyl), $N(R^7)_2$, $-(C_0$-$C_4$ alkylene)-aryl, $-(C_0$-$C_4$ alkylene)-heteroaryl, $-(C_0$-$C_4$ alkylene)-heterocyclyl, $-(C_0$-$C_4$ alkylene)-carbocyclyl, $-O-(C_0$-$C_4$ alkylene)-aryl, $-O-(C_0$-$C_4$ alkylene)-heteroaryl, $-O-(C_0$-$C_4$ alkylene)-heterocyclyl, $-O-(C_0$-$C_4$ alkylene)-carbocyclyl, $-C(O)OR^9$, $-C(O)N(R^9)_2$, $-S(O)R^8$, $-S(O)_2R^8$ and $-S(O)_2N(R^9)_2$;

$R^4$ is a $C_0$-$C_6$ straight or branched, alkylene chain, or a $C_2$-$C_6$ straight or branched alkenylene or alkynylene chain, wherein each methylene unit in $R^4$ is substituted with two $R^a$;

each $=CH-$ unit is substituted with $R^a$; and one or two methylene units of $R^4$ are optionally and independently replaced by —O—, —S—, —S(=O)—, —S(=O)$_2$—, or —N($R^{10}$)—, with the proviso that the terminal methylene unit bound to hydrogen is not replaced with —S—, —S(=O)—, or —S(=O)$_2$—;

each $R^a$ is independently selected from hydrogen, $C_1$-$C_4$ alkyl, halo, —N($R^{10}$)$_2$, —OH, —O—($C_1$-$C_4$ alkyl), or —CN; or two $R^a$ bound to the same carbon atom are taken together to form =O, monocyclic carbocyclyl or a monocyclic heterocyclyl;

$R^5$ is a $C_1$-$C_6$ straight or branched alkylene chain, or a $C_2$-$C_6$ straight or branched alkenylene or alkynylene chain, wherein each methylene unit in $R^5$ is substituted with two $R^a$, each =CH-unit is substituted with $R^a$; and one or two methylene units of $R^5$ are optionally and independently replaced by —O—, —S—, —S(=O)—, —S(=O)$_2$—, or —N$R^{10}$—, with the proviso that the terminal methylene unit bound to hydrogen is not replaced with —S—, —S(=O)—, or —S(=O)$_2$—; or one methylene unit of $R^5$ is taken together with X or $X^4$, when the $X^1$ or $X^4$ is =C($R^3$)—, and the intervening atoms to form an optionally substituted aryl, heteroaryl, heterocyclyl or carbocyclyl fused to the ring comprising $X^1$, $X^2$, $X^3$, $X^4$ and $X^5$;

$R^6$ is hydrogen or methyl;

each $R^7$ is independently selected from hydrogen, —($C_0$-$C_4$ alkylene)-$R^9$, —($C_2$-$C_4$ alkylene)-O—$R^9$, $C_2$-$C_4$ haloalkyl, —S(O)$_2$—$R^8$, —C(=O)—$R^8$, —C(=O)—N($R^9$)($R^9$), —($C_2$-$C_4$ alkylene)-O—C(=O)—$R^8$ and —($C_0$-$C_4$ alkylene)-C(=O)—O—$R^9$; or two $R^7$ are taken together with the nitrogen atom to which they are commonly bound to form an optionally substituted heterocyclyl or heteroaryl;

$R^8$ is selected from $C_1$-$C_4$ alkyl, aryl, heteroaryl, carbocyclyl and heterocyclyl;

each $R^9$ is independently selected from hydrogen or $R^8$;

each $R^{10}$ is independently selected from hydrogen, $C_1$-$C_4$ alkyl, $C_2$-$C_4$ haloalkyl, —S(=O)$_2$—$R^{11}$, —C(=O)—$R^{11}$, —C(=O)—N($R^{11}$)($R^{12}$), and —C(=O)—O—$R^{11}$;

$R^{11}$ is $C_1$-$C_4$ alkyl;

$R^{12}$ is selected from hydrogen, and $C_1$-$C_4$ alkyl;

≡≡≡ represents a single or double bond;

wherein unless otherwise designated any alkyl, alkylene, alkenyl, alkenylene, alkynyl, alkynylene, aryl, heteroaryl, heterocyclyl or carbocyclyl portion of the compound is optionally substituted.

2. Compounds and Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

As used herein a "direct bond" or "covalent bond" refers to a single, double or triple bond. In certain embodiments, a "direct bond" or "covalent bond" refers to a single bond.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —($CH_2$)—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "alkynylene" refers to a bivalent alkynyl group.

The term "methylene unit" refers to a divalent —$CH_2$— group present in an alkyl, alkenyl, alkynyl, alkylene, alkenylene, or alkynylene moiety.

The term "$C_0$ alkylene" as used herein means a bond. Thus, a moiety defined herein as "—($C_0$-$C_6$ alkylene)-aryl" includes both -aryl (i.e., $C_0$ alkylene-aryl) and —($C_1$-$C_6$ alkylene)-aryl.

The term "alkyl," as used herein, refers to a monovalent saturated, straight- or branched-chain hydrocarbon radical derived from an aliphatic moiety containing between one and six carbon atoms by removal of a single hydrogen atom. In some embodiments, alkyl contains 1-5 carbon atoms. In another embodiment, alkyl contains 1-4 carbon atoms. In still other embodiments, alkyl contains 1-3 carbon atoms. In yet another embodiment, alkyl contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, and the like.

The term "alkenyl," as used herein, denotes a monovalent group derived from a straight- or branched-chain aliphatic moiety having at least one carbon-carbon double bond by the removal of a single hydrogen atom. In certain embodiments, alkenyl contains 2-6 carbon atoms. In certain embodiments, alkenyl contains 2-5 carbon atoms. In some embodiments, alkenyl contains 2-4 carbon atoms. In another embodiment, alkenyl contains 2-3 carbon atoms. Alkenyl groups include, for example, ethenyl ("vinyl"), propenyl ("allyl"), butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. In certain embodiments, alkynyl contains 2-6 carbon atoms. In certain embodiments, alkynyl contains 2-5 carbon atoms. In some embodiments, alkynyl contains 2-4 carbon atoms. In another embodiment, alkynyl contains 2-3 carbon atoms. Representative alkynyl groups include, but are not limited to, ethynyl, 2-propynyl ("propargyl"), 1-propynyl, and the like.

The term "carbocyclyl" (also referred to herein as "carbocycle" "cycloaliphatic" or "cycloalkyl"), as used herein, means a monocyclic hydrocarbon or bicyclic hydrocarbon that is completely saturated or that contains one or more units of unsaturation, but where there is no ring aromatic.

The term "aryl" used alone or as part of a larger moiety as in "aralkyl", "aralkoxy", or "aryloxyalkyl", refers to monocyclic and bicyclic carbon ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic carbon ring is fused to one or more carbocyclyl rings regardless of whether the aromatic carbon ring or the carbocyclic ring is the pendant ring, or a group in which an aromatic carbon ring is fused to one or more heteroaryl or heterocyclyl rings, such as indanyl, phthalimidyl, naphthimidyl, phenantriidinyl, or tetrahydronaphthyl, and the like, wherein the pendant ring of the fused ring system is the aromatic carbon ring.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, wherein the pendant ring of the fused ring system is heteroaromatic. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, 5,6,7,8-tetrahydroquinolinyl, 5,6,7,8-tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. The term "heteroarylene" refers to a bivalent mono- or bicyclic heteroaryl ring.

As used herein, the terms "heterocycle", "heterocyclyl", "heterocyclic radical", and "heterocyclic ring" are used interchangeably and refer to a stable 4- to 7-membered monocyclic or 7-10-membered bicyclic heterocyclic moiety that is either saturated or partially unsaturated, and having, in addition to carbon atoms, one or more, preferably one to four, heteroatoms, as defined above. In certain embodiments, a "heterocycle", group is a 1,1'-heterocyclylene group (i.e., a spiro-fused ring). When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, 1,2,3,4-tetrahydroquinolinyl, 1,2,3,4-tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, 2-azabicyclo[2.2.1]heptanyl, octahydroindolyl, or tetrahydroquinolinyl, wherein the pendant ring of the fused ring system is heterocyclyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms but is not aromatic. The term "partially unsaturated" is intended to encompass rings having multiple sites of unsaturation, but is not intended to include aryl or heteroaryl moieties, as herein defined.

As used herein, the terms "carbocyclylene" or "cycloalkylene" are used interchangeably and refer to a bivalent carbocyclyl or cycloalkyl group. In certain embodiments, a carbocyclylene or cycloalkylene group is a 1,1-cycloalkylene group (i.e., a spiro-fused ring). Exemplary 1,1-cycloalkylene groups include

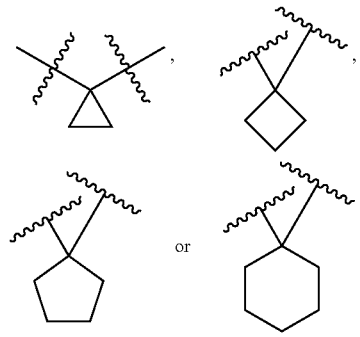

In other embodiments, a cycloalkylene group is a 1,2-cycloalkylene group or a 1,3-cycloalkylene group. Exemplary 1,2-cycloalkylene groups include

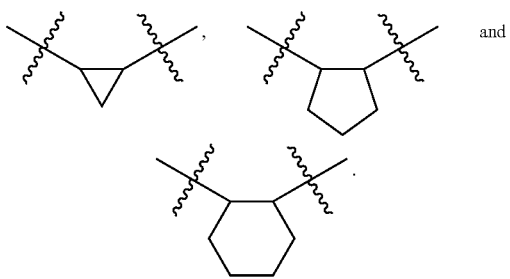

Exemplary 1,3-cycloalkylene groups include

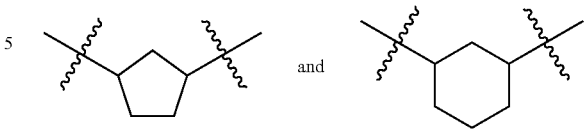

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O-(CH_2)_{0-4}C(O)OR^\circ$; $-(CH_2)_{0-4}CH(OR^\circ)_2$; $-(CH)_{0-4}SR^\circ$; $-(CH_2)_{0-4}$Ph, which may be substituted with $R^\circ$; $-(CH_2)_{0-4}O(CH_2)_{0-1}$Ph which may be substituted with $R^\circ$; $-CH=CHPh$, which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $-SiR^\circ_3$; $-(C_{1-4}$ straight or branched)alkylene)O$-N(R^\circ)_2$; or $-(C_{1-4}$ straight or branched)alkylene)C(O)O$-N(R^\circ)_2$, wherein each $R^\circ$ may be substituted as defined below and is independently hydrogen, $C_{1-6}$ aliphatic, $-CH_2$Ph, $-O(CH_2)_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$) $(CH_2)_{0-2}$OH, $-(CH_2)_{0-2}OR^\bullet$, $-(CH_2)_{0-2}CH(OR^\bullet)_2$; $-O$(haloR$^\bullet$), $-CN$, $-N_3$, —(CH$_2$)$_{0-2}$C(O)R•, —(CH$_2$)$_{0-2}$C(O)OH, —(CH$_2$)$_{0-2}$C(O)OR•, —(CH$_2$)$_{0-2}$SR•, —(CH$_2$)$_{0-2}$SH, —(CH$_2$)$_{0-2}$NH$_2$, —(CH$_2$)$_{0-2}$NHR•, —(CH$_2$)$_{0-2}$NR•$_2$, —NO$_2$, —OSiR•$_3$, —C(O)SR•, —(C$_{1-4}$ straight or branched alkylene)C(O)OR•, or —SSR• wherein each R• is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include-R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "inhibitor" is defined as a compound that binds to and/or inhibits a target S-adenosylmethionine (SAM) utilizing enzyme with measurable affinity. In certain embodiments, an inhibitor has an IC$_{50}$ and/or binding constant of less about 50 µM, less than about 1 µM, less than about 500 nM, less than about 100 nM, or less than about 10 nM.

The terms "measurable affinity" and "measurably inhibit," as used herein, means a measurable change in activity of at least one SAM utilizing enzyme between a sample comprising a provided compound, or composition thereof, and at least one SAM dependent enzyme, and an equivalent sample comprising at least one SAM dependent enzyme, in the absence of said compound, or composition thereof.

3. Description of Exemplary Compounds

In certain embodiments, the present invention provides a compound of formula I:

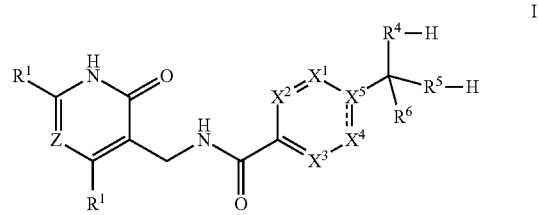

or a pharmaceutically acceptable salt thereof, wherein each variable is as defined above and described herein.

As defined generally above and herein, each R$^1$ and R$^2$ is independently selected from hydrogen, halo, —OH, —CN, C$_1$-C$_4$ alkyl, —O—(C$_1$-C$_4$ alkyl), N(R$^7$)$_2$, —(C$_0$-C$_4$ alkylene)-aryl, —(C$_0$-C$_4$ alkylene)-heteroaryl, —(C$_0$-C$_4$ alkylene)-heterocyclyl, —(C$_0$-C$_4$ alkylene)-carbocyclyl, —O—(C$_0$-C$_4$ alkylene)-aryl, —O—(C$_0$-C$_4$ alkylene)-heteroaryl, —O—(C$_0$-C$_4$ alkylene)-heterocyclyl, or —O—(C$_0$-C$_4$ alkylene)-carbocyclyl; or one R$^1$ and R$^2$ are taken together with atoms to which they are bound to form an aryl, heteroaryl, heterocyclyl, or carbocyclyl;

wherein each R$^7$ is as defined above and described herein.

In one embodiment, each R$^1$ and R$^2$ is independently selected from hydrogen, halo, —OH, —CN, C$_1$-C$_4$ alkyl, C$_1$-C$_4$ haloalkyl, —O—(C$_1$-C$_4$ alkyl), N(R$^7$)$_2$, —(C$_0$-C$_4$ alkylene)-aryl, —(C$_0$-C$_4$ alkylene)-heteroaryl, —(C$_0$-C$_4$ alkylene)-heterocyclyl, or —(C$_0$-C$_4$ alkylene)-carbocyclyl; or one R$^1$ and R$^2$ are taken together with atoms to which they are bound to form an aryl, heteroaryl, heterocyclyl, or carbocyclyl;

wherein each R$^7$ is as defined above and described herein.

In some embodiments, each R$^1$ is hydrogen. In some embodiments, each R$^1$ and R$^2$ is independently selected from halo, —OH, —CN, C$_1$-C$_4$ alkyl, —O—(C$_1$-C$_4$ alkyl), N(R$^7$)$_2$, —(C$_0$-C$_4$ alkylene)-aryl, —(C$_0$-C$_4$ alkylene)-heteroaryl, —(C$_0$-C$_4$ alkylene)-heterocyclyl, —(C$_0$-C$_4$ alkylene)-carbocyclyl, —O—(C$_0$-C$_4$ alkylene)-aryl, —O—(C$_0$-C$_4$ alkylene)-heteroaryl, —O—(C$_0$-C$_4$ alkylene)-heterocyclyl, or —O—(C$_0$-C$_4$ alkylene)-carbocyclyl, wherein each R$^7$ is as defined above and described herein. In some embodiments, each R$^1$ is independently selected from halo, —OH, —CN, C$_1$-C$_4$ alkyl, C$_1$-C$_4$ haloalkyl, —O(C$_1$-C$_4$ alkyl), N(R$^7$)$_2$, —(C$_0$-C$_4$ alkylene)-aryl, —(C$_0$-C$_4$ alkylene)-heteroaryl, —(C$_0$-C$_4$ alkylene)-heterocyclyl, or —(C$_0$-C$_4$ alkylene)-carbocyclyl, wherein each R$^7$ is as defined above and described herein. In some embodiments, one R$^1$ and R$^2$ are taken together with atoms to which they are bound to form an aryl, heteroaryl, heterocyclyl, or carbocyclyl.

In some embodiments, each $R^1$ is independently selected from hydrogen and —$CH_3$. In some embodiments, each $R^1$ is hydrogen. In some embodiments, each $R^1$ is —$CH_3$. In some embodiments, one $R^1$ is hydrogen. In some embodiments, one $R^1$ is —$CH_3$. In some embodiments, one $R^1$ is —$CH_3$ and the other $R^1$ is selected from —O—$CH_3$ and —NH—$CH_3$ In some embodiments, each of $R^1$ and $R^2$ is hydrogen. In some embodiments, each $R^1$ is —$CH_3$ and $R^2$ is hydrogen. In some embodiments, one $R^1$ is —$CH_3$; the other $R^1$ is —O—$CH_3$ or —NH—$CH_3$; and $R^2$ is hydrogen.

In some embodiments, each $R^2$ is hydrogen.

As defined generally above and herein, Z is =$C(R^2)$— or =N—, wherein $R^2$ is as defined above and described herein. In some embodiments, Z is =$C(R^2)$— wherein $R^2$ is as defined above and described herein. In some embodiments, Z is =N—. In some embodiments, Z is =CH—.

As defined generally above and herein, each $R^3$ is independently selected from hydrogen, halo, —OH, —CN, $C_1$-$C_4$ alkyl, $C_2$-$C_4$ alkenyl or alkynyl, —O—($C_1$-$C_4$ alkyl), $N(R^7)_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, —O—($C_0$-$C_4$ alkylene)-carbocyclyl, —$C(O)OR^9$, —$C(O)N(R^9)_2$, —$S(O)R^8$, —$S(O)_2R^8$ and —$S(O)_2N(R^9)_2$, wherein each of $R^7$, $R^8$ and $R^9$ is independently as defined above and described herein.

In some embodiments, each $R^3$ is independently selected from hydrogen, halo, —OH, —CN, $C_1$-$C_4$ alkyl, $C_1$-$C_4$ haloalkyl, —O—($C_1$-$C_4$ alkyl), $N(R^7)_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl, wherein each $R^7$ is independently as defined above and described herein.

In some embodiments, each $R^3$ is hydrogen.

In some embodiments, each $R^3$ is independently selected from halo, —OH, —CN, $C_1$-$C_4$ alkyl, $C_2$-$C_4$ alkenyl or alkynyl, —O—($C_1$-$C_4$ alkyl), $N(R^7)_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, —O—($C_0$-$C_4$ alkylene)-carbocyclyl, —$C(O)OR^9$, —$C(O)N(R^9)_2$, —$S(O)R^8$, —$S(O)_2R^8$ and —$S(O)_2N(R^9)_2$, wherein each of $R^7$, $R^8$ and $R^9$ is independently as defined above and described herein. In some embodiments, each $R^3$ is independently selected from halo, —OH, —CN, $C_1$-$C_4$ alkyl, $C_1$-$C_4$ haloalkyl, —O—($C_1$-$C_4$ alkyl), $N(R^7)_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl, wherein each $R^7$ is as defined above and described herein. In some embodiments, each $R^3$ is independently selected from hydrogen, halo, $C_1$-$C_4$ alkyl and —O-phenyl. In some embodiments, each $R^3$ is independently selected from hydrogen, chloro, —$CH_3$ and —O-phenyl.

As defined generally above and herein, each of $X^1$, $X^2$ and $X^3$ is independently selected from =N— and =$C(R^3)$—, wherein $R^3$ is as defined above and described herein. In some embodiments, each of $X^1$, $X^2$ and $X^3$ is independently =N—. In some embodiments, each of $X^1$, $X^2$ and $X^3$ is independently =$C(R^3)$—, wherein $R^3$ is as defined above and described herein.

As defined generally above and herein, $X^4$ is selected from =N—, —$C(=O)$— and =$C(R^3)$—, wherein $R^3$ is as defined above and described herein. In some embodiments, $X^4$ is =N—. In some embodiments, $X^4$ is —$C(=O)$—. In some embodiments, $X^4$ is =$C(R^3)$—, wherein $R^3$ is as defined above and described herein.

As defined generally above and herein, $X^5$ is =C— or

In some embodiments, $X^5$ is =C—. In some embodiments, $X^5$ is

In some embodiments, each of $X^1$, $X^2$, $X^3$ and $X^4$ is =$C(R^3)$—, and $X^5$ is =C—, wherein $R^3$ is as defined above and described herein.

In some embodiments, each of $X^1$, $X^2$, $X^3$ and $X^4$ is =CH—, and $X^5$ is =C—.

As defined generally above and herein, no more than two of $X^1$, $X^2$, $X^3$, $X^4$, and $X^5$ are =N— or

As defined generally above and herein, $R^4$ is a $C_0$-$C_6$ straight or branched, alkylene chain, or a $C_2$-$C_6$ straight or branched alkenylene or alkynylene chain, wherein
  each methylene unit in $R^4$ is substituted with two $R^a$;
  each =CH— unit is substituted with $R^a$; and
  one or two methylene units of $R^4$ are optionally and independently replaced by —O—, —S—, —$S(=O)$—, —$S(=O)_2$—, or —$N(R^{10})$—, with the proviso that the terminal methylene unit bound to hydrogen is not replaced with —S—, —$S(=O)$—, or —$S(=O)_2$—;
wherein each of $R^a$ and $R^{10}$ is independently as defined above and described herein.

In certain embodiments, $R^4$ is a $C_0$-$C_6$ straight or branched, alkylene chain wherein each methylene unit in $R^4$ is substituted with two $R^a$, and one or two methylene units of $R^4$ are optionally and independently replaced by —O—, —S—, —$S(=O)$—, —$S(=O)_2$—, or —$N(R^{10})$—, with the proviso that the terminal methylene unit bound to hydrogen is not replaced with —S—, —$S(=O)$—, or —$S(=O)_2$—, wherein each of $R^a$ and $R^{10}$ is independently as defined above and described herein.

As defined generally above and herein, each $R^a$ is independently selected from hydrogen, $C_1$-$C_4$ alkyl, halo, —$N(R^{10})_2$, —OH, —O—($C_1$-$C_4$ alkyl), or —CN; or
  two $R^a$ bound to the same carbon atom are taken together to form =O, monocyclic carbocyclyl or a monocyclic heterocyclyl;
wherein each $R^{10}$ is independently as defined above and described herein.

In some embodiments, each $R^a$ is independently selected from hydrogen, $C_1$-$C_4$ alkyl, halo, —$N(R^{10})_2$, —OH, —O—($C_1$-$C_4$ alkyl), or —CN; or
  two $R^a$ bound to the same carbon atom are taken together to form =O.

In some embodiments, each $R^a$ is hydrogen.

In some embodiments, each $R^a$ is independently selected from $C_1$-$C_4$ alkyl, halo, —N($R^{10}$)$_2$, —OH, —O—($C_1$-$C_4$ alkyl), or —CN, wherein each $R^{10}$ is independently as defined above and described herein. In some embodiments, two $R^a$ bound to the same carbon atom are taken together to form =O. In some embodiments, each $R^a$ is independently $C_1$-$C_4$ alkyl.

In some embodiments, each $R^a$ is independently hydrogen or $C_1$-$C_4$ alkyl.

In some embodiments, each $R^4$ is —CH$_2$—.

In some embodiments, —$R^4$—H is hydrogen (e.g., $R^4$ is $C_0$ alkylene, e.g., a bond). In some embodiments, —$R^4$—H is —CH$_3$. In some embodiments, —$R^4$—H is selected from hydrogen and —CH$_3$.

As defined generally above and herein, $R^5$ is a $C_1$-$C_6$ straight or branched alkylene chain, or a $C_2$-$C_6$ straight or branched alkenylene or alkynylene chain, wherein each methylene unit in $R^5$ is substituted with two $R^a$, each =CH— unit is substituted with $R^a$; and one or two methylene units of $R^5$ are optionally and independently replaced by —O—, —S—, —S(=O)—, —S(=O)$_2$—, or —NR$^{10}$—, with the proviso that the terminal methylene unit bound to hydrogen is not replaced with —S—, —S(=O)—, or —S(=O)$_2$—; or
one methylene unit of $R^5$ is taken together with $X^1$ or $X^4$, when the $X^1$ or $X^4$ is =C($R^3$)—, and the intervening atoms to form an optionally substituted aryl, heteroaryl, heterocyclyl or carbocyclyl fused to the ring comprising $X^1$, $X^2$, $X^3$, $X^4$ and $X^5$;

wherein each of $R^a$, $R^{10}$, $X^1$, $X^2$, $X^3$, $X^4$, $X^5$, and $R^3$ is independently as defined above and described herein.

It will be understood by those of skill in the art that because the compounds of the invention are limited to compounds that are stable, $R^4$ and/or $R^5$ moieties formed by replacing two methylene units with certain combinations of —O—, —S—, —S(=O)—, —S(=O)$_2$—, or —NR$^{10}$— are not within the scope of the present invention. For example, compounds wherein the $R^4$ and/or $R^5$ moiety comprises an —O—, —S—, —S(O)—, —S(O)$_2$, or —N($R^{10}$)—, adjacent to an —O—, —S—, —S(O)—, —S(O)$_2$, or —N($R^{10}$)— are not within the scope of the present invention, except for an —S(O)$_2$— adjacent to a —N($R^{10}$)—. In addition, neither $R^4$, nor $R^5$ should comprise —O—C($R^a$)$_2$—O—, —N—C($R^a$)$_2$—O—, or —O—C($R^a$)$_2$—N—, except when the two $R^4$ bound to the same carbon atom are taken together to form =O.

In certain embodiments, $R^5$ is a $C_1$-$C_6$ straight or branched, optionally substituted alkylene chain wherein one or two methylene units of $R^5$ are optionally and independently replaced by —O—, —S—, —S(=O)—, —S(=O)$_2$—, or —NR$^{10}$—; or:
one methylene unit of $R^5$ is taken together with $X^1$ or $X^4$, when the $X^1$ or $X^4$ is =C($R^3$)—, and the intervening atoms to form an aryl, heteroaryl, heterocyclyl or carbocyclyl fused to the ring comprising $X^1$, $X^2$, $X^3$, $X^4$ and $X^5$, wherein the aryl, heteroaryl, heterocyclyl or carbocyclyl is optionally substituted with one or more substituents independently selected from halo, —OH, —CN, $C_1$-$C_4$ alkyl, $C_1$-$C_4$ haloalkyl, —O—($C_1$-$C_4$ alkyl), and —N($R^{10}$)$_2$;

wherein each of $R^a$, $R^{10}$, $X^1$, $X^2$, $X^3$, $X^4$, $X^5$, and $R^3$ is independently as defined above and described herein.

In some embodiments, each $R^a$ is independently hydrogen or $C_1$-$C_4$ alkyl. In some embodiments, each methylene unit in $R^5$ is —C(H)$_2$. In some embodiments, each methylene unit in $R^5$ is independently replaced by —C($R^a$)$_2$— wherein each $R^a$ is independently $C_1$-$C_4$ alkyl.

In some embodiments, each methylene unit in $R^5$ is independently replaced by —C($R^a$)$_2$—, —O—, —S—, —S(=O)—, —S(=O)$_2$—, or —NR$^{10}$—, wherein each of $R^a$ and $R^{10}$ is independently as defined above and described herein. In some embodiments, each methylene unit in $R^5$ is independently replaced by —CH$_2$—, —CH(CH$_3$)—, —NH—, —C(=O)—, and —S(=O)$_2$—.

In some embodiments, one methylene unit of $R^5$ is taken together with $X^1$ or $X^4$, when the $X^1$ or $X^4$ is =C($R^3$)—, and the intervening atoms to form an aryl, heteroaryl, heterocyclyl or carbocyclyl fused to the ring comprising $X^1$, $X^2$, $X^3$, $X^4$ and $X^5$, wherein the aryl, heteroaryl, heterocyclyl or carbocyclyl is optionally substituted. In one aspect of these embodiments, each optional substituent is independently selected from halo, —OH, —CN, $C_1$-$C_4$ alkyl, $C_1$-$C_4$ haloalkyl, —O—($C_1$-$C_4$ alkyl), and —N($R^{10}$)$_2$, wherein each of $X^1$, $X^2$, $X^3$, $X^4$, $X^5$, $R^3$, and $R^{10}$ is independently as defined above and described herein.

In some embodiments, one methylene unit $R^5$ is take together with $X^4$, when $X^4$ is =C($R^3$)—, and the intervening atoms to form an optionally substituted heterocyclyl fused to the ring comprising $X^1$, $X^2$, $X^3$, $X^4$ and $X^5$, wherein the heterocyclyl is optionally substituted with one or more substituents independently selected from halo, —OH, —CN, $C_1$-$C_4$ alkyl, $C_1$-$C_4$ haloalkyl, —O—($C_1$-$C_4$ alkyl), and —N($R^{10}$)$_2$, wherein each of $X^1$, $X^2$, $X^3$, $X^4$, $X^5$, $R^3$, and $R^{10}$ is independently as defined above and described herein.

In some embodiments, one methylene unit in $R^5$ is take together with $X^4$, when $X^4$ is =C($R^3$)—, and the intervening atoms to form an optionally substituted heterocyclyl selected from

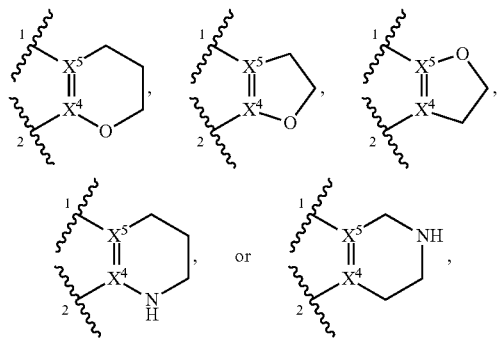

wherein:
the heterocyclyl is optionally substituted with one or more substituents independently selected from —CH$_3$, —CH$_2$CH$_3$, or phenyl;

represents a point of attachment to $X^1$;

represents a point of attachment to $X^3$; and each of $X^1$, $X^2$, $X^3$, $X^4$, $X^5$, and $R^3$ is independently as defined above and described herein.

In some embodiments, —$R^5$—H is selected from —$CH_3$, —$CH(CH_3)_2$, —$(CH_2)_2CH_3$, —$CH_2CH_3$, —$OCH_2CH_3$, —$OCH(CH_3)_2$, —$OCH_3$, —$OCH_2CH(CH_3)_2$, —OH, —$CH_2OH$, —$(CH_2)_2OH$, —$(CH_2)_2$—O—$CH_3$, —NH—C(=O)—$CH_3$, —$(CH_2)_2$—NH—$CH_3$, —$(CH_2)_2$—NH—C(=O)—$CH_3$, —$CH_2$—C(=O)$NH_2$, —NH—S(=O)$_2$—$CH_3$, and —NH—C(=O)—NH—$CH_3$.

In some embodiments, —$R^5$—H is selected from —$CH_3$, —$CH(CH_3)_2$, —$(CH_2)_2CH_3$, —$CH_2CH_3$, —$OCH_2CH_3$, —$OCH(CH_3)_2$, —$OCH_3$, or —$OCH_2CH(CH_3)_2$.

In some embodiments, no more than two consecutive methylene units in $R^4$ are replaced by —O— or —S—. In some embodiments, no more than three consecutive methylene units in $R^4$ are replaced by —O— or —S—.

In some embodiments, no more than two consecutive methylene units in $R^5$ are replaced by —O— or —S—. In some embodiments, no more than three consecutive methylene units in $R^5$ are replaced by —O— or —S—.

In some embodiments, when Z is =C($R^2$)—, $X^4$ is =N— or =C($R^3$)—, and $X^1$ and $X^4$ are not simultaneously =N—, then the portion of the compound represented by —C($R^4$—H)($R^5$—H)($R^6$) is other than $C_1$-$C_6$ alkyl, $C_2$-$C_6$ alkenyl or $C_2$-$C_6$ alkynyl, any of which is optionally substituted with one or more of halo, hydroxyl, COOH, C(O)O—$C_1$-$C_6$ alkyl, cyano, $C_1$-$C_6$ alkoxyl, amino, mono-$C_1$-$C_6$ alkylamino or di-$C_1$-$C_6$ alkylamino.

In some embodiments, when Z is =C($R^2$)—, each of $X^1$ and $X^4$ is =C($R^3$)—, and the portion of the compound represented by —C($R^4$—H)($R^5$—H)($R^6$) is $C_1$-$C_6$ alkyl, $C_2$-$C_6$ alkenyl or $C_2$-$C_6$ alkynyl, any of which is optionally substituted with one or more of halo, hydroxyl, COOH, C(O)O—$C_1$-$C_6$ alkyl, cyano, $C_1$-$C_6$ alkoxyl, amino, mono-$C_1$-$C_6$ alkylamino or di-$C_1$-$C_6$ alkylamino, then each of the $R^3$ portions of $X^1$ and $X^4$ are independently selected from hydrogen, halo, —OH, —CN, $C_1$-$C_4$ alkyl, $C_2$-$C_4$ alkenyl or alkynyl, —O—($C_1$-$C_4$ alkyl), N($R^7$)$_2$, —($C_1$-$C_4$ alkylene)-aryl, —($C_1$-$C_4$ alkylene)-heteroaryl, —($C_0$-$C_4$ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, —O—($C_0$-$C_4$ alkylene)-carbocyclyl, —C(O)O$R^9$, —C(O)N($R^9$)$_2$, —S(O)$R^8$, —S(O)$_2R^8$ and —S(O)$_2$N($R^9$)$_2$, wherein each of $R^7$, $R^8$ and $R^9$ is independently as defined above and described herein.

As defined generally above and herein, $R^6$ is hydrogen or methyl. In some embodiments, $R^6$ is hydrogen. In some embodiments, $R^6$ is methyl.

In some embodiments, —$R^4$—H is selected from hydrogen and methyl; and $R^6$ is hydrogen.

As defined generally above and herein, each $R^7$ is independently selected from hydrogen, —($C_0$-$C_4$ alkylene)-$R^9$, —($C_2$-$C_4$ alkylene)-O—$R^9$, $C_2$-$C_4$ haloalkyl, —S(O)$_2$—$R^8$, —C(=O)—$R^8$, —C(=O)—N($R^9$)($R^9$), —($C_2$-$C_4$ alkylene)-O—C(=O)—$R^8$ and —($C_0$-$C_4$ alkylene)-C(=O)—O—$R^9$; or two $R^7$ are taken together with the nitrogen atom to which they are commonly bound to form an optionally substituted heterocyclyl or heteroaryl;

wherein each of $R^8$ and $R^9$ is independently as defined above and described herein.

In some embodiments, each $R^7$ is independently selected from hydrogen, $C_1$-$C_4$ alkyl, $C_1$-$C_4$ haloalkyl, —S(=O)$_2$—$R^8$, —C(=O)—$R^8$, —C(=O)—N($R^8$)($R^9$), and —C(=O)—O—$R^8$; or or two $R^7$ are taken together with the nitrogen atom to which they are commonly bound to form an optionally substituted heterocyclyl or heteroaryl;

wherein each of $R^8$ and $R^9$ is independently as defined above and described herein.

In some embodiments, each $R^7$ is independently selected from hydrogen, $C_1$-$C_4$ alkyl, $C_1$-$C_4$ haloalkyl, —S(=O)$_2$—$R^8$, —C(=O)—$R^8$, —C(=O)—N($R^8$)($R^9$), and —C(=O)—O—$R^8$; or or two $R^7$ are taken together with the nitrogen atom to which they are commonly bound to form an optionally substituted heterocyclyl;

wherein each of $R^8$ and $R^9$ is independently as defined above and described herein.

In some embodiments, each $R^7$ is independently selected from hydrogen, $C_1$-$C_4$ alkyl, $C_1$-$C_4$ haloalkyl, —S(=O)$_2$—$R^8$, —C(=O)—$R^8$, —C(=O)—N($R^8$)($R^9$), and —C(=O)—O—$R^8$; or or two $R^7$ are taken together with the nitrogen atom to which they are commonly bound to form an optionally substituted heteroaryl;

wherein each of $R^8$ and $R^9$ is independently as defined above and described herein.

As defined generally above and herein, $R^8$ is selected from $C_1$-$C_4$ alkyl, aryl, heteroaryl, carbocyclyl and heterocyclyl.

As defined generally above and herein, $R^9$ is selected from hydrogen or $R^8$, wherein $R^8$ is as defined above and described herein. In some embodiments, $R^9$ is hydrogen. In some embodiments, $R^9$ is $R^8$, wherein $R^8$ is as defined above and described herein.

As defined generally above and herein, each $R^{10}$ is independently selected from hydrogen, $C_1$-$C_4$ alkyl, $C_2$-$C_4$ haloalkyl, —S(=O)$_2$—$R^{11}$, —C(=O)—$R^{11}$, —C(=O)—N($R^{11}$)($R^{12}$), and —C(=O)—O—$R^{11}$, wherein each of $R^{11}$ and $R^{12}$ is independently as defined above and described herein.

In some embodiments, each $R^{10}$ is hydrogen In some embodiments, each $R^{10}$ is independently selected from $C_1$-$C_4$ alkyl, $C_2$-$C_4$ haloalkyl, —S(=O)$_2$—$R^{11}$, —C(=O)—$R^{11}$, —C(=O)—N($R^{11}$)($R^{12}$), and —C(=O)—O—$R^{11}$, wherein each of $R^{11}$ and $R^{12}$ is independently as defined above and described herein.

As defined generally above and herein, $R^{11}$ is $C_1$-$C_4$ alkyl.

In some embodiments, $R^{11}$ is selected from $C_1$-$C_4$ alkyl, and $C_1$-$C_4$ haloalkyl.

As defined generally above and herein, $R^{12}$ is selected from hydrogen, and $C_1$-$C_4$ alkyl.

In some embodiments, $R^{12}$ is selected from hydrogen, $C_1$-$C_4$ alkyl, and $C_1$-$C_4$ haloalkyl.

As defined generally above and herein, === represents a single or double bond. In some embodiments, === represents a single bond. In some embodiments, === represents a double bond. In some embodiments, the bond between $X^4$ and $X^5$ is a single bond. In some embodiments, the bond between $X^4$ and $X^5$ is a double bond.

Unless otherwise designated, any alkyl, alkylene, alkenyl, alkenylene, alkynyl, alkynylene, aryl, heteroaryl, heterocyclyl or carbocyclyl portion of the compound is optionally substituted.

In some embodiments, the present invention provides a compound of formula I-i:

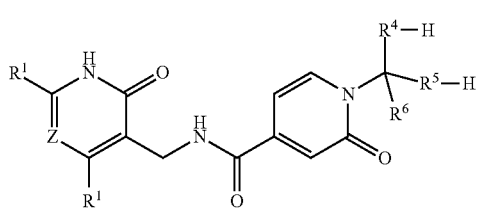

I-i or a pharmaceutically acceptable salt thereof, wherein each variable is defined above and described in classes and subclasses above and herein.

In some embodiments, the present invention provides a compound of formula I-i:

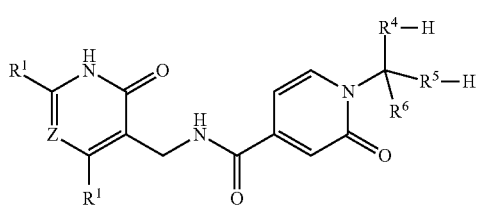

I-i or a pharmaceutically acceptable salt thereof, wherein:
$R^6$ is hydrogen; and
each of $R^1$, Z, $R^4$, and $R^5$ is independently as defined above or described herein.

In some embodiments, the present invention provides a compound of formula I-i:

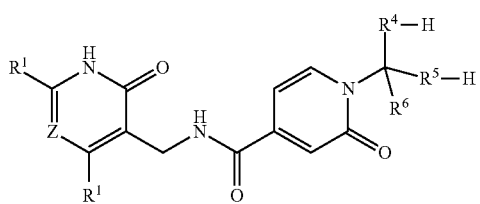

I-i or a pharmaceutically acceptable salt thereof, wherein:
$R^4$ is —CH$_2$—, —C(R$^a$)$_2$—, —O—, —S—, —S(=O)—, —S(=O)$_2$—, or —N(R$^{10}$)—;
$R^5$ is —CH$_2$—, —C(R$^a$)$_2$—, —O—, —S—, —S(=O)—, —S(=O)$_2$—, or —NR$^{10}$—; and
each of $R^1$, Z, $R^6$, $R^a$, and $R^{10}$ is independently as defined above or described herein.

In some embodiments, the present invention provides a compound of formula I-i:

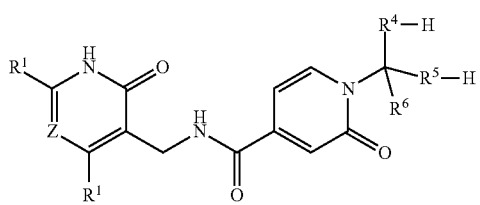

I-i or a pharmaceutically acceptable salt thereof, wherein:
$R^4$ is —CH$_2$—, —C(R$^a$)$_2$—, —O—, or —N(R$^{10}$)—;
$R^5$ is —CH$_2$—, —C(R$^a$)$_2$—, —O—, or —NR$^{10}$—; and
each of $R^1$, Z, $R^6$, $R^a$, and $R^{10}$ is independently as defined above or described herein.

In some embodiments, the present invention provides a compound of formula I-i:

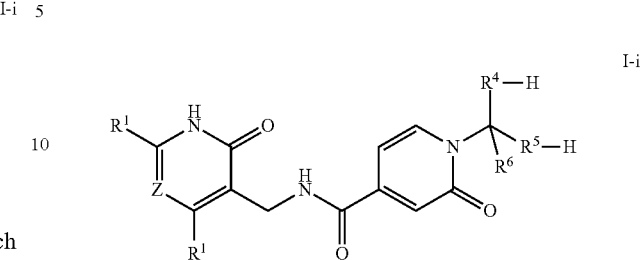

I-i or a pharmaceutically acceptable salt thereof, wherein:
—R$^4$—H is —CH$_3$;
—R$^5$—H is selected from —CH$_3$, —CH(CH$_3$)$_2$, —(CH$_2$)$_2$CH$_3$, —CH$_2$CH$_3$, —OCH$_2$CH$_3$, —OCH(CH$_3$)$_2$, —OCH$_3$, and —OCH$_2$CH(CH$_3$)$_2$;
$R^6$ is hydrogen; and
each of Z and $R^1$ is independently as defined above and described herein.

In certain embodiments, the present invention provides a compound of formula I:

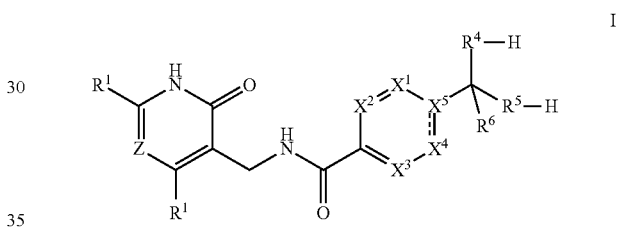

I or a pharmaceutically acceptable salt thereof, wherein:
Z is =C(R$^2$)— or =N—;
each of $X^1$, $X^2$ and $X^3$ is independently selected from =N— and =C(R$^3$)—;
$X^4$ is selected from =N—, —C(=O)— and =C(R$^3$)—;
$X^5$ is =C— or

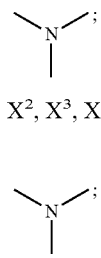

no more than two of $X^1$, $X^2$, $X^3$, $X^4$, and $X^5$ are =N— or

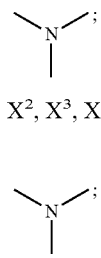

each $R^1$ and $R^2$ is independently selected from hydrogen, halo, —OH, —CN, C$_1$-C$_4$ alkyl, —O—(C$_1$-C$_4$ alkyl), N(R$^7$)$_2$, —(C$_0$-C$_4$ alkylene)-aryl, —(C$_0$-C$_4$ alkylene)-heteroaryl, —(C$_0$-C$_4$ alkylene)-heterocyclyl, —(C$_0$-C$_4$ alkylene)-carbocyclyl, —O—(C$_0$-C$_4$ alkylene)-aryl, —O—(C$_0$-C$_4$ alkylene)-heteroaryl, —O—(C$_0$-C$_4$ alkylene)-heterocyclyl, —O—(C$_0$-C$_4$ alkylene)-carbocyclyl; or one $R^1$ and $R^2$ are taken together with atoms to which they are bound to form an aryl, heteroaryl, heterocyclyl, or carbocyclyl;
each $R^3$ is independently selected from hydrogen, halo, —OH, —CN, C$_1$-C$_4$ alkyl, C$_2$-C$_4$ alkenyl or alkynyl, —O—(C$_1$-C$_4$ alkyl), N(R$^7$)$_2$, —(C$_0$-C$_4$ alkylene)-aryl, —(C₀-C₄ alkylene)-heteroaryl, —(C₀-C₄ alkylene)-heterocyclyl, —(C₀-C₄ alkylene)-carbocyclyl, —O—(C₀-C₄ alkylene)-aryl, —O—(C₀-C₄ alkylene)-heteroaryl, —O—(C₀-C₄ alkylene)-heterocyclyl, —O—(C₀-C₄ alkylene)-carbocyclyl, —C(O)OR⁹, —C(O)N(R⁹)₂, —S(O)R⁸, —S(O)₂R⁸ and —S(O)₂N(R⁹)₂;

R⁴ is a C₀-C₆ straight or branched, alkylene chain, or a C₂-C₆ straight or branched alkenylene or alkynylene chain, wherein each methylene unit in R⁴ is substituted with two Rᵃ; each =CH-unit is substituted with Rᵃ; and one or two methylene units of R⁴ are optionally and independently replaced by —O—, —S—, —S(=O)—, —S(=O)₂—, or —N(R¹⁰)—, with the proviso that the terminal methylene unit bound to hydrogen is not replaced with —S—, —S(=O)—, or —S(=O)₂—;

each Rᵃ is independently selected from hydrogen, C₁-C₄ alkyl, halo, —N(R¹⁰)₂, —OH, —O—(C₁-C₄ alkyl), or —CN; or two Rᵃ bound to the same carbon atom are taken together to form =O, monocyclic carbocyclyl or a monocyclic heterocyclyl;

R⁵ is a C₁-C₆ straight or branched alkylene chain, or a C₂-C₆ straight or branched alkenylene or alkynylene chain, wherein each methylene unit in R⁵ is substituted with two Rᵃ, each =CH-unit is substituted with Rᵃ; and one or two methylene units of R⁵ are optionally and independently replaced by —O—, —S—, —S(=O)—, —S(=O)₂—, or —NR¹⁰—, with the proviso that the terminal methylene unit bound to hydrogen is not replaced with —S—, —S(=O)—, or —S(=O)₂—; or one methylene unit of R⁵ is taken together with X¹ or X⁴, when the X¹ or X⁴ is =C(R³)—, and the intervening atoms to form an optionally substituted aryl, heteroaryl, heterocyclyl or carbocyclyl fused to the ring comprising X¹, X², X³, X⁴ and X⁵;

R⁶ is hydrogen or methyl;

each R⁷ is independently selected from hydrogen, —(C₀-C₄ alkylene)-R⁹, —(C₂-C₄ alkylene)-O—R⁹, C₂-C₄ haloalkyl, —S(O)₂—R⁸, —C(=O)—R⁸, —C(=O)—N(R⁹)(R⁹), —(C₂-C₄ alkylene)-O—C(=O)—R⁸ and —(C₀-C₄ alkylene)-C(=O)—O—R⁹; or two R⁷ are taken together with the nitrogen atom to which they are commonly bound to form an optionally substituted heterocyclyl or heteroaryl;

R⁸ is selected from C₁-C₄ alkyl, aryl, heteroaryl, carbocyclyl and heterocyclyl;

each R⁹ is independently selected from hydrogen or R⁸;

each R¹⁰ is independently selected from hydrogen, C₁-C₄ alkyl, C₂-C₄ haloalkyl, —S(=O)₂—R¹¹, —C(=O)—R¹¹, —C(=O)—N(R¹¹)(R¹²), and —C(=O)—O—R¹¹;

R¹¹ is C₁-C₄ alkyl;

R¹² is selected from hydrogen, and C₁-C₄ alkyl;

=== represents a single or double bond;

wherein unless otherwise designated any alkyl, alkylene, alkenyl, alkenylene, alkynyl, alkynylene, aryl, heteroaryl, heterocyclyl or carbocyclyl portion of the compound is optionally substituted;

wherein:

when each of X¹, X², X³ and X⁴ is =C(H)—, X⁵ is =C— and each of R⁴ and R⁶ is hydrogen, then R⁵ is other than —NH—C(=O)—(C₁-C₄ alkyl), —N(C₁-C₄ alkyl)₂, —C₁-C₄ straight alkyl, —O—CH₂—CF₃, or —OCH₃;

when each of X¹, X², X³ and X⁴ is =C(H)—, X⁵ is =C— and R⁴ is —CH₃, then R⁵ is other than —CH₃;

and the compound is other than:

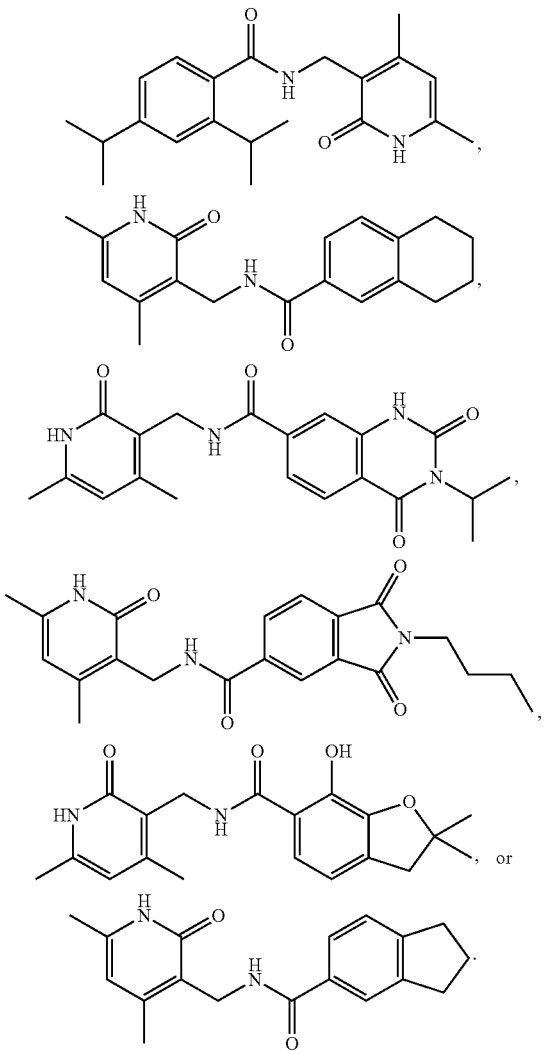

In certain embodiments, the present invention provides a compound of formula I:

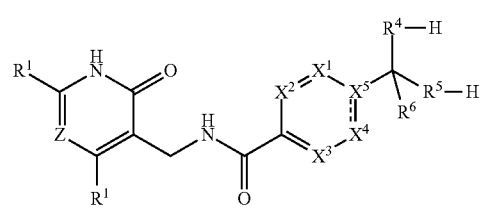

or a pharmaceutically acceptable salt thereof, wherein:

Z is =C(R²)— or =N—;

each of X¹, X² and X³ is independently selected from =N— and =C(R³)—;

X⁴ is selected from =N—, —C(=O)— and =C(R³)—;

$X^5$ is =C— or $$\diagdown N \diagup ;$$
$$|$$

no more than two of $X^1$, $X^2$, $X^3$, $X^4$, and $X^5$ are =N— or $$\diagdown N \diagup ;$$
$$|$$

each $R^1$ and $R^2$ is independently selected from hydrogen, halo, —OH, —CN, $C_1$-$C_4$ alkyl, —O—($C_1$-$C_4$ alkyl), $N(R^7)_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, —O—($C_0$-$C_4$ alkylene)-carbocyclyl; or
one $R^1$ and $R^2$ are taken together with atoms to which they are bound to form an aryl, heteroaryl, heterocyclyl, or carbocyclyl;
each $R^3$ is independently selected from hydrogen, halo, —OH, —CN, $C_1$-$C_4$ alkyl, $C_2$-$C_4$ alkenyl or alkynyl, —O—($C_1$-$C_4$ alkyl), $N(R^7)_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, —O—($C_0$-$C_4$ alkylene)-carbocyclyl, —C(O)OR$^9$, —C(O)N(R$^9$)$_2$, —S(O)R$^8$, —S(O)$_2$R$^8$ and —S(O)$_2$N(R$^9$)$_2$;
$R^4$ is a $C_0$-$C_6$ straight or branched, alkylene chain, or a $C_2$-$C_6$ straight or branched alkenylene or alkynylene chain, wherein each methylene unit in $R^4$ is substituted with two $R^a$; each =CH-unit is substituted with $R^a$; and one or two methylene units of $R^4$ are optionally and independently replaced by —O—, —S—, —S(=O)—, —S(=O)$_2$—, or —N(R$^{10}$)—, with the proviso that the terminal methylene unit bound to hydrogen is not replaced with —S—, —S(=O)—, or —S(=O)$_2$—;
each $R^a$ is independently selected from hydrogen, $C_1$-$C_4$ alkyl, halo, —N(R$^{10}$)$_2$, —OH, —O—($C_1$-$C_4$ alkyl), or —CN; or
two $R^a$ bound to the same carbon atom are taken together to form =O, monocyclic carbocyclyl or a monocyclic heterocyclyl;
$R^5$ is a $C_1$-$C_6$ straight or branched alkylene chain, or a $C_2$-$C_6$ straight or branched alkenylene or alkynylene chain, wherein each methylene unit in $R^5$ is substituted with two $R^a$, each =CH-unit is substituted with $R^a$; and one or two methylene units of $R^5$ are optionally and independently replaced by —O—, —S—, —S(=O)—S(=O)$_2$—, or —NR$^{10}$—, with the proviso that the terminal methylene unit bound to hydrogen is not replaced with —S —S(=O)—, or —S(=O)$_2$—; or
one methylene unit of $R^5$ is taken together with $X^1$ or $X^4$, when the $X^1$ or $X^4$ is =C(R$^3$)—, and the intervening atoms to form an optionally substituted aryl, heteroaryl, heterocyclyl or carbocyclyl fused to the ring comprising $X^1$, $X^2$, $X^3$, $X^4$ and $X^5$;
$R^6$ is hydrogen or methyl;
each $R^7$ is independently selected from hydrogen, —($C_0$-$C_4$ alkylene)-R$^9$, —($C_2$-$C_4$ alkylene)-O—R$^9$, $C_2$-$C_4$ haloalkyl, —S(O)$_2$—R$^8$, —C(=O)—R$^8$, —C(=O)—N(R$^9$)(R$^9$), —($C_2$-$C_4$ alkylene)-O—C(=O)—R$^8$ and —($C_0$-$C_4$ alkylene)-C(=O)—O—R$^9$; or
two $R^7$ are taken together with the nitrogen atom to which they are commonly bound to form an optionally substituted heterocyclyl or heteroaryl;
$R^8$ is selected from $C_1$-$C_4$ alkyl, aryl, heteroaryl, carbocyclyl and heterocyclyl;
each $R^9$ is independently selected from hydrogen or $R^8$;
each $R^{10}$ is independently selected from hydrogen, $C_1$-$C_4$ alkyl, $C_2$-$C_4$ haloalkyl, —S(=O)$_2$—R$^{11}$, —C(=O)—R$^{11}$, —C(=O)—N(R$^{11}$)(R$^{12}$), and —C(=O)—O—R$^{11}$;
$R^{11}$ is $C_1$-$C_4$ alkyl;
$R^{12}$ is selected from hydrogen, and $C_1$-$C_4$ alkyl;
=== represents a single or double bond;
wherein unless otherwise designated any alkyl, alkylene, alkenyl, alkenylene, alkynyl, alkynylene, aryl, heteroaryl, heterocyclyl or carbocyclyl portion of the compound is optionally substituted;
wherein:
when each of $X^1$, $X^2$, $X^3$ and $X^4$ is =C(H)—, $X^5$ is =C— and each of $R^4$ and $R^6$ is hydrogen, then $R^5$ is other than —NH—C(=O)—($C_1$-$C_4$ alkyl), —N($C_1$-$C_4$ alkyl)$_2$, —$C_1$-$C_4$ straight alkyl, —O—CH$_2$—CF$_3$, or —OCH$_3$;
when each of $X^1$, $X^2$, $X^3$ and $X^4$ is =C(H)—, $X^5$ is =C— and $R^4$ is —CH$_3$, then $R^5$ is other than —CH$_3$;
when Z is =C(R$^2$)—, $X^4$ is =N— or =C(R$^3$)—, and $X^1$ and $X^4$ are not simultaneously =N—, then the portion of the compound represented by —C(R$^4$—H)(R$^5$—H)(R$^6$) is other than $C_1$-$C_6$ alkyl, $C_2$-$C_6$ alkenyl or $C_2$-$C_6$ alkynyl, any of which is optionally substituted with one or more of halo, hydroxyl, COOH, C(O)O—$C_1$-$C_6$ alkyl, cyano, $C_1$-$C_6$ alkoxyl, amino, mono-$C_1$-$C_6$ alkylamino or di-$C_1$-$C_6$ alkylamino;
when Z is =C(R$^2$)—, each of $X^1$ and $X^4$ is =C(R$^3$)—, and the portion of the compound represented by —C(R$^4$—H)(R$^5$—H)(R$^6$) is $C_1$-$C_6$ alkyl, $C_2$-$C_6$ alkenyl or $C_2$-$C_6$ alkynyl, any of which is optionally substituted with one or more of halo, hydroxyl, COOH, C(O)O—$C_1$-$C_6$ alkyl, cyano, $C_1$-$C_6$ alkoxyl, amino, mono-$C_1$-$C_6$ alkylamino or di-$C_1$-$C_6$ alkylamino, then each of the $R^3$ portions of $X^1$ and $X^4$ are independently selected from hydrogen, halo, —OH, —CN, $C_1$-$C_4$ alkyl, $C_2$-$C_4$ alkenyl or alkynyl, —O—($C_1$-$C_4$ alkyl), $N(R^7)_2$, —($C_1$-$C_4$ alkylene)-aryl, —($C_1$-$C_4$ alkylene)-heteroaryl, —($C_0$-$C_4$ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, —O—($C_0$-$C_4$ alkylene)-carbocyclyl, —C(O)OR$^9$, —C(O)N(R$^9$)$_2$, —S(O)R$^8$, —S(O)$_2$R$^8$ and —S(O)$_2$N(R$^9$)$_2$;
and the compound is other than:

-continued
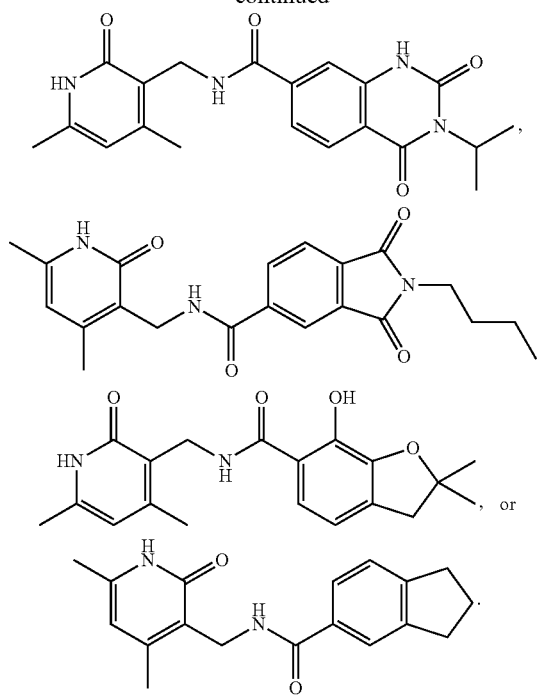
Exemplary compounds of formula I are set forth in Table 1, below.
TABLE 1
Exemplary Compounds of Formula I:
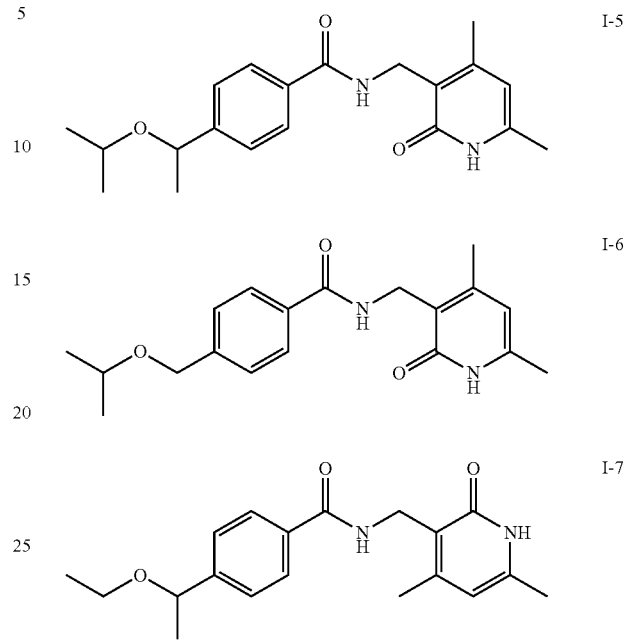
TABLE 1-continued
Exemplary Compounds of Formula I:
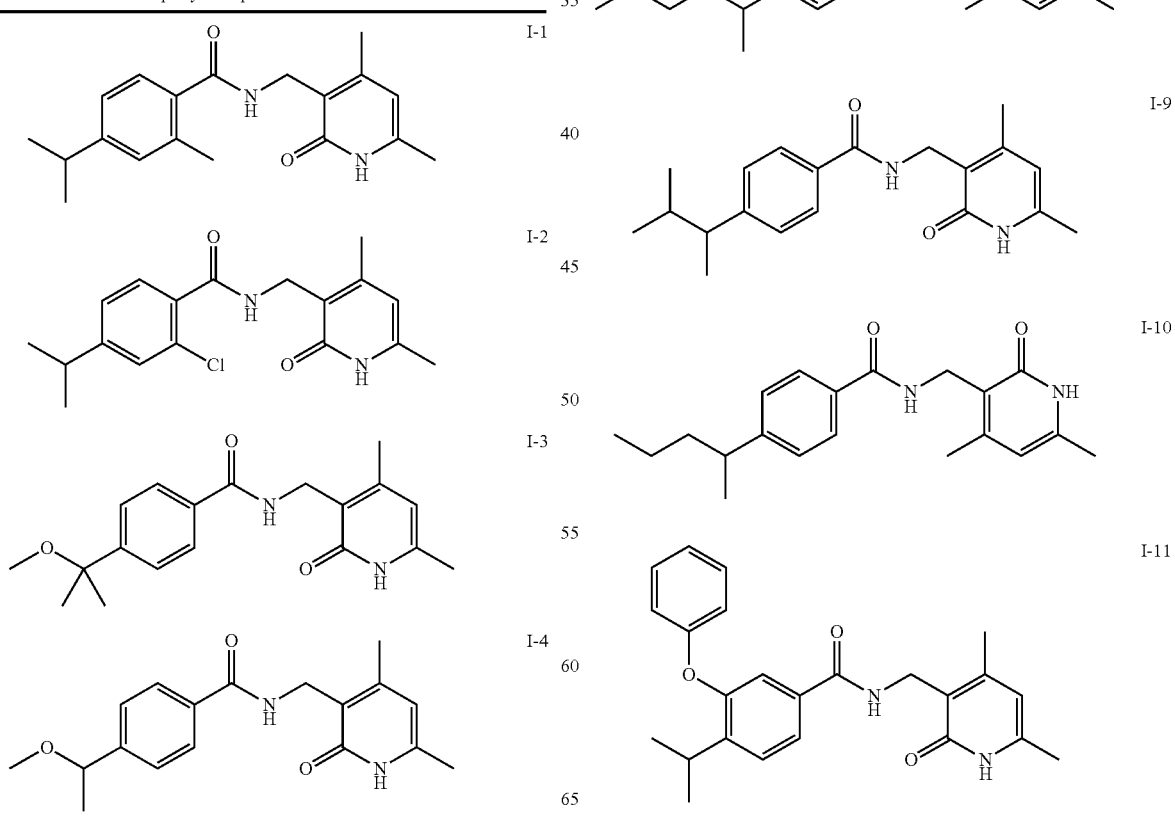

TABLE 1-continued
Exemplary Compounds of Formula I:
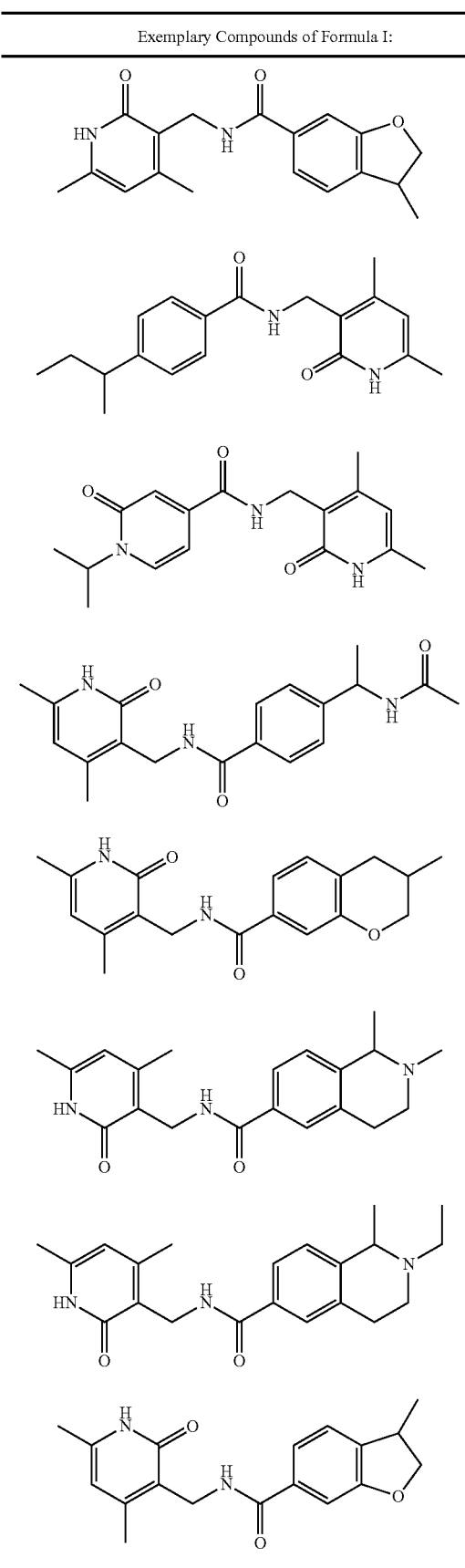
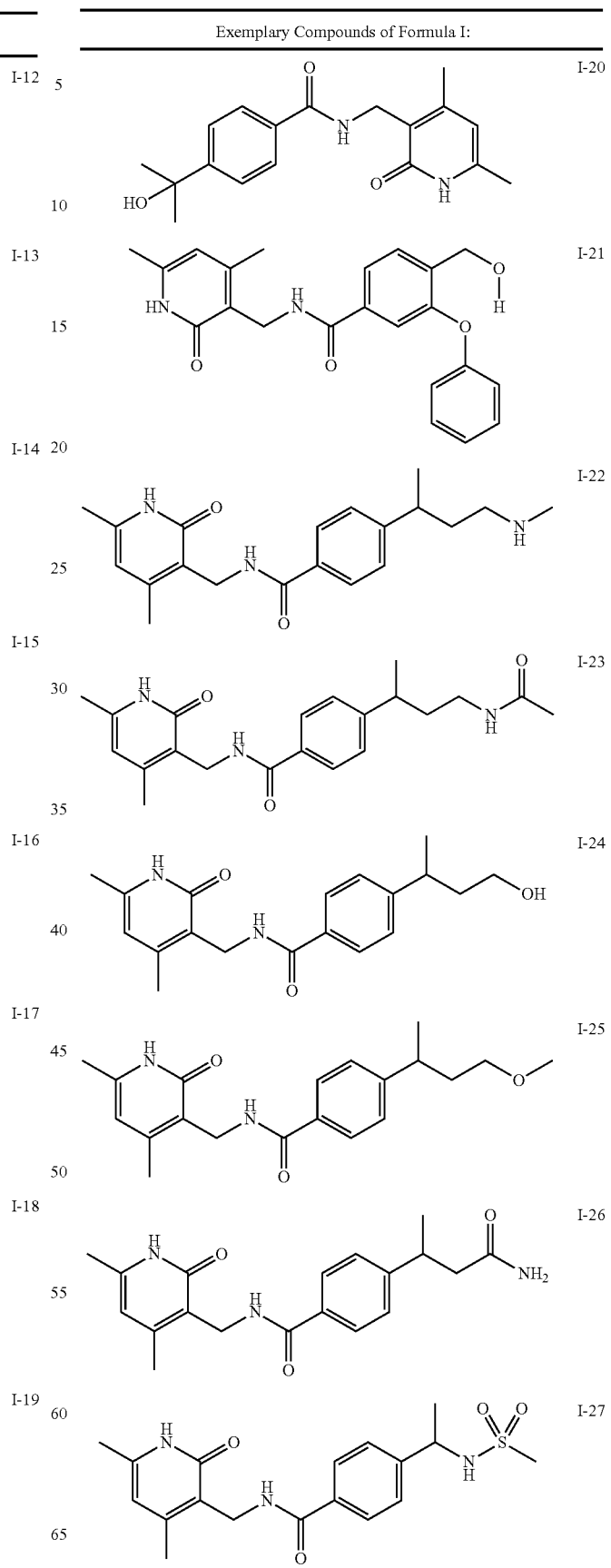

TABLE 1-continued

Exemplary Compounds of Formula I:

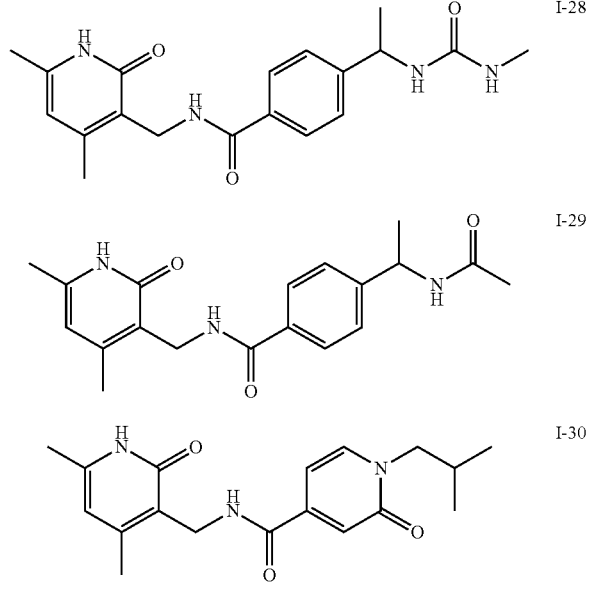

I-28

I-29

I-30

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably modulate a histone methyl modifying enzyme, or a mutant thereof, in a biological sample or in a patient. In certain embodiments, the amount of compound in compositions of this invention is such that is effective to measurably modulate a histone methyl modifying enzyme, or a mutant thereof, in a biological sample or in a patient.

In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated and the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the modulating of activity of one or more enzymes involved in epigenetic regulation.

Epigenetics is the study of heritable changes in gene expression caused by mechanisms other than changes in the underlying DNA sequence. Molecular mechanisms that play a role in epigenetic regulation include DNA methylation and chromatin/histone modifications. Histone methylation, in particular, is critical in many epigenetic phenomena.

Chromatin, the organized assemblage of nuclear DNA and histone proteins, is the basis for a multitude of vital nuclear processes including regulation of transcription, replication, DNA-damage repair and progression through the cell cycle. A number of factors, such as chromatin-modifying enzymes, have been identified that play an important role in maintaining the dynamic equilibrium of chromatin (Margueron, et al. (2005) Curr. Opin. Genet. Dev. 15:163-176).

Histones are the chief protein components of chromatin. They act as spools around which DNA winds, and they play a role in gene regulation. There are a total of six classes of histones (H1, H2A, H2B, H3, H4, and H5) organized into two super classes: core histones (H2A, H2B, H3, and H4) and linker histones (H1 and H5). The basic unit of chromatin is the nucleosome, which consists of about 147 base pairs of DNA wrapped around the histone octamer, consisting of two copies each of the core histones H2A, H2B, H3, and H4 (Luger, et al. (1997) Nature 389:251-260).

Histones, particularly residues of the amino termini of histones H3 and H4 and the amino and carboxyl termini of histones H2A, H2B and H1, are susceptible to a variety of post-translational modifications including acetylation, methylation, phosphorylation, ribosylation, sumoylation, ubiquitination, citrullination, deimination, and biotinylation. The core of histones H2A and H3 can also be modified. Histone modifications are integral to diverse biological processes such as gene regulation, DNA repair, and chromosome condensation.

The present disclosure provides compounds and compositions for modulating activity of histone methyl modifying enzymes. Histone methyl modifying enzymes are key regulators of cellular and developmental processes. Histone methyl modifying enzymes may be characterized as either histone methyl transferases or histone demethylases. Histone demethylase enzymes have modules that mediate binding to methylated residues. For example, multiple demethylases contain a Tudor domain (e.g., JMJD2C/GASC1) or a PHD domain (e.g., JARID1C/SMCX, PHF8).

The lysine specificities of many histone methyltransferases have been characterized. For example SET7/9, SMYD3, and MLL1-5 are specific for H3K4. SUV39H1, DIM-5, and G9a are specific for H3K9. SET8 is specific for H4K20.

DOT1 is an example of a non-SET domain containing histone methylase. DOT1 methylates H3 on lysine 79.

Just as histone methylases have been shown to regulate transcriptional activity, chromatin structure, and gene silencing, demethylases have also been discovered which impact gene expression. LSD1 was the first histone lysine demethylase to be characterized. This enzyme displays homology to FAD-dependent amine oxidases and acts as a transcriptional corepressor of neuronal genes (Shi et al., Cell 119:941-953, 2004). Additional demethylases defining separate demethylase families have been discovered, including JHDM1 (or KDM2), JHDM2 (or KDM3), JMJD2 (or KDM4), JARID (or KDM5), JMJD3 (or KDM6), and JMJD6 families (Lan et al., Curr. Opin. Cell Biol. 20(3):316-325, 2008).

Demethylases act on specific lysine residues within substrate sequences and discriminate between the degree of methylation present on a given residue. For example, LSD1 removes mono- or dimethyl-groups from H3K4. Members of the JARID1A-D family remove trimethyl groups from H3K4.

UTX and JMJD3 demethylate H3K27, counteracting effects of EZH2 methylase activity. Substrate specificities of other demethylases have been characterized (see Shi, Nat. Rev. 8:829-833, 2007).

One class of histone methylases is characterized by the presence of a SET domain, named after proteins that share the domain, Su(var)3-9, enhancer of zeste [E(Z)], and trithorax. A SET domain includes about 130 amino acids. SET domain-containing methylase families include SUV39H1, SET1, SET2, EZH2, RIZ1, SMYD3, SUV4-20H1, SET7/9, and PR-SET7/SET8 families (reviewed in Dillon et al., Genome Biol. 6:227, 2005). Members of a family typically include similar sequence motifs in the vicinity of and within the SET domain. The human genome encodes over 50 SET domain-containing histone protein methylases, any of which can be used in an assay described herein.

EZH2 is an example of a human SET-domain containing methylase. EZH2 associates with EED (Embryonic Ectoderm Development) and SUZ12 (suppressor of zeste 12 homolog) to form a complex known as PRC2 (Polycomb Group Repressive Complex 2) having the ability to tri-methylate histone H3 at lysine 27 (Cao and Zhang, Mol. Cell 15:57-67, 2004). PRC2 complexes can also include RBAP46 and RBAP48 subunits.

The oncogenic activities of EZH2 have been shown by a number of studies. In cell line experiments, over-expression of EZH2 induces cell invasion, growth in soft agar, and motility while knockdown of EZH2 inhibits cell proliferation and cell invasion (Kleer et al., 2003, Proc. Nat. Acad. Sci. USA 100:11606-11611; Varambally et al., (2002), "The polycomb group protein EZH2 is involved in progression of prostate cancer," Nature 419, 624-629). It has been shown that EZH2 represses the expression of several tumor supressors, including E-cadherin, DAB2IP and RUNX3 among others. In xenograft models, EZH2 knockdown inhibits tumor growth and metastasis. Recently, it has been shown that down modulation of EZH2 in murine models blocks prostate cancer metastasis (Min et al., "An oncogene-tumor suppressor cascade drives metastatic prostate cancer by coordinately activating Ras and nuclear factor-kappaB," Nat Med. 2010 March; 16(3):286-94). EZH2 overexpression is associated with aggressiveness of certain cancers such as breast cancer (Kleer et al., Proc. Nat. Acad. Sci. USA 100:11606-11611, 2003). Recent studies also suggest that prostate cancer specific oncogenic fusion gene TMPRSS2-ERG induces repressive epigenetic programs via direct activation of EZH2 (Yu et al., "An Integrated Network of Androgen Receptor, Polycomb, and TMPRSS2-ERG Gene Fusions in Prostate Cancer Progression," Cancer Cell. 2010 May 18; 17(5):443-454).

In some embodiments, compounds of the present invention modulate the activity of one or more enzymes involved in epigenetic regulation. In some embodiments, compounds of the present invention modulate the activity of a histone methyl modifying enzyme, or a mutant thereof. In some embodiments, compounds of the present invention modulate EZH2 activity. In some embodiments, compounds of the present invention down-regulate or suppress the activity of EZH2. In some embodiments, compounds of the present invention are antagonists of EZH2 activity.

In some embodiments, compounds and compositions of the present invention are useful in treating diseases and/or disorders associated with a histone methyl modifying enzyme. Accordingly, in some embodiments, the present invention provides a method of modulating a disease and/or disorder associated with a histone methyl modifying enzyme. In some embodiments, the present invention provides a method of treating a subject suffering from a disease and/or disorder associated with a histone methyl modifying enzyme comprising the step of administering a compound or composition of formula I.

In some embodiments, compounds and compositions of the present invention are useful in treating diseases and/or disorders associated with overexpression of EZH2. In some embodiments, the present invention provides a method of treating a subject suffering from a disease and/or disorder associated with overexpression of EZH2 comprising the step of administering a compound or composition of formula I. In some embodiments, the above method additionally comprises the preliminary step of determining if the subject is overexpressing EZH2.

In some embodiments, compounds and compositions of the present invention are useful in treating diseases and/or disorders associated with cellular proliferation. In some embodiments, compounds and compositions of the present invention are useful in treating diseases and/or disorders associated with misregulation of cell cycle or DNA repair. In some embodiments, compounds and compositions of the present invention are useful in treating cancer. Exemplary types of cancer include breast cancer, prostate cancer, colon cancer, renal cell carcinoma, glioblastoma multiforme cancer, bladder cancer, melanoma, bronchial cancer, lymphoma and liver cancer.

The study of EZH2 deletions, missense and frameshift mutations suggest that EZH2 functions as a tumor suppressor in blood disorders such as myelodysplastic syndromes (MDS) and myeloid malignancies (Ernst et al., Nat Genet. 2010 August; 42(8):722-6; Nikoloski et al., Nat Genet. 2010 August; 42(8):665-7). Accordingly, in some embodiments, compounds and compositions of the present invention are useful in treating diseases and/or disorders associated with the presence of a mutant form of EZH2. In some embodiments, compounds and compositions of the present invention are useful in treating diseases and/or disorders associated with the presence of Y641N EZH2. In some embodiment, the disease or disorder associated with the presence of a mutant form of EZH2 is a human B cell lymphoma. In some embodiments, the disease and/or disorder associated with the presence of Y641N EZH2 is follicular lymphoma or diffuse large-B-cell lymphoma. In some embodiments, compounds or compositions of the present invention are useful in treating blood disorders, such as myelodysplastic syndromes, leukemia, anemia and cytopenia. Sneeringer et al., "Coordinated activities of wild-type plus mutant EZH2 drive tumor-associated hypertrimethylation of lysine 27 on histone H3 (H3K27) in human B-cell lymphomas," Proceedings of the National Academy of Sciences, PNAS Early Edition published ahead of print on Nov. 15, 2010.

In some embodiments, the present invention provides a method of reducing the activity of a mutant form of EZH2, such as Y641N EZH2, in a subject in need thereof comprising the step of administering a compound or composition of formula I. In some embodiments, the present invention provides a method of treating a subject suffering from a disease and/or disorder associated with a mutant form of EZH2 comprising the step of administering a compound or composition of formula I. In some embodiments, the above method additionally comprises the preliminary step of determining if the subject is expressing a mutant form of EZH2, such as Y641N EZH2. In some embodiments, that determination is made by determining if the subject has increased levels of histone H3 Lys-27-specific trimethylation (H3K27me3), as compared to a subject known not to express a mutant form of EZH2.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples that follow and the references to the scientific and patent literature cited herein. It should further be appreciated that the contents of those cited references are incorporated herein by reference to help illustrate the state of the art.

It will be appreciated that for compound preparations described herein, when reverse phase HPLC is used to purify a compound, a compound may exist as an acid addition salt. In some embodiments, a compound may exist as a formic acid or mono-, di-, or tri-trifluoroacetic acid salt.

It will further be appreciated that the present invention contemplates individual compounds described herein. Where individual compounds exemplified are isolated and/or characterized as a salt, for example, as a trifluoroacetic acid salt, the present invention contemplates a free base of the salt, as well as other pharmaceutically acceptable salts of the free base.

The following examples contain important additional information, exemplification and guidance that can be adapted to the practice of this invention in its various embodiments and the equivalents thereof

EXAMPLES

As depicted in the Examples below, in certain exemplary embodiments, compounds are prepared according to the following general procedures. It will be appreciated that, although the synthetic methods and Schemes depict the synthesis of certain compounds of the present invention, the following methods and other methods known to one of ordinary skill in the art can be applied to all compounds and subclasses and species of each of these compounds, as described herein.

Unless otherwise noted, all solvents, chemicals, and reagents were obtained commercially and used without purification. The $^1$H NMR spectra were obtained in CDCl$_3$, d$_6$-DMSO, CD$_3$OD, or d$_6$-acetone at 25° C. at 300 MHz on an OXFORD (Varian) with chemical shift (δ, ppm) reported relative to TMS as an internal standard. HPLC-MS chromatograms and spectra were obtained with Shimadzu LC-MS-2020 system. Prep-HPLC instrument were Gilson GX-281 (Gilson) and P230 Preparative Gradient System (Elite). Chiral Prep-HPLC preparation instrument were Elite P230 Preparative Gradient System, Thar Prep-80 and Thar SFC X-5. Microwave instrument were CEM Discover SP. Some chiral analysis and purification were obtained with Yilite P270.

Example 1

Synthesis of N-((2-hydroxy-4,6-dimethylpyridin-3-yl)methyl)-4-(pentan-2-yl)benzamide (Compound I-10)

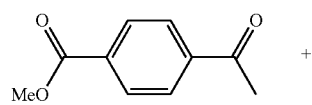

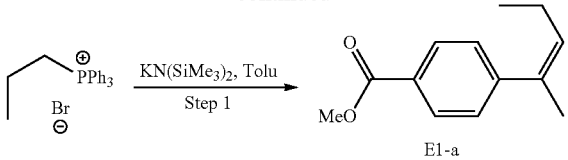

(Z)-methyl-4-(pent-2-en-2-yl)benzoate (E1-a)

To a suspension of triphenyl-(propyl)phosphonium bromide in toluene, a solution of potassium bis(trimethylsilyl)-amide (11.2 mL, 1M in tetrahydrofuran, 11.2 mmol) was added at room temperature. The mixture was stirred at room temperature for about 15 minutes, then a solution of methyl 4-acetylbenzoate in toluene was added to the above mixture. The mixture was refluxed for 1.5 hours. The mixture was washed with water. The organic phase was dried by sodium sulphate. The mixture was filtered. The filtrate was concentrated and the residue was purified by column chromatography (silica gel, petroleum/ethyl acetate=20:1) to give (4-methyl 4-(pent-2-en-2-yl)benzoate (E1-a) (0.76 g, 66%). $^1$H NMR (300 MHz, CDCl$_3$): δ 7.99 (d, J=6.6 Hz, 2H), 7.36 (d, J=6.6 Hz, 2H), 5.51 (t, J=7.8 Hz, 1H), 2.13 (s, 3H), 1.94-1.81 (m, 2H), 1.00 (t, J=6.6 Hz, 3H).

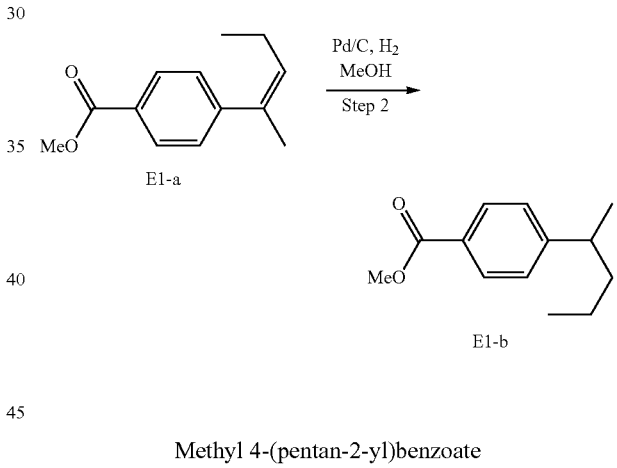

Methyl 4-(pentan-2-yl)benzoate

A mixture of (4-methyl 4-(pent-2-en-2-yl)benzoate (0.76 g, 3.7 mmol), palladium on carbon (592 mg) and methanol (20 mL) was stirred at room temperature for 4 hours under 0.4 MPa of hydrogen gas atmosphere. The mixture was filtered and the filtrate was concentrated to give crude product methyl 4-(pentan-2-yl)benzoate (E1-b) (0.634 g, 84%), which was used in next step without purification. $^1$H NMR (300 MHz, CDCl$_3$): δ 7.99 (d, J=6.6 Hz, 2H), 7.36 (d, J=6.6 Hz, 2H), 3.91 (s, 3H), 2.91-2.76 (m, 1H), 1.58-1.56 (m, 2H), 1.26-1.22 (m, 5H), 0.91 (d, J=6.6 Hz, 3H).

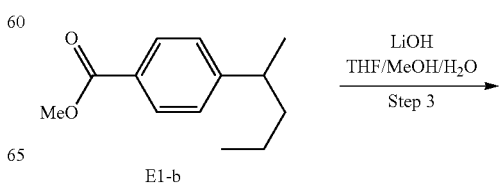

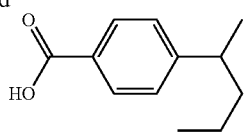

E1-c

4-(pentan-2-yl)benzoic acid

A mixture of methyl 4-(pentan-2-yl)benzoate (634 mg, 3.1 mmol), lithium hydroxide monohydrate (646 mg, 15.4 mmol), tetrahydrofuran (12.0 mL), methanol (4.0 mL) and water (4.0 mL) was stirred at 20° C. for 4 hours. The mixture was acidified to pH=3-4. The mixture was extracted with ethyl acetate (20 ml×3). The organic phase was dried by sodium sulfate. The mixture was filtered. The filtrate was concentrated and the residue was purified by column chromatography (silica gel, petroleum/ethyl acetate=6:1) to gave 4-(pentan-2-yl)benzoic acid (E1-c) as a white solid (487 mg, 82%). LRMS (M−H)$^-$ m/z: 192.12. found 192.

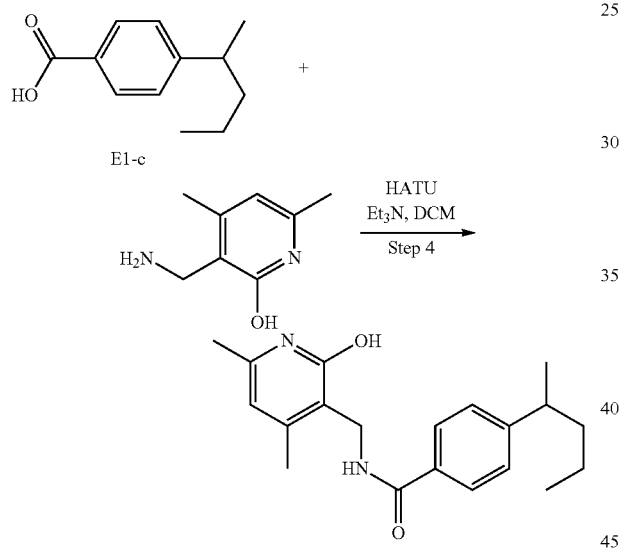

N-((2-hydroxy-4,6-dimethylpyridin-3-yl)methyl)-4-(pentan-2-yl)benzamide (Compound I-10)

A mixture of 4-(pentan-2-yl)benzoic acid (192 mg, 1.0 mmol), 1-(3-dimethylaminopropyl)-3-ethylcarbodiimide hydrochloride (288 mg, 1.5 mmol), 1-hydroxybenzotriazole t (202 mg, 1.5 mmol), triethylamine (0.5 mL) and dichloromethane (15.0 mL) was stirred at 25° C. for half an hour. Then 3-(aminomethyl)-4,6-dimethylpyridin-2-ol (152 mg, 1.0 mmol) was added to the above mixture. The mixture was stirred at 25° C. for 12 hours. The mixture was washed with water (20 ml×2). The organic phase was dried by sodium sulphate. The mixture was filtered. The filtrate was concentrated and the residue was purified by column chromatography (silica gel, dichloromethane/methane=10:1) to give N-((2-hydroxy-4,6-dimethylpyridin-3-yl)methyl)-4-(pentan-2-yl)benzamide as a white solid (100 mg, 40%). LRMS (M+H$^+$) m/z: 326.2. found 326. $^1$H NMR (300 MHz, d$_6$-DMSO): δ 11.46 (s, 1H), 8.26 (t, J=4.5 Hz, 1H), 7.75 (d, J=8.1 Hz, 2H), 7.23 (m, J=8.1 Hz, 2H), 5.85 (s, 1H), 4.29 (d, J=4.5 Hz, 2H), 2.76-2.69 (m, 1H), 2.17 (s, 3H), 2.11 (s, 3H), 1.54-1.47 (m, 2H), 1.18-1.05 (m, 5H), 0.81 (t, J=14.4 Hz, 3H).

Example 2

Synthesis of N-((2-hydroxy-4,6-dimethylpyridin-3-yl)methyl)-4-isopropyl-2-methylbenzamide (Compound I-1)

This synthesis involved 5 steps.

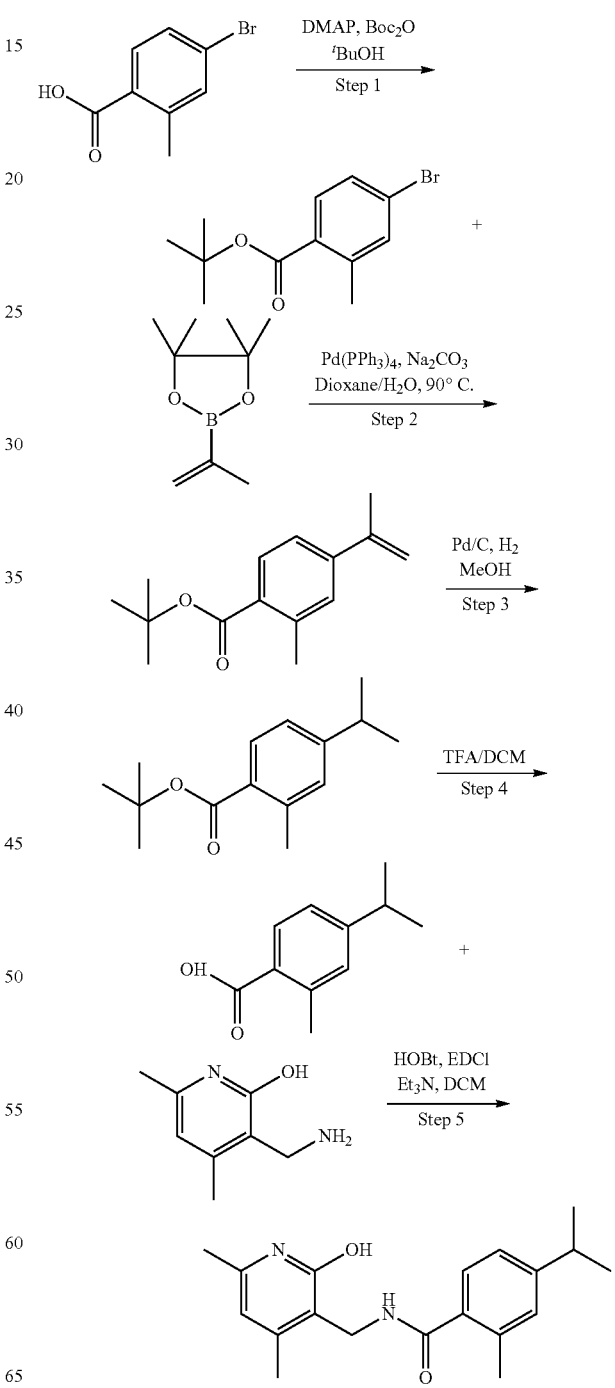

Tert-butyl 4-bromo-2-methylbenzoate

To a solution of 4-bromo-2-methylbenzoic acid (4.52 g, 21.0 mmol) and di-tert-butyl dicarbonate (9.17 g, 42.0 mmol) in 2-methylpropan-2-ol (100 mL) was added 4-dimethylamiopryidine (1.29 g, 10.5 mmol) slowly. The reaction solution was stirred at room temperature for 12 hours. Saturated potassium carbonate water solution was added to the mixture. And the mixture was stirred for 1 hour and extracted with ethyl acetate (60 mL×2). The organic phase was dried over sodium sulfate and filtered. The filtrate was concentrated to give a residue. The residue was purified by column chromatography (silica gel, petroleum ether/ethyl acetate=100:1) to give tert-butyl 4-bromo-2-methylbenzoate (5.5 g, 96%). $^1$H NMR (300 MHz, CDCl$_3$): δ 7.76 (d, J=6.5 Hz, 1H), 7.35 (dd, J$_1$=6.5 Hz, J$_2$=1.8 Hz, 1H), 7.21 (d, J=6.5 Hz, 1H), 2.34 (s, 3H), 1.40 (s, 9H).

Tert-butyl 2-methyl-4-(prop-1-en-2-yl)benzoate

To a solution of tert-butyl 4-bromo-2-methylbenzoate (763 mg, 1.8 mmol), 4,4,5,5-tetramethyl-2-(prop-1-en-2-yl)-1,3,2-dioxaborolane (184 mg, 0.64 mmol) tetrakis(triphenylphosphine)palladium(0) (427 mg, 0.37 mmol) in 1,4-dioxane (16 mL) was added a solution of sodium carbonate (587 mg, 5.5 mmol). The reaction mixture was stirred at 90° C. for 13 hours. The mixture was concentrated. The residue was purified by column chromatography (silica gel, petroleum ether/ethyl acetate=80:1) to give 1-isopropyl-6-(6-(piperazin-1-yl)pyridin-3-yl)-N-(2,2,6,6-tetramethylpiperidin-4-yl)-1H-indazole-4-carboxamide as a colorless oil (375 mg, 57%).

Tert-butyl 4-isopropyl-2-methylbenzoate

A mixture of tert-butyl 3-methyl-4-phenoxybenzoate (150 mg, 0.65 mmol) and wet Pd/C (50 mg, 10%) in methanol (20 mL) was stirred under hydrogen atmosphere (101325 Pa) at room temperature for 12 hours. The reaction mixture was filtered, concentrated and used in next step without purification (100 mg, 65%).

4-isopropyl-2-methylbenzoic acid

A mixture of 3-methyl-4-phenoxybenzoic acid (100 mg, 0.66 mmol) and 2,2,2-trifluoroacetic acid (1 mL) in dichloromethane (4 mL) was stirred at 25° C. for 3 hours. The mixture was washed with water (20 mL×2) and concentrated to give 4-isopropyl-2-methylbenzoic acid (80 mg, 68%). LRMS (M–H$^+$) m/z: 178.10. found 178.

N-((2-hydroxy-4,6-dimethylpyridin-3-yl)methyl)-4-isopropyl-2-methylbenzamide (Compound I-1)

To a solution of 4-isopropyl-2-methylbenzoic acid (80 mg, 0.45 mmol), 1-hydroxybenzotriozole (91 mg, 0.68 mmol), 1-(3-Dimethylaminopropyl)-3-ethylcarbodiimide hydrochloride (130 mg, 0.68 mmol), triethylamine (0.3 mL) in dichloromethane (15 mL) was added 3-(aminomethyl)-4,6-dimethylpyridin-2-ol (69 mg, 0.45 mmol). The reaction mixture was stirred at 20° C. for 13 hours. The mixture was washed with water (20 mL×2). The organic phase was dried over sodium sulfate and filtered. The filtrate was concentrated. The residue was purified by column chromatography (silica gel, dichloromethane/methanol=10:1) to give N-((2-hydroxy-4,6-dimethylpyridin-3-yl)methyl)-4-isopropyl-2-methylbenzamide as a white solid (50 mg, 36%). LRMS (M+H$^+$) m/z: calcd 312.18. found 312. HPLC Purity (214 nm): 99%. $^1$H NMR (300 MHz, d$^6$-DMSO): δ 11.45 (s, 1H), 8.00 (t, J=4.8 Hz, 1H), 7.20-7.06 (m, 3H), 5.85 (s, 1H), 4.25 (d, J=4.8 Hz, 2H), 2.91-2.82 (m, 1H), 2.29 (s, 4H), 2.12 (s, 2H), 2.10 (s, 1H), 1.17 (m, 1H) (d, J=6.9 Hz, 6H).

Example 3

Synthesis of 2-chloro-N-((2-hydroxy-4,6-dimethylpyridin-3-yl)methyl)-4-isopropyl benzamide (Compound I-2)

The synthesis of Compound I-2 involved 5 steps.

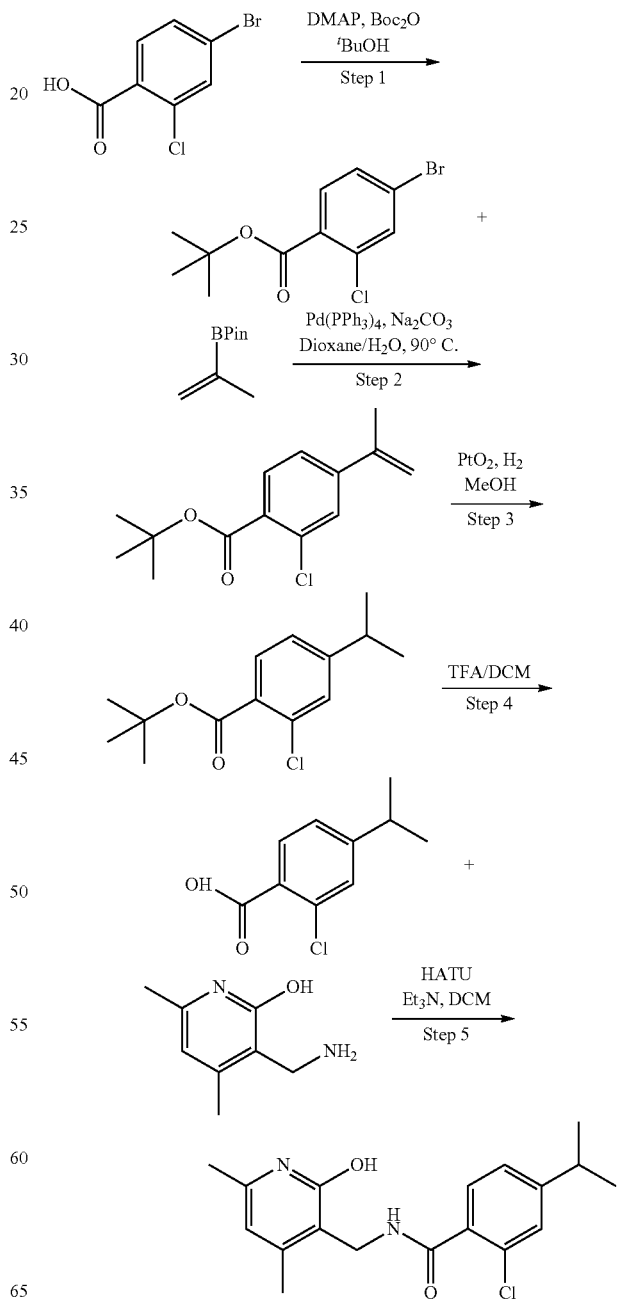

Tert-butyl 4-bromo-2-chlorobenzoate

To a solution of 4-bromo-2-chlorobenzoic acid (5.0 g, 21.2 mmol) in tert-butanol (100 mL) were added di-tert-butyl dicarbonate (13.0 g, 59.6 mmol) and N,N-dimethylpyridin-4-amine (1.5 g, 12.3 mmol). Then the mixture was stirred at room temperature overnight. The solvent was removed under reduced pressure and the residue was purified by column chromatography to give tert-butyl 4-bromo-2-chlorobenzoate (1.8 g, 29.1%) as a yellow oil LRMS (M+H$^+$) m/z: calcd 290.97. found 291.

Tert-butyl 2-chloro-4-(prop-1-en-2-yl)benzoate

To a solution of tert-butyl 4-bromo-2-chlorobenzoate (1.0 g, 3.43 mmol) and 4,4,5,5-tetramethyl-2-(prop-1-en-2-yl)-1,3,2-dioxaborolane (588 mg, 3.50 mmol) in 1,4-dioxane (40 mL) and water (10 mL) were added sodium carbonate (742 mg, 7.0 mmol) and tetrakis(triphenylphosphine)palladium (40 mg, 0.035 mmol). The resultant reaction mixture was stirred at 90° C. overnight under nitrogen atmosphere. After being cooled to room temperature, the reaction mixture was concentrated. The residue was purified by pre-HPLC to get tert-butyl 2-chloro-4-(prop-1-en-2-yl)benzoate (800 mg, 92.3%) as a yellow oil. LRMS (M+H$^+$) m/z: calcd 253.09. found 253.

Tert-butyl 2-chloro-4-isopropylbenzoate

To a solution of tert-butyl 2-chloro-4-(prop-1-en-2-yl)benzoate (200 mg, 0.79 mmol) in methanol (20 mL) was added platinum(IV) oxide (20 mg). The resultant reaction mixture was stirred at room temperature for 24 hours under hydrogen atmosphere. Insoluble matters were removed using celite, and the filtrate was concentrated in vacuo to give tert-butyl 2-chloro-4-isopropylbenzoate (150 mg, 74.4%) as a white solid which was used in the next step directly. LRMS (M+H$^+$) m/z: calcd 255.11. found 255 $^1$H NMR (300 MHz, CD$_3$OD) δ 7.67 (d, J=8.1 Hz, 1H), 7.36 (d, J=1.8 Hz, 1H), 7.28 (dd, J$_1$=8.1 Hz, J$_2$=1.8 Hz, 1H), 2.98 (m, 1H), 1.63 (s, 9H), 1.29 (d, J=6.9 Hz, 6H).

2-chloro-4-isopropylbenzoic acid

To a solution of tert-butyl 2-chloro-4-isopropylbenzoate (150 mg, 0.59 mmol) in dichloromethane (10 mL) was added 2,2,2-trifluoroacetic acid (2 mL) at room temperature. The resultant reaction mixture was stirred at 30° C. for 30 minutes. Thin layer chromatography showed that starting material was consumed completely. The solution was concentrated under reduced pressure to give 2-chloro-4-isopropylbenzoic acid (100 mg, 85.5%) as a white solid which was used in the next step directly. LRMS (M+H$^+$) m/z: calcd 199.04. found 199.

2-chloro-N-((2-hydroxy-4,6-dimethylpyridin-3-yl)methyl)-4-isopropyl benzamide (Compound I-2)

To a solution of 2-chloro-4-isopropylbenzoic acid (100 mg, 0.50 mmol) in dichloromethane (50 mL) were added 2-(7-Aza-1H-benzotriazole-1-yl)-1,1,3,3-tetramethyluronium hexafluorophosphate (190 mg, 0.50 mmol) and triethylamine (175 mg, 1.73 mmol). The resultant reaction mixture was stirred at room temperature for 30 minutes. Then 3-(aminomethyl)-4,6-dimethylpyridin-2-ol (152 mg, 1.0 mmol) was added and the mixture was stirred at ambient temperature overnight. The mixture was washed with brine (50 mL), dried over sodium sulfate, filtered, and concentrated. The residue was purified through pre-HPLC and the obtained solution was freeze-dried to afford 2-chloro-N-((2-hydroxy-4,6-dimethylpyridin-3-yl)methyl)-4-isopropylbenzamide (40 mg, 23.9%) as a white solid. LRMS (M+H$^+$) m/z: calcd 333.13. found 333. HPLC purity (214 nm): 96.2% $^1$H NMR (300 MHz, DMSO) δ 7.37 (d, J=7.8 Hz, 1H), 7.30 (d, J=1.5 Hz, 1H), 7.23 (dd, J$_1$=7.8 Hz, J$_2$=1.5 Hz, 1H), 6.11 (s, 1H), 4.49 (s, 2H), 2.93 (m, 1H), 2.38 (s, 3H), 2.25 (s, 3H), 1.25 (d, J=6.9 Hz, 6H).

Example 4

Synthesis of N-((2-hydroxy-4,6-dimethylpyridin-3-yl)methyl)-4-(2-hydroxypropan-2-yl)benzamide (Compound I-20)

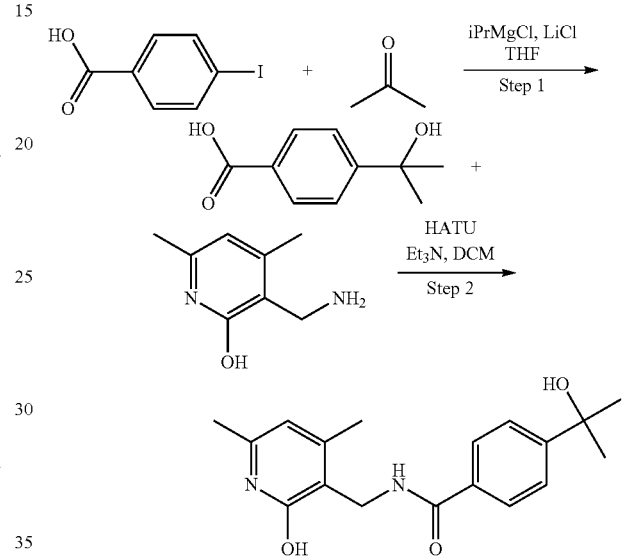

4-(2-hydroxypropan-2-yl)benzoic acid

To a solution of 4-iodobenzoic acid (2.5 g, 10 mmol) in tetrahydrofuran (20 mL) was added lithium chloride (0.42 g, 10 mmol). Then isopropylmagnesium chloride (5 mL, 2 mol/L in tetrahydrofuran) was injected in at –40° C. under nitrogen atmosphere. The reaction mixture was stirred at –40° C. for 1 hour. Then isopropylmagnesium chloride (6 mL, 2 mol/L in tetrahydrofuran) was injected and the reaction was stirred at –40° C. for additional 1 hour. To the solution was added acetone (0.58 g, 10 mmol), and the mixture was stirred at –40° C. for 0.5 hour, then stirred at room temperature for 0.5 hour. After the reaction, the mixture was poured into water (50 mL), hydrochloric acid (3 mol/L) was added to make pH 3-4. and the product was extracted with dichloromethane (50 mL), dried over anhydrous sodium sulfate, concentrated and purified by column chromatography (silica gel dichloromethane:methanol=15:1) to give the pure product 4-(2-hydroxypropan-2-yl)benzoic acid (1.5 g, 83%) as a white solid. $^1$H NMR (CDCl3, 300 MHz) δ: 8.08 (d, J=8.7 Hz, 2H), 7.60 (d, J=8.4 Hz, 2H), 1.61 (s, 6H).

N-((2-hydroxy-4,6-dimethylpyridin-3-yl)methyl)-4-(2-hydroxypropan-2-yl)benzamide (Compound I-20)

To a solution of 4-(2-hydroxypropan-2-yl)benzoic acid (0.09 g, 0.5 mmol) and O-(7-Azabenzotriazol-1-yl)-N,N,N',N'-tetramethyluronium hexafluorophosphate (0.23 g, 0.61 mmol) in dichloromethane (10 mL) was added triethylamine (0.15 g, 1.5 mmol). The reaction mixture was stirred for 15 minutes at room temperature, then 3-(aminomethyl)-4,6- dimethylpyridin-2-ol (0.08 g, 0.53 mmol) was added. The reaction mixture was stirred at room temperature for 12 hours. After the reaction, the mixture was washed with water (20 mL), concentrated and purified by column chromatography (silica gel:dichloromethane:methanol=30:1) to give the pure product (0.11 g, 76%) as a white solid. LRMS (M+H$^+$) m/z: calcd for 314.16. found 314. HPLC Purity (214 nm) 100%. $^1$H NMR (300 MHz, DMSO-d$_6$) δ: 11.47 (s, 1H), 8.28-8.26 (m, 1H), 7.76 (d, J=8.4 Hz, 2H), 7.49 (d, J=8.7 Hz, 2H), 5.86 (s, 1H), 5.08 (s, 1H), 4.29 (d, J=4.8 Hz, 2H), 2.17 (s, 3H), 2.11 (s, 3H), 1.41 (s, 6H).

Example 5

Synthesis of N-((2-hydroxy-4,6-dimethylpyridin-3-yl)methyl)-4-(2-methoxypropan-2-yl)benzamide (Compound I-3)

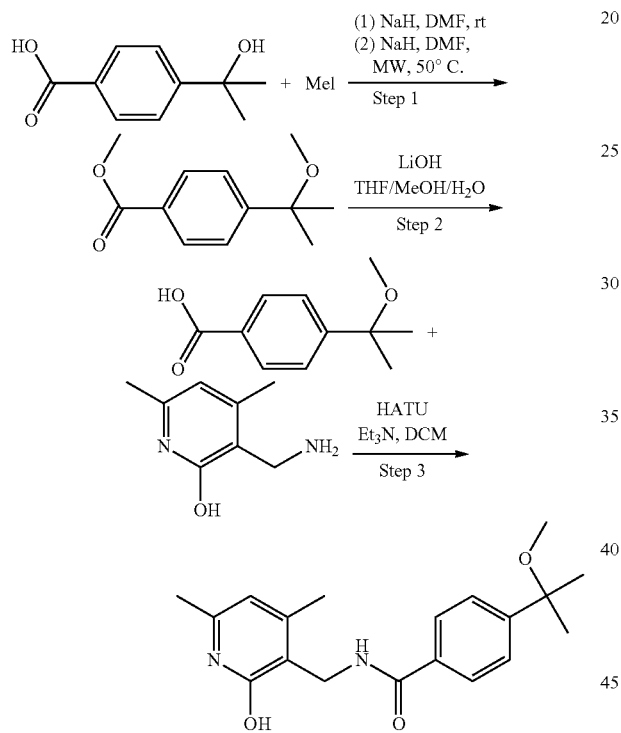

Methyl 4-(2-methoxypropan-2-yl)benzoate

To a solution of 4-(2-hydroxypropan-2-yl)benzoic acid from Example 4 (0.30 g, 1.7 mmol) in anhydrous tetrahydrofuran (10 mL) was added potassium carbonate (0.50 g, 3.6 mmol) and iodomethane (0.40 g, 2.8 mmol). The reaction mixture was stirred at room temperature for 1 hours. Then sodium hydride (0.14 g, 3.5 mmol, 60% in oil) was added at 0° C. The mixture was stirred at room temperature for 15 minutes. then iodomethane (0.47 g, 3.3 mmol) was added, and the mixture was reacted under microwave for 15 minutes. After the reaction, the mixture was poured to water (50 mL), and the product was extracted with ethyl acetate (50 mL), washed with water (50 mL). dried over anhydrous sodium sulfate, the solvent was removed in vacuo to give the pure product methyl 4-(2-methoxypropan-2-yl)benzoate (0.21 g, 60%) as the yellow oil. $^1$H NMR (300 MHz, CD3OD): δ 7.99 (d, J=8.7 Hz, 2H), 7.52 (d, J=8.4 Hz, 2H), 3.89 (s, 3H), 3.08 (s, 3H), 1.52 (s, 6H).

4-(2-methoxypropan-2-yl)benzoic acid

Lithium hydroxide hydrate (0.40 g, 9.6 mmol) was added to a solution of methyl 4-(2-methoxypropan-2-yl)benzoate (0.10 g, 0.48 mmol) in tetrahydrofuran (9 mL), methanol (3 mL) and water (3 mL). The reaction mixture was stirred at room temperature for 2 hours. After the reaction, the solvent was removed in vacuo. Hydrochloric acid (3 mol/L) was added to make pH 2-3, and the product was extracted with dichloromethane (50 mL). The combined organic phase was washed with sodium chloride aqueous solution (50 mL×3), dried over anhydrous sodium sulfate, and the solvent was evaporated to dryness to give pure product 4-(2-methoxypropan-2-yl)benzoic acid (0.09 g, 96%) as a white solid.

N-((2-hydroxy-4,6-dimethylpyridin-3-yl)methyl)-4-(2-methoxypropan-2-yl)benzamide (Compound I-3)

To a solution of 4-(2-methoxypropan-2-yl)benzoic acid (0.09 g, 0.46 mmol) and O-(7-Azabenzotriazol-1-yl)-N,N,N',N'-tetramethyluronium hexafluorophosphate (0.23 g, 0.61 mmol) in dichloromethane (10 mL) was added triethylamine (0.15 g, 1.5 mmol). The reaction mixture was stirred for 15 minutes at room temperature, then 3-(aminomethyl)-4,6-dimethylpyridin-2-ol (0.08 g, 0.53 mmol) was added. The reaction mixture was stirred at room temperature for 12 hours. After the reaction, the mixture was washed with water (20 mL), concentrated and purified by column chromatography (silica gel:dichloromethane:methanol=30:1) to give pure product N-((2-hydroxy-4,6-dimethylpyridin-3-yl)methyl)-4-(2-methoxypropan-2-yl)benzamide (0.09 g, 61%) as a white solid. LRMS (M+H$^+$) m/z: calcd for 328.18. found 328. HPLC Purity (214 nm) 99.8%. $^1$H NMR (300 MHz, DMSO-d$_6$) δ: 11.47 (s, 1H), 8.32 (d, J=1.5 Hz, 1H), 7.81 (d, J=8.1 Hz, 2H), 7.43 (d, J=8.4 Hz, 2H), 5.86 (s, 1H), 4.30 (d, J=4.8 Hz, 2H), 2.97 (s, 3H), 2.17 (s, 3H), 2.11 (s, 3H), 1.44 (s, 6H).

Example 6

Synthesis of N-((2-hydroxy-4,6-dimethylpyridin-3-yl)methyl)-4-(1-methoxy ethyl)benzamide (Compound I-4)

This synthesis involved three steps.

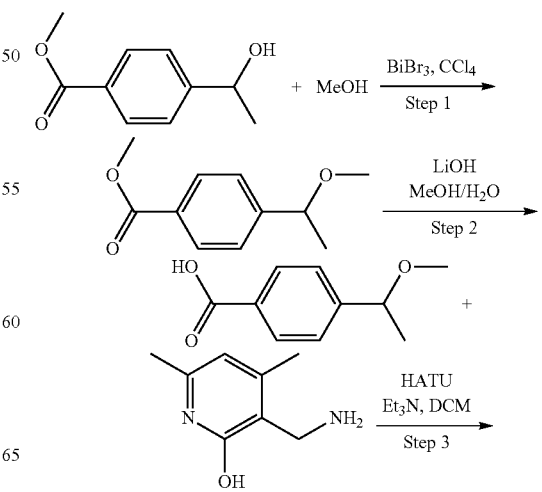

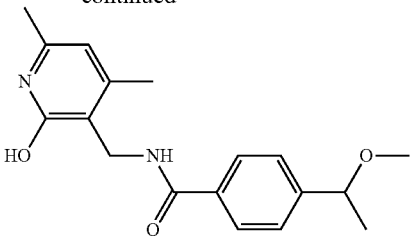

Methyl 4-(1-methoxyethyl)benzoate

To the solution of methanol (53 mg, 1.67 mmol) in perchloromethane (80 mL) was added bismuth (III) bromide (743 mg, 1.67 mmol), the mixture was stirred for 30 minutes at room temperature, the methyl 4-(1-hydroxyethyl)benzoate (300 mg, 1.67 mmol) was added, the mixture was stirred at room temperature for 12 hours. Then the mixture was concentrated and purified by column chromatography (silica gel, Petroleum ether/ethyl acetate=20:1) to give methyl-4-(1-methoxyethyl)benzoate (185 mg, 57%), as oil.

4-(1-ethoxyethyl)benzoic acid

To the solution of methyl 4-(1-methoxyethyl)benzoate (181 mg, 0.95 mmol) in methanol and water (50 mL/10 mL) was added lithium hydroxide (50 mg, 2.1 mmol), the solution was stirred at room temperature for 12 hours. Then the solution was acidified by hydrogen chloride (1 N/mol) pH to 6, extracted with dichloromethane (50 mL*3), evaporated the solvent to give 4-(1-ethoxyethyl)benzoic acid (166 mg, 97%).

N-((2-hydroxy-4,6-dimethylpyridin-3-yl)methyl)-4-(1-methoxyethyl)benzamide (Compound I-4)

To the solution of 4-(1-ethoxyethyl)benzoic acid (162 mg, 0.9 mmol) in dichloromethane (80 mL) was added o-(7-Azabenzotriazol-1-yl)-N,N,N',N'-tetramethyluronium hexafluorophosphate (513 mg, 1.35 mmol) and triethylamine (273 mg, 2.7 mmol). then the 3-(aminomethyl)-4,6-dimethyl pyridine-2-ol (137 mg, 0.9 mmol) was added, the solution was stirred at room temperature, water (80 mL) was added and washed 3 times, the organic layer was evaporated and purified by column chromatography (silica gel, dichloromethane/methanol=20:1) to give N-((2-hydroxy-4,6-dimethylpyridin-3-yl)methyl)-4-(1-methoxyethyl)benzamide (66 mg, 23%). LRMS (M+H$^+$) m/z: calcd: 314.16. found 314; $^1$H-NMR (300 MHz, CD$_3$OD)$^1$H-NMR (300 MHz, CD$_3$OD) δ 1.379 (d, 3H), 2.241 (s, 3H), 2.368 (s, 3H), 3.207 (s, 3H), 4.368-4.389 (m, 1H), 4.497 (s, 2H), 6.110 (s, 1H), 7.377 (d, J=8.4 Hz, 2H), 7.779 (d, J=8.4 Hz, 2H).

Example 7

Synthesis of N-((2-hydroxy-4,6-dimethylpyridin-3-yl)methyl)-4-(1-isopropoxyethyl)benzamide (Compound I-5)

This synthesis involved 3 steps.

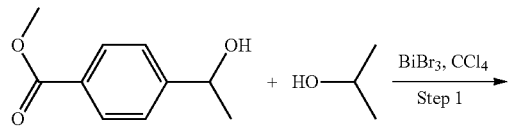

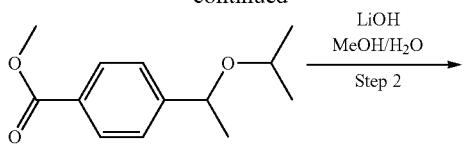

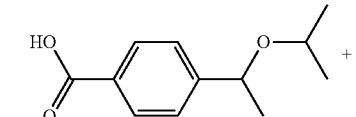

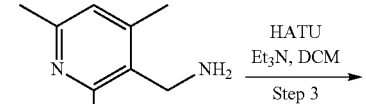

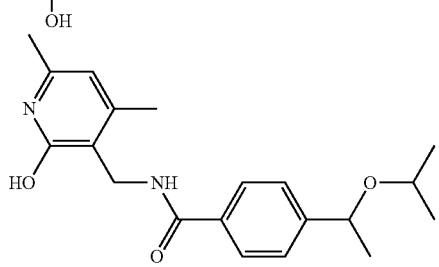

Methyl 4-(1-isopropoxyethyl)benzoate

To the solution of propan-2-ol (100 mg, 1.67 mmol) in perchloromethane (80 mL) was added bismuth(III) bromide (743 mg, 1.67 mmol), the mixture was stirred for 30 minutes at room temperature, then methyl 4-(1-hydroxyethyl)benzoate (300 mg, 1.67 mmol) was added to the solution, the mixture was stirred at room temperature for 12 hours. Then the mixture was concentrated and purified by column chromatography (silica gel, Petroleum ether/ethyl acetate=20:1) to give methyl4-(1-isopropoxyethyl)benzoate (161 mg, 43%) as oil. $^1$H-NMR (300 MHz, CD$_3$OD) δ 7.96 (d, J=8.4 Hz, 2H), 7.41 (d, J=8.4 Hz, 2H), 4.68-4.61 (m, 1H), 3.54-3.46 (m, 1H), 1.38 (d, 3H), 1.15 (d, 3H), 1.06 (d, 3H), 4-(1-isopropoxyethyl)benzoic acid To the solution of methyl 4-(1-isopropoxyethyl)benzoate (161 mg, 0.73 mol) in methanol and water (50 mL/10 mL) was added lithium hydroxide (50 mg, 2.1 mmol), the solution was stirred at room temperature for 12 hours. Then the solution was acidified by hydrogen chloride (1 N/mol) pH to 6, extracted with dichloromethane (50 mL*3), evaporated the solvent to give 4-(1-isopropoxyethyl)benzoic acid (137 mg, 90%)

N-((2-hydroxy-4,6-dimethylpyridin-3-yl)methyl)-4-(1-isopropoxyethyl)benzamide (Compound I-5)

To the solution of 4-(1-isopropoxyethyl)benzoic acid (137 mg, 0.66 mmol) in dichloromethane (80 mL) was added o-(7-Azabenzotriazol-1-yl)-N,N,N',N'-tetramethyluronium hexafluorophosphate (380 mg, 1 mmol) and triethylamine (200 mg, 2 mmol). then the 3-(aminomethyl)-4,6-di methylpyridin-2-ol (100 mg, 0.66 mmol) was added, the solution was stirred at room temperature for 12 hours, water (80 mL) was added and washed 3 times, the organic layer was evaporated and purified by column chromatography (silica gel, dichloromethane/methanol=20:1) to give N-((2-hydroxy-4,6-dimethylpyridin-3-yl)methyl)-4-(1-isopropoxyethyl)benzamide (57 mg, 91%) LRMS (M+H⁺) m/z: calcd: 342.19. found 342; ¹H-NMR (300 MHz, CD₃OD)¹H-NMR (300 MHz, CD₃OD) δ 7.77 (d, J=8.4 Hz, 2H), 7.40 (d, J=8.4 Hz, 2H), 6.10 (m, 1H), 4.64-4.62 (m, 1H), 4.49 (s, 2H), 3.52-3.48 (m, 1H), 2.36 (s, 3H), 2.24 (s, 3H), 1.36 (d, J=6.3 Hz, 3H), 1.15 (d, J=6 Hz, 3H), 1.06 (d, J=6 Hz, 3H).

Example 8

Synthesis of 4-(1-ethoxyethyl)-N-((2-hydroxy-4,6-dimethylpyridin-3-yl)methyl)benzamide (Compound I-7)

This synthesis involved the steps.

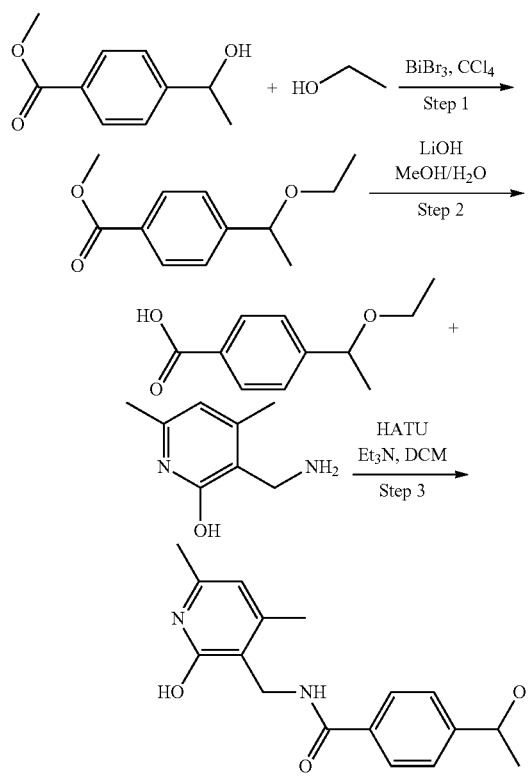

Methyl 4-(1-ethoxyethyl)benzoate

To the solution of ethanol (77 mg, 1.67 mmol) in perchloromethane (80 mL) was added bismuth(III) bromide (743 mg, 1.67 mmol), the mixture was stirred for 30 minutes at room temperature, the methyl 4-(1-hydroxyethyl)benzoate (300 mg, 1.67 mmol) was added, the mixture was stirred at room temperature for 12 hours. Then the mixture was concentrated and purified by column chromatography (silica gel, Petroleum ether/ethyl acetate=20:1) to give methyl 4-(1-ethoxyethyl)benzoate (191 mg, 55%) as oil.

4-(1-ethoxyethyl)benzoic acid

To the solution of methyl 4-(1-ethoxyethyl)benzoate (191 mg, 0.92 mmol) in methanol and water (50 mL/10 mL) was added lithium hydroxide (100 mg, 4.2 mmol), the solution was stirred at room temperature for 12 hours. Then the solution was acidified by hydrogen chloride (1 N/mol) pH to 6, extracted with dichloromethane (80 mL*3), evaporated the solvent to give 4-(1-ethoxyethyl)benzoic acid (167 mg, 93%).

4-(1-ethoxyethyl)-N-((2-hydroxy-4,6-dimethylpyridin-3-yl)methyl)benzamide (Compound I-7)

To the solution of 4-(1-ethoxyethyl)benzoic acid (167 mg, 0.86 mmol) in dichloromethane (80 mL) was added o-(7-Azabenzotriazol-1-yl)-N,N,N',N'-tetramethyluronium hexafluorophosphate (490 mg, 1.3 mmol) and triethylamine (260 mg, 2.6 mmol). then the 3-(aminomethyl)-4,6-dimethylpyridin-2-ol (131 mg, 0.86 mmol) was added, the solution was stirred at room temperature for 12 hours, water was added and washed 3 times, the organic layer was evaporated and purified by column chromatography (silica gel, dichloromethane/methanol=20:1) to give 4-(1-ethoxyethyl)-N-((2-hydroxy-4,6-dimethylpyridin-3-yl)methyl)benzamide (67 mg, 24%). LRMS (M+H⁺) m/z: calcd: 390.19. found 390. ¹H-NMR (300 MHz, CD₃OD) δ 7.73 (d, J=8.4 Hz, 2H), 7.31 (d, J=8.4 Hz, 2H), 5.96 (s, 1H), 4.58 (d, 2H), 4.43-4.41 (m, 1H), 3.35-3.31 (m, 1H), 2.39 (s, 3H), 2.28 (s, 3H), 1.42-1.40 (d, J=6.6 Hz, 3H), 1.176 (m, 3H).

Example 9

Synthesis of N-((2-hydroxy-4,6-dimethylpyridin-3-yl)methyl)-4-(1-isobutoxyethyl)benzamide (Compound I-8)

This synthesis involved three steps.

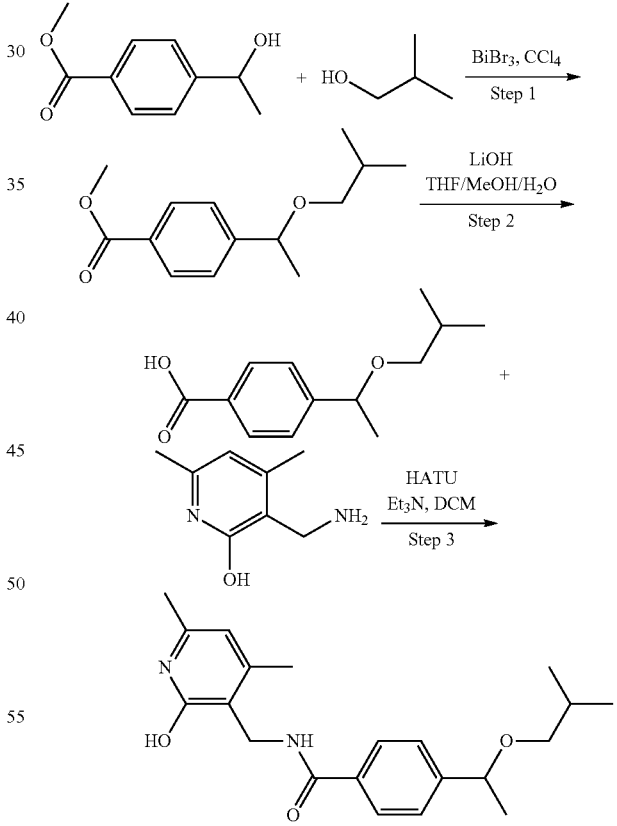

Methyl 4-(1-isobutoxyethyl)benzoate

To a solution of 2-methylpropan-1-ol (150 mg, 2 mmol) in perchloromethane (4 mL) was added bismuth(III) bromide (900 mg, 2 mmol). The mixture was stirred at room temperature for 30 minutes then methyl 4-(1-hydroxyethyl)benzoate (180 mg, 1 mmol) was added and the mixture was stirred at room temperature for 12 hours. The suspension was concentrated in vacuum and quenched with aqueous 1N hydrochloric acid (5 mL). The residue was taken up with water (50 mL) and extracted with dichloromethane (50 mL). The combined extract was dried over sodium sulphate, evaporated and purified by column chromatography (silica gel, petroleum ether/ethyl acetate=20:1) to give the product methyl 4-(1-isobutoxyethyl)benzoate (0.18 g, 76%) as colorless oil. $^1$H NMR (300 MHz, CD$_3$OD) δ 8.01 (d, J=8.1 Hz, 2H), 7.36 (d, J=8.1 Hz, 2H), 4.44-4.41 (m, 1H), 3.12-3.00 (m, 2H), 1.87-1.82 (m, 1H), 1.44 (d, J=6.3 Hz, 3H), 0.88 (d, J=6.6 Hz, 6H).

4-(1-isobutoxyethyl)benzoic acid

To a solution of methyl 4-(1-isobutoxyethyl)benzoate (180 mg, 0.76 mmol) in tetrahydrofuran:methanol:water=3:1:1 (4 mL) was added lithium hydroxide (100 mg, 2.4 mmol). The mixture was stirred at room temperature for 2 hours. The suspension was concentrated in vacuum and quenched with aqueous 1N hydrochloric acid (5 mL). The residue was taken up with water (50 mL) and extracted with dichloromethane (50 mL). The combined extract was dried over sodium sulphate, evaporated and purified by column chromatography (silica gel, dichloromethane/methanol=20:1) to give the product 4-(1-isobutoxyethyl)benzoic acid (132 mg, 78%) as pale solid.

N-((2-hydroxy-4,6-dimethylpyridin-3-yl)methyl)-4-(1-isobutoxyethyl)benzamide Compound I-8

A solution of 4-(1-isobutoxyethyl)benzoic acid (132 mg, 0.59 mmol) in dichloromethane (50 mL) was added 2-(7-aza-1H-benzotriazole-1-yl)-1,1,3,3-tetramethyluronium hexafluorophosphate (35 mg, 0.5 mmol), triethylamine (32 mg, 0.7 mmol), stirred for 30 minutes. Then 3-(aminomethyl)-4,6-dimethylpyridin-2-ol (27 mg, 0.4 mmol) was added and the mixture was stirred at room temperature for 12 hours. The mixture was washed with water (50 mL), dried over sodium sulphate, concentrated. The residue was purified through column chromatography (silica gel, dichloromethane/methanol=20:1) to give the product N-((2-hydroxy-4,6-dimethylpyridin-3-yl)methyl)-4-(1-isobutoxyethyl)benzamide (83 mg, 40%) as white solid. LRMS (M+H$^+$) m/z: calcd 356.13. found 356. HPLC Purity (214 nm): 97%. $^1$H NMR (300 MHz, CD$_3$OD) δ 7.76 (d, J=8.1 Hz, 2H), 7.38 (d, J=8.1 Hz, 2H), 6.10 (s, 1H), 4.49-4.43 (m, 3H), 3.14-3.00 (m, 2H), 2.37 (s, 3H), 2.24 (s, 3H), 1.84-1.79 (m, 2H), 1.39 (d, J=6.3 Hz, 3H), 0.88 (d, J=6.6 Hz, 6H).

Example 10

Synthesis of N-((2-hydroxy-4,6-dimethylpyridin-3-yl)methyl)-4-(3-methylbutan-2-yl)benzamide (Compound I-9)

This synthesis involved four steps.

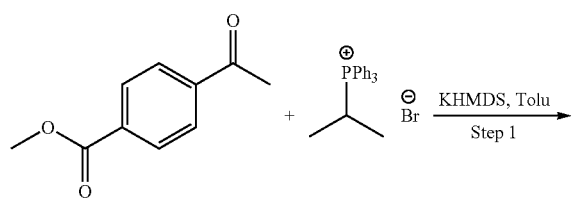

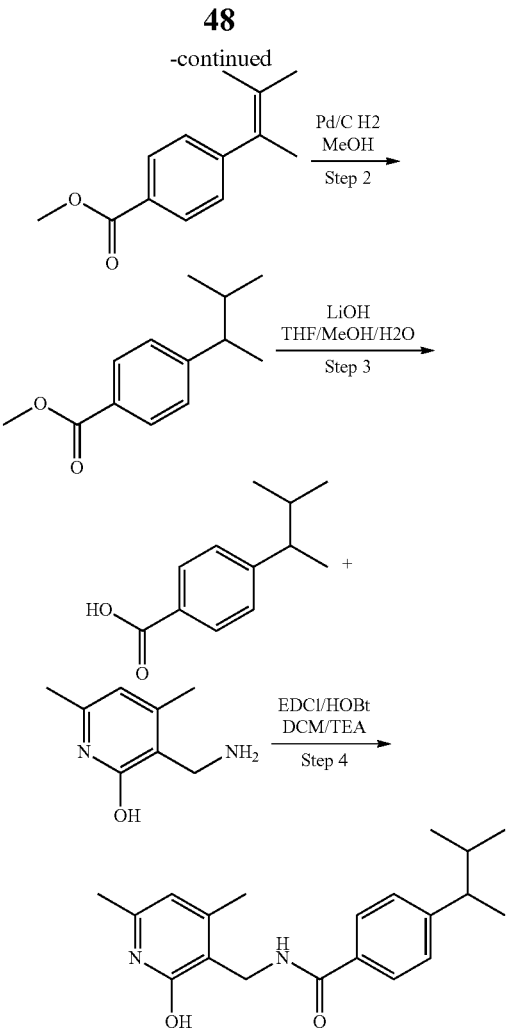

Methyl 4-(3-methylbut-2-en-2-yl)benzoate

To a suspension of isopropyltriphenylphosphonium bromide (2.59 g, 6.0 mmol) in toluene (10 mL) under nitrogen at room temperature was added potassium hexamethyldisilazide (1.2 g, 6.0 mmol), and the red solution was stirred for 10 minutes. A solution of methyl 4-acetylbenzoate (0.53 g, 3.0 mmol) in toluene (5 mL) was added, and the red solution was heated to reflux. The mixture was stirred for 2 hours. after the reaction, it was allowed to cool to room temperature, and the mixture was diluted with ethyl acetate (100 mL), washed with water (100 mL), dried over anhydrous sodium sulfate, concentrated and purified by column chromatography (silica gel:petroleum ether:ethyl acetate=20:1) to give pure product methyl 4-(3-methylbut-2-en-2-yl)benzoate (0.51 g, 83%) as a colorless oil. $^1$H NMR (300 MHz, CDCl3): δ 7.98 (d, J=8.4 Hz, 2H), 7.20 (d, J=8.4 Hz, 2H), 3.92 (s, 3H), 1.97 (s, 3H), 1.83 (s, 3H), 1.60 (s, 3H).

Methyl 4-(3-methylbutan-2-yl)benzoate

To a solution methyl 4-(3-methylbut-2-en-2-yl)benzoate (0.2 g, 1.0 mmol) in methanol (30 mL) was added Pd/C (0.50 g). The reaction mixture was stirred at room temperature for 3 hour at 4 atm of hydrogen, after the reaction, it was filtered, and the filtrate was removed in vacuo to give pure product methyl 4-(3-methylbutan-2-yl)benzoate (0.20 g, 100%) as the colorless oil.

4-(3-methylbutan-2-yl)benzoic acid

Lithium hydroxide hydrate (0.42 g, 10 mmol) was added to a solution methyl 4-(3-methylbutan-2-yl)benzoate (0.20 g, 1.0 mmol) in tetrahydrofuran (9 mL), methanol (3 mL) and water (3 mL). The reaction mixture was stirred at room temperature for 3 hours. After the reaction, the solvent was removed in vacuo. Hydrochloric acid (3 mol/L) was added to make pH 1-2, and the product was extracted with dichloromethane (50 mL). The combined organic phase was washed with sodium chloride aqueous solution (20 mL×3), dried over anhydrous sodium sulfate, and the solvent was evaporated to dryness to give pure product 4-(3-methylbutan-2-yl)benzoic acid (0.18 g, 94%) as a white solid.

N-((2-hydroxy-4,6-dimethylpyridin-3-yl)methyl)-4-(3-methylbutan-2-yl)benzamide (Compound I-9)

To a solution of 4-(3-methylbutan-2-yl)benzoic acid (0.10 g, 0.50 mmol), 1-Ethyl-(3-dimethylaminopropyl)carbodiimide hydrochloride (0.14 g, 0.7 mmol) and 1-hydroxybenzotriazole (0.10 g, 0.70 mmol) in dichloromethane (20 mL) was added triethylamine (0.2 g, 2.0 mmol). The reaction mixture was stirred at room temperature for 15 minutes, and followed by 3-(aminomethyl)-4,6-dimethylpyridin-2-ol (0.08 g, 0.5 mmol). The reaction mixture was stirred at room temperature for 12 hours. After the reaction, the mixture was washed with water, dried by anhydrous sodium sulfate, then the solvent removed in vacuo to give the crude product, which was purified by Prep-TLC (dichloromethane:methanol=20:1) to give the pure product N-((2-hydroxy-4,6-dimethylpyridin-3-yl)methyl)-4-(3-methylbutan-2-yl)benzamide (0.08 g, 44%) as a white solid. LR MS (M+H$^+$): calcd for 326.2. found 326. HPLC Purity (214 nm) 99.6%. $^1$H NMR (CH3OH-d$_4$, 300 MHz): δ 7.71 (d, J=8.1 Hz, 2H), 7.23 (d, J=8.4 Hz, 2H), 6.10 (s, 1H), 4.49 (s, 2H), 2.49-2.44 (m, 1H), 2.37 (s, 3H), 2.24 (s, 3H), 1.82-1.75 (m, 1H), 3.14-3.06 (m, 1H), 1.24 (d, J=7.2 Hz, 3H), 0.96 (d, J=6.6 Hz, 3H), 0.76 (d, J=7.2 Hz, 3H).

Example 11

Synthesis of N-((2-hydroxy-4,6-dimethylpyridin-3-yl)methyl)-4-isopropyl-3-phenoxy benzamide (Compound I-11)

This synthesis involved 6 steps.

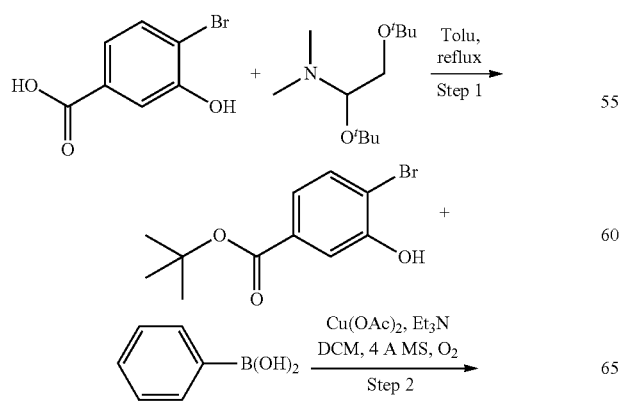

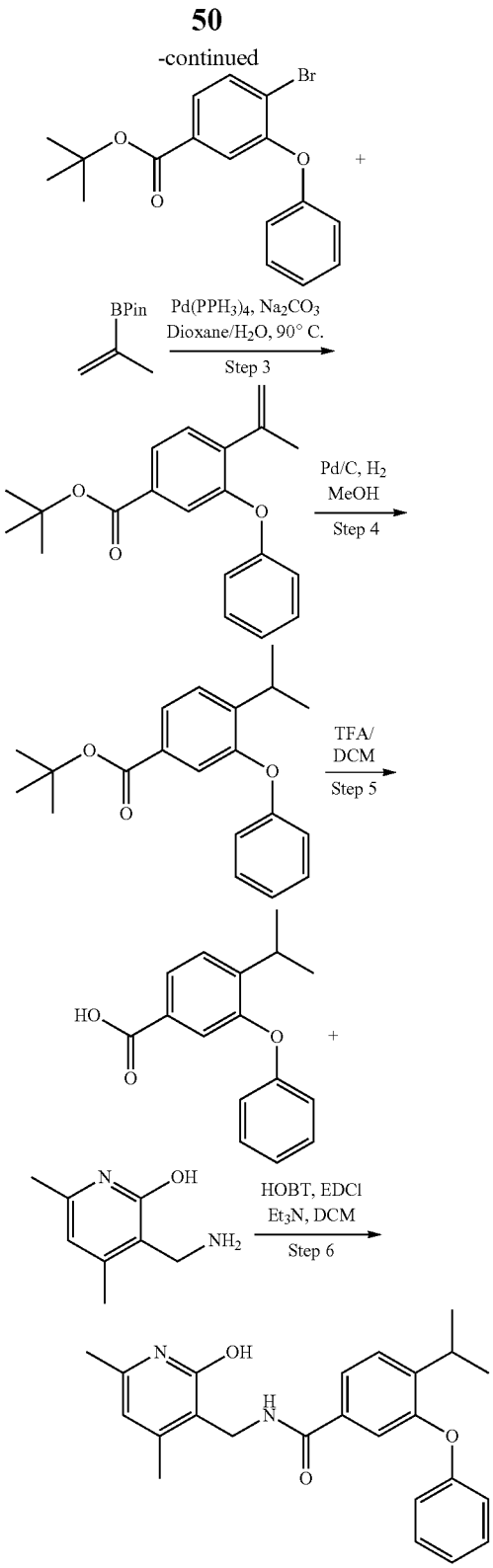

Tert-butyl 4-bromo-3-hydroxybenzoate

To a solution of 4-bromo-3-hydroxybenzoic acid (1.0 g, 4.6 mmol) in toluene (100 mL) was added di-tert-butoxy-N,N-dimethylmethanamine (935 mg, 4.6 mmol). Then the mixture was stirred at 85° C. overnight. The reaction mixture was poured into water (50 mL) and ethyl acetate (50 mL), the organic phase was washed with water (30 mL), dried over anhydrous sodium sulfate, evaporated and purified by column chromatography to give tert-butyl 4-bromo-3-hydroxybenzoate (1.0 g, 79.4%) as a white solid. LRMS (M+H$^+$) m/z: calcd 273.00. found 273.

Tert-butyl 4-bromo-3-phenoxybenzoate

A flask was charged with phenylboronic acid (520 mg, 4.26 mmol), copper acetate (383 mg, 2.11 mmol), tert-butyl 4-bromo-3-hydroxybenzoate (700 mg, 2.56 mmol), and powdered 4 Å molecular sieves. The reaction mixture was diluted with dichloromethane to yield a solution approximately 0.1 M in phenylboronic acid, and triethylamine was added. After stiffing the colored heterogeneous reaction mixture was stirred for 18 hours at 25 under oxygen atmosphere. The crude reaction mixture was filtered through a plug of celite to remove the molecular sieves and any insoluble byproducts, and then concentrated in vacuo to afford the crude product tert-butyl 4-bromo-3-phenoxybenzoate (478 mg, 53.5%). LRMS (M+H$^+$) m/z: calcd 349.04. found 349. $^1$H NMR (300 MHz, DMSO) δ 7.76 (m, 1H), 7.62 (m, 1H), 7.35 (m, 2H), 7.15 (m, 1H), 6.96 (m, 3H), 1.53 (s, 9H).

Tert-butyl 3-phenoxy-4-(prop-1-en-2-yl)benzoate

A mixture of tert-butyl 4-bromo-3-phenoxybenzoate (400 mg, 1.15 mmol), 4,4,5,5-tetramethyl-2-(prop-1-en-2-yl)-1,3,2-dioxaborolane (193 mg, 1.15 mmol) and sodium carbonate (366 mg, 3.45 mmol), tetrakis(triphenylphosphine)palladium (40 mg, 0.035 mmol) in 1,4-dioxane (8 mL) and water (2 mL) was stirred at 90° C. overnight under nitrogen atmosphere. After being cooled to room temperature, the reaction was concentrated. The residue was purified by pre-HPLC to get tert-butyl 3-phenoxy-4-(prop-1-en-2-yl)benzoate (309 mg, 87%) as a yellow solid LRMS (M+H$^+$) m/z: calcd 311.16. found 311.

Tert-butyl 4-isopropyl-3-phenoxybenzoate

To a solution of tert-butyl 3-phenoxy-4-(prop-1-en-2-yl) benzoate (200 mg, 0.64 mmol) in methanol (20 mL) was added palladium loaded on activated carbon (20 mg) and the mixture was stirred for 24 hours at room temperature under hydrogen atmosphere. Insoluble matters were removed using celite, and the filtrate was concentrated in vacuo to give tert-butyl-4-isopropyl-3-phenoxy benzoate (150 mg, 74.5%) as a white solid. LRMS (M+H$^+$) m/z: calcd 313.17. found 313. $^1$H NMR (300 MHz, DMSO) δ 7.72 (m, 1H), 7.69 (m, 1H), 7.11 (m, 2H), 6.97 (m, 2H), 6.96 (m, 2H), 3.34 (m, 1H), 1.53 (s, 9H), 1.26 (d, J=6 Hz, 6H).

4-isopropyl-3-phenoxybenzoic acid

To a solution of tert-butyl 4-isopropyl-3-phenoxybenzoate (150 mg, 0.48 mmol) in dichloromethane (10 mL) was added 2,2,2-trifluoroacetic acid (2 mL). The resultant mixture was stirred at room temperature for 30 minutes. Thin layer chromatography showed that starting material was consumed completely. The solution was concentrated to give 4-isopropyl-3-phenoxybenzoic acid (100 mg, 81.3%) as a white solid which was used in the next step directly. LRMS (M+H$^+$) m/z: calcd 257.11. found 257. $^1$H NMR (300 MHz, DMSO) δ 12.94 (s, 1H), 7.71 (m, 1H), 7.68 (m, 1H), 7.40 (m, 2H), 7.38 (s, 1H), 7.36 (m, 1H), 7.11 (m, 2H), 1.22 (s, 6H).

N-((2-hydroxy-4,6-dimethylpyridin-3-yl)methyl)-4-isopropyl-3-phenoxy benzamide (Compound I-11)

To a solution of 4-isopropyl-3-phenoxybenzoic acid (100 mg, 0.39 mmol) in dichloromethane (20 mL) were added N-ethyl-N'-(3-dimethylaminopropyl)carbodiimide hydrochloride (96 mg, 0.50 mmol), N-hydroxy benzotriazole (68 mg, 0.50 mmol) and triethylamine (175 mg, 1.73 mmol). The resultant reaction mixture was stirred for 30 minutes. Then 3-(aminomethyl)-4,6-dimethylpyridin-2-ol (61 mg, 0.40 mmol) was added and the mixture was stirred at room temperature overnight. The mixture was washed with brine (20 mL), dried over sodium sulfate, filtered, and concentrated. The residue was purified through pre-HPLC and the obtained solution was freeze-dried to afford N-((2-hydroxy-4,6-dimethylpyridin-3-yl)methyl)-4-isopropyl-3-phenoxy benzamide (50 mg, 32.8%) as a white solid. LRMS (M+H$^+$) m/z: calcd 391.19. found 391 HPLC purity (214 nm): 90.4%. $^1$H NMR (300 MHz, DMSO) δ 7.58 (m, 1H), 7.55 (m, 1H), 7.33 (m, 3H), 7.07 (m, 1H), 6.89 (m, 2H), 6.07 (s, 1H), 4.44 (s, 2H), 3.31 (m, 1H), 2.32 (s, 3H), 2.22 (s, 3H), 1.24 (d, J=9 Hz, 6H).

Example 12

Synthesis of N-((2-hydroxy-4,6-dimethylpyridin-3-yl)methyl)-3-methyl-2,3-dihydrobenzofuran-6-carboxamide (Compound I-19)

This synthesis involved seven steps.

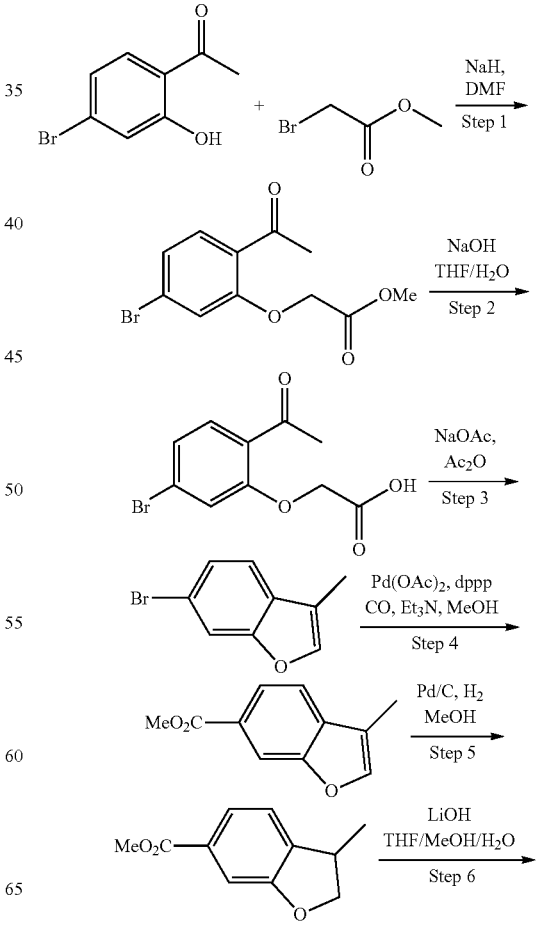

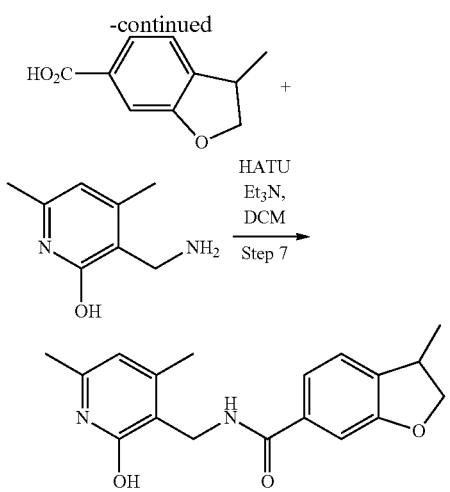

Methyl 2-(2-acetyl-5-bromophenoxy)acetate

A solution of 1-(4-bromo-2-hydroxyphenyl)ethanone (1.06 g, 5 mmol) in dry N,N-dimethylformamide (10 mL) was charged with sodium hydride (240 mg, 10 mmol) and the mixture was stirred at room temperature for 30 minutes, then methyl 2-bromoacetate (0.84 g, 5.5 mmol) was added and the mixture was stirred at room temperature for 12 hours. After completed (40 mL) of methanol was added followed by concentrating under vacuum to give methyl 2-(2-acetyl-5-bromophenoxy)acetate (1.38 g, 90%) as colorless oil. $^1$H NMR (300 MHz, CD$_3$OD) δ 8.01 (s, 1H), 7.65 (d, J=8.1 Hz, 1H), 7.18 (d, J=8.1 Hz, 1H), 6.97 (s, 1H), 4.73 (s, 2H), 3.81 (s, 3H), 2.69 (s, 3H).

2-(2-acetyl-5-bromophenoxy)acetic acid

To a solution of methyl 2-(2-acetyl-5-bromophenoxy)acetate (1.35 g, 4.5 mmol) in tetrahydrofuran:water=3:1 (20 mL) was added sodium hydroxide (400 mg, 10 mmol). The mixture was stirred at room temperature for 2 hours. The suspension was concentrated in vacuum and quenched with aqueous 1N hydrochloric acid (5 mL). The residue was taken up with water (50 mL) and extracted with dichloromethane (50 mL). The combined extract was dried over sodium sulphate, evaporated and purified by column chromatography (silica gel, dichloromethane/methanol=20:1) to give the product 2-(2-acetyl-5-bromophenoxy)acetic acid (1.14 g, 91%) as pale solid.

6-bromo-3-methylbenzofuran

A 100 mL flask equipped with a magnetic stirbar, condenser, is charged with 2-(2-acetyl-5-bromophenoxy)acetic acid (1.14 g, 4.0 mmol) and (40 mL) of acetic anhydride and sodium acetate (860 mg, 10 mmol). The mixture was heated at 80° C. for 2 hours. After cooling the reaction mixture was evaporated to dryness. (40 mL) of methanol was added followed by concentrating under vacuum to give 6-bromo-3-methylbenzofuran (600 mg, 75%) as yellow oil. $^1$H NMR (300 MHz, CD$_3$OD) δ 7.62 (s, 1H), 7.38-7.36 (m, 3H), 2.23 (s, 3H).

Methyl 3-(2-amino-5-bromophenylamino)-2-methylpropanoate

To a reversible vial was added 6-bromo-3-methylbenzofuran (600 mg, 2.88 mmol) in methanol (16 mL) was added triethylamine (900 mg, 9 mmol), palladium acetate (116 mg, 0.5 mmol) and 1,3-bis(diphenylphosphino) propane (480 mg, 1 mmol). Then the reaction mixture was charged with carbon monoxide under 15 atm at 110° C. for 12 hours. The suspension was concentrated in vacuum and the residue was purified by column chromatography (silica gel, petroleum ether/ethyl acetate=10:1) to give the product methyl 3-methylbenzofuran-6-carboxylate (0.40 g, 72%) as colorless oil. $^1$H NMR (300 MHz, CDCl$_3$) δ 7.77-7.68 (m, 2H), 7.50 (t, J=7.6 Hz, 1H), 7.23-7.16 (m, 2H), 6.91-6.80 (m, 3H) 5.64 (q, J=6.3 Hz, 1H), 3.90 (s, 3H), 1.64 (d, J=6.3 Hz, 3H). LRMS (M+H+) m/z: calcd 227.98. found 227.

Methyl 3-methyl-2,3-dihydrobenzofuran-6-carboxylate

Methyl 3-methylbenzofuran-6-carboxylate (400 mg, 2.1 mmol), palladium on carbon (50 mg, 0.56 mmol), in methanol (10 mL) was charged with hydrogen (0.4 MPa) at room temperature for 12 hours. Then filtered, and the organic layer was concentrated to dryness and the residue was purified by column chromatography (silica gel, petroleum ether/ethyl acetate=10:1) to give the product methyl 3-methyl-2,3-dihydrobenzofuran-6-carboxylate (384 mg, 95%) as white solid. LRMS (M+H$^+$) m/z: calcd 192.21. found 192. $^1$H NMR (300 MHz, CDCl$_3$) δ 7.54-7.51 (m, 1H), 7.27-7.22 (m, 2H), 4.72-4.66 (m, 1H), 4.10-4.06 (m, 1H), 3.56-3.53 (m, 1H), 1.32 (m, 3H).

3-methyl-2,3-dihydrobenzofuran-6-carboxylic acid

To a reversible vial was added methyl 3-methyl-2,3-dihydrobenzofuran-6-carboxylate (384 mg, 2 mmol) in methanol (16 mL) was added triethylamine (900 mg, 9 mmol), palladium acetate (116 mg, 0.5 mmol) and 1,3-bis(diphenylphosphino) propane (480 mg, 1 mmol). Then the reaction mixture was charged with carbonate monoxide under 15 atm at 110° C. for 12 hours. The suspension was concentrated in vacuum and quenched with aqueous 1N hydrochloric acid (5 mL). The residue was taken up with water (50 mL) and extracted with dichloromethane (50 mL). The combined extract was dried over sodium sulphate, evaporated and purified by column chromatography (silica gel, dichloromethane/methanol=20:1) to give the product 3-methyl-2,3-dihydrobenzofuran-6-carboxylic acid (0.28 g, 78%) as colorless oil.

N-((2-hydroxy-4,6-dimethylpyridin-3-yl)methyl)-3-methyl-2,3-dihydrobenzofuran-6-carboxamide (Compound I-19)

A solution of 3-methyl-2,3-dihydrobenzofuran-6-carboxylic acid (100 mg, 0.56 mmol) in dichloromethane (50 mL) was added 2-(7-Aza-1H-benzotriazole-1-yl)-1,1,3,3-tetramethyluronium hexafluorophosphate (35 mg, 0.5 mmol), triethylamine (32 mg, 0.7 mmol), stirred for 30 minutes. Then 3-(aminomethyl)-4,6-dimethylpyridin-2-ol (27 mg, 0.4 mmol) was added and the mixture was stirred at room temperature for 12 hours. The mixture was washed with water (50 mL), dried over sodium sulphate, concentrated. The residue was purified by column chromatography (silica gel, dichloromethane/methanol=20:1) to give the product N-((2- hydroxy-4,6-dimethylpyridin-3-yl)methyl)-3-methyl-2,3-dihydrobenzofuran-6-carboxamide (75 mg, 43%) as white solid. LRMS (M+H$^+$) m/z: calcd 367.23. found 367. HPLC Purity (214 nm): 97%. $^1$H NMR (300 MHz, CDCl$_3$) δ 7.32-7.27 (m, 2H), 7.12-7.11 (m, 1H), 6.10 (s, 1H), 4.72-4.66 (m, 1H), 4.46 (s, 2H), 4.11-4.05 (m, 1H), 3.56-3.53 (m, 1H), 2.35 (s, 3H), 2.24 (s, 3H), 1.31 (d, J=7.2 Hz, 3H).

Example 13

Synthesis of N-((2-hydroxy-4,6-dimethylpyridin-3-yl)methyl)-4-(pentan-2-yl)benzamide (Compound I-13)

This synthesis involved 4 steps.

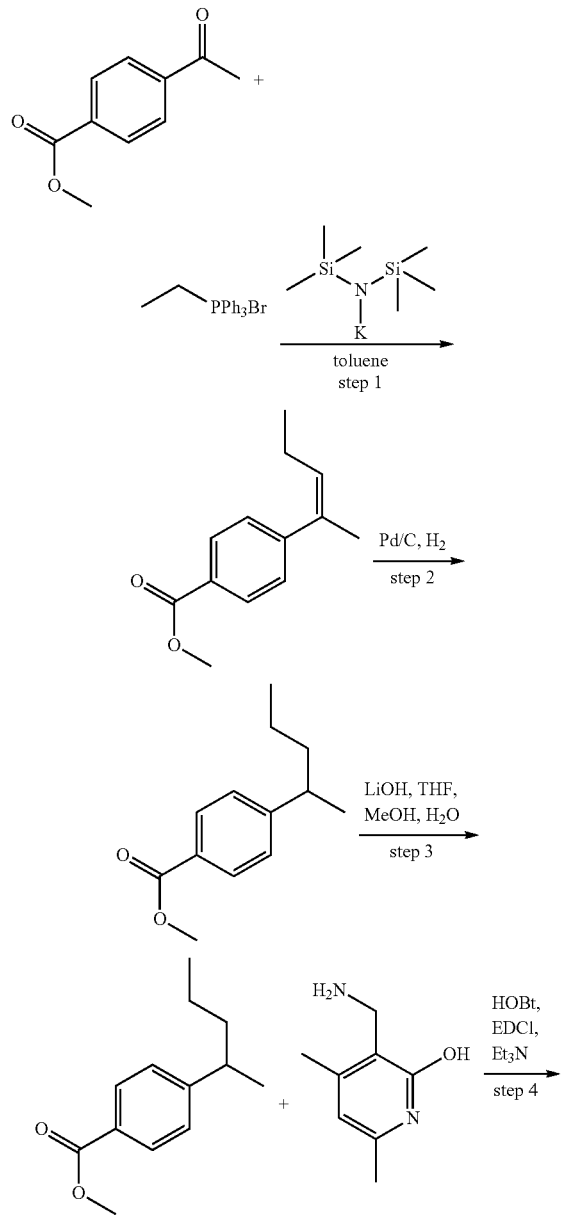

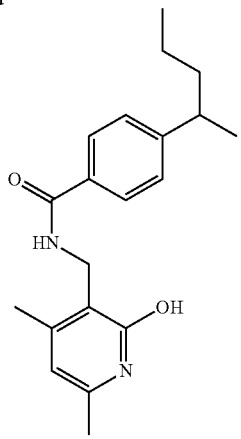

(Z)-methyl 4-(pent-2-en-2-yl)benzoate

Ethyltriphenylphosphonium bromide (4.2 g, 11.2 mmol) was dissolved in tetrahydrofuran (15 mL), and then potassium bis(trimethylsilyl)amide (11.2 mmol, 11.2 mL of a 1M solution in tetrahydrofuran) was added dropwise in the mixture at room temperature under stiffing. After 10 minute, methyl 4-acetylbenzoate (1 g, 5.6 mmol) dissolved in toluene (30 mL) was dropwise and heated to 110° C. for 3 hours. The mixture was cooled and evaporated, the residue was purified by column chromatography (silica gel, petroleum ether/ethyl acetate=5:1) to get (Z)-methyl 4-(pent-2-en-2-yl)benzoate (610 mg, 56%). LRMS (M+H$^+$) m/z: calcd 204.12. found 204.

Methyl 4-(pentan-2-yl)benzoate

To a solution of (Z)-methyl 4-(pent-2-en-2-yl)benzoate (600 mg, 2.15 mmol) in menthol was added Palladium 10% on Carbon (340 mg, 0.3 mmol) and the mixture was hydrogenated at hydrogen gas pressure 4 atmosphere for 8 hours. The reaction mixture was filtered. The filtrate was evaporated and the residue was purified by column chromatography (silica gel, petroleum ether/ethyl acetate=8:1) to get methyl 4-(pentan-2-yl)benzoate (480 mg, 80%). LRMS (M+H$^+$) m/z: calcd 206.13. found 206.

4-(pentan-2-yl)benzoic acid

To a solution of lithium hydroxide (121 mg, 2.9 mmol) in tetrahydrofuran, methanol and water (20 mL, 3:1:1, V/V) was added methyl 4-(pentan-2-yl)benzoate (170 mg, 0.58 mmol). The reaction mixture was stirred at room temperature for 1 hour. The mixture was quench with 10% hydrochloric acid aqueous, extracted with dichloromethane and menthol (20 ml, 10:1), the combine organic layer was dried by anhydrous sodium sulfate, filtered and concentrated to give product 4-(pentan-2-yl)benzoic acid as a white yield (160 mg, 99%).

N-((2-hydroxy-4,6-dimethylpyridin-3-yl)methyl)-4-(pentan-2-yl)benzamide (Compound I-13)

A solution of 4-(pentan-2-yl)benzoic acid (120 mg, 0.66 mmol) in dichloromethane (40 mL) was added N-hydroxybenzotriazole (HOBT) (135 mg, 1.0 mmol), 1-(3-Dimethylaminopropyl)-3-ethylcarbodiimide hydrochloride (EDCI) (192 mg, 1.0 mmol), triethylamine (135 mg, 1.5 mmol), stirred for 30 minute. Then 3-(aminomethyl)-4,6-dimethylpyridin-2-ol (100 mg, 0.66 mmol) was added and the mixture was stirred at room temperature for 18 hours. The mixture was washed with water (30 mL), dried over anhydrous sodium sulfate, concentrated. The residue was purified by column chromatography (silica gel, dichloromethane/methanol=20:1) and the obtained solution was freeze-dried to afford N-((2-hydroxy-4,6-dimethylpyridin-3-yl)methyl)-4-(pentan-2-yl)benzamide (186 mg, 86.4%) as white solid. LRMS (M+H$^+$) m/z: calcd 326.20. found 326. HPLC Purity (214 nm)95%. $^1$H NMR (300 MHz, CD$_3$OD): δ 7.72-7.69 (d, J=11 Hz, 2H) 7.29-7.26 (d, J=8.4 Hz, 2H), 6.102 (s, 1H), 4.48 (s, 2H), 2.69-2.62 (m, 1H), 3.36 (s, 3H), 2.24 (s, 3H), 1.66-1.57 (m, 2H), 1.22-1.25 (d, J=9 Hz, 3H), 0.782-0.832 (t, J=7.5 Hz, 3H).

Example 14

Synthesis of N-((2-hydroxy-4,6-dimethylpyridin-3-yl)methyl)-1-isopropyl-2-oxo-1,2-dihydropyridine-4-carboxamide (Compound I-14)

This synthesis involved 4 steps.

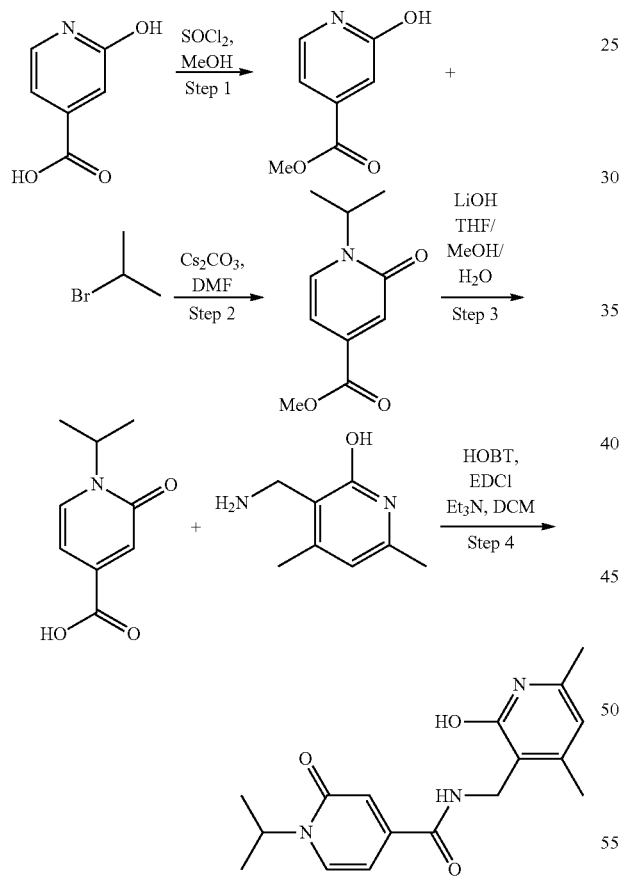

Methyl 2-hydroxyisonicotinate

To a solution of 2-hydroxyisonicotinic acid (1.4 g, 10 mmol) in methanol (100 mL) was added thionyl chloride (5.73 g, 40 mmol) at 0° C., the mixture was stirred overnight. The solvent was evaporated in vacuo and water was added. The mixture was extracted with ethyl acetate (100 mL×3), the organic phase was dried sodium sulfate and evaporated in vacuo to give methyl 2-hydroxyisonicotinate (1.2 g, 78%). LRMS (M+H$^+$) m/z: calcd 153.04. found 153.

Methyl 1-isopropyl-2-oxo-1,2-dihydropyridine-4-carboxylate

To a solution of methyl 2-hydroxyisonicotinate (306 mg, 2 mmol) in dimethyl formamide (30 mL) was added 2-bromopropane (0.24 g, 2 mmol) and potassium carbonate (5.52 g, 4 mmol), the mixture was heated to 110° C. and stirred overnight. The solvent was evaporated in vacuo and purified by column chromatography (silica gel, petroleum ether/ethyl acetate=3:1) to give methyl 1-isopropyl-2-oxo-1,2-dihydropyridine-4-carboxylate (70 mg, 18%). LRMS (M+H$^+$) m/z: calcd 195.05. found 195.

1-isopropyl-2-oxo-1,2-dihydropyridine-4-carboxylic acid

Methyl 1-isopropyl-2-oxo-1,2-dihydropyridine-4-carboxylate (70 mg, 0.36 mmol), lithium hydroxide (57.1 mg, 1.36 mmol), tetrahydrofuran (50 mL), methanol (10 mL) and water (10 mL) was stirred at 20° C. for 4 hours. The mixture was purified by column chromatography (silica gel, petroleum ether/ethyl acetate=2:1) to give 1-isopropyl-2-oxo-1,2-dihydropyridine-4-carboxylic acid (50 mg, 72%) as a white solid. LRMS (M+H$^+$) m/z: calcd 181.07. found 181.

N-((2-hydroxy-4,6-dimethylpyridin-3-yl)methyl)-1-isopropyl-2-oxo-1,2-dihydropyridine-4-carboxamide (Compound I-14)

1-isopropyl-2-oxo-1,2-dihydropyridine-4-carboxylic acid (50 mg, 0.28 mmol), 1-(3-Dimethylaminopropyl)-3-ethylcarbodiimide hydrochloride (95 mg, 0.5 mmol), 1-Hydroxybenzotriazole (67 mg, 0.5 mmol), triethylamine (0.1 mL) in dichloromethane (5 mL) were stirred at 25° C. for 0.5 hour. Then 3-(aminomethyl)-4,6-dimethylpyridin-2-ol (50 mg, 0.33 mmol) was added to the above mixture. The mixture was stirred at 25° C. overnight and purified by column chromatography (silica gel, petroleum ether/ethyl acetate=2:1) to give N-((2-hydroxy-4,6-dimethylpyridin-3-yl)methyl)-1-isopropyl-2-oxo-1,2-dihydropyridine-4-carboxamide (31 mg, 35%) as a white solid. LRMS (M+H+) m/z: 315.16. found 315. HPLC Purity (214 nm): 100%. $^1$H NMR (300 MHz, DMSO): δ 11.48 (d, J=4.2 Hz, 1H), 8.53 (t, J=5.1 Hz, 1H), 7.77 (d, J=7.2 Hz, 1H), 7.74 (d, J=2.1 Hz, 1H), 6.56-6.53 (m, 1H), 5.85 (s, 1H), 5.03-4.98 (m, 1H), 4.24 (d, J=5.1 Hz, 2H), 2.14-2.09 (m, 6H), 1.28-1.22 (m, 6H).

Example 15

Synthesis of 1-sec-butyl-N-((2-hydroxy-4,6-dimethylpyridin-3-yl)methyl)-2-oxo-1,2-dihydropyridine-4-carboxamide (Compound I-30)

This synthesis involved 3 steps.

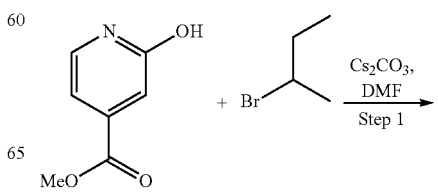

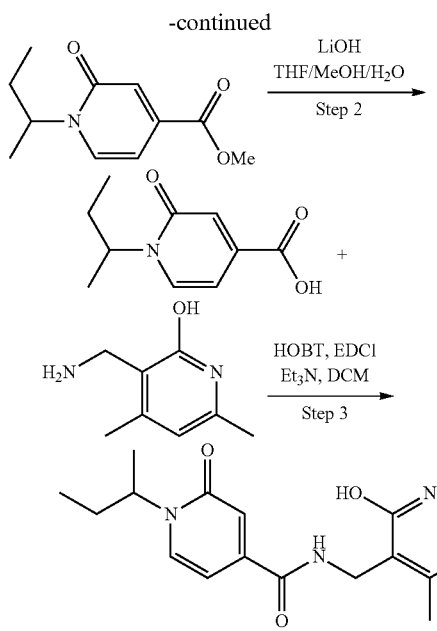

Methyl 1-sec-butyl-2-oxo-1,2-dihydropyridine-4-carboxylate

To a solution of methyl 2-hydroxyisonicotinate (306 mg, 2 mmol) in N,N-dimethylformamide (20 mL) was added 2-bromobutane (330 mg, 2.4 mmol) and cesium carbonate (652 mg, 2 mmol), then stirred at room temperature for 12 hours. The reaction mixture was concentrated in vacuo and the residue was purified by column chromatography with dichloromethane/methanol=40:1 to give methyl 1-sec-butyl-2-oxo-1,2-dihydropyridine-4-carboxylate (334 mg, 80%). LRMS (M+H$^+$) m/z: calcd 209.11. found 209.

1-sec-butyl-2-oxo-1,2-dihydropyridine-4-carboxylic acid

To a solution of methyl 1-sec-butyl-2-oxo-1,2-dihydropyridine-4-carboxylate (209 mg, 1 mmol) in tetrahydrofuran (20 mL) and methanol (7 mL) was added lithium hydroxide (120 mg, 5 mmol) in water (7 mL), then stirred at room temperature for 12 hour, the reaction mixture was concentrated, to the residue was added water (10 mL), acidified with hydrochloric acid to PH=4, collected and dried the solid to give 1-sec-butyl-2-oxo-1,2-dihydropyridine-4-carboxylic acid (98 mg, 50%). LRMS (M+H+) m/z: calcd for 195.09. found 195.

1-sec-butyl-N-((2-hydroxy-4,6-dimethylpyridin-3-yl)methyl)-2-oxo-1,2-dihydropyridine-4-carboxamide (Compound I-30)

To a solution of 1-sec-butyl-2-oxo-1,2-dihydropyridine-4-carboxylic acid (98 mg, 0.5 mmol) in dichloromethane (20 mL) were added 1H-benzo[d][1,2,3]triazol-1-ol (135 mg, 1 mmol), 1-(3-Dimethylaminopropyl)-3-ethylcarbodiimide hydrochloride (190 mg, 1 mmol) and triethylamine (253 mg, 2.5 mmol), and stirred at room temperature for 0.5 hour, 3-(aminomethyl)-4,6-dimethylpyridin-2-ol (152 mg, 1 mmol) was added and stirred for 4 hours. To the reaction mixture was added water (20 mL), extracted with dichloromethane (20 mL) two times, combined and concentrated the organic layers, the residue was purified by chromatography with petroleum/ethyl acetate=1:1 to afford 1-sec-butyl-N-((2-hydroxy-4,6-dimethylpyridin-3-yl)methyl)-2-oxo-1, 2-dihydropyridine-4-carboxamide (132 mg, 80% yield). LRMS (M+H+) m/z: calcd for 329.17. found 329. HPLC Purity (214 nm): 99%. $^1$H NMR (300 MHz, d$^6$-DMSO): δ 11.48 (s, 1H), 8.54 (d, J=4.8 Hz, 1H), 7.71 (d, J=7.2 Hz, 1H), 6.84 (s, 1H), 6.53 (dd, J=1.8 and 7.2 Hz, 1H), 5.86 (s, 1H), 4.87-4.79 (m, 1H), 4.23 (d, J=4.8 Hz, 2H), 2.14 (s, 3H), 2.08 (s, 3H), 1.71-1.61 (m, 2H), 1.25 (d, J=6.9 Hz, 6H), 0.72 (t, J=7.2 Hz, 3H).

Example 16

Synthesis of 4-(1-acetamidoethyl)-N-((2-hydroxy-4,6-dimethylpyridin-3-yl)methyl)benzamide (Compound I-29)

This synthesis involved 4 steps.

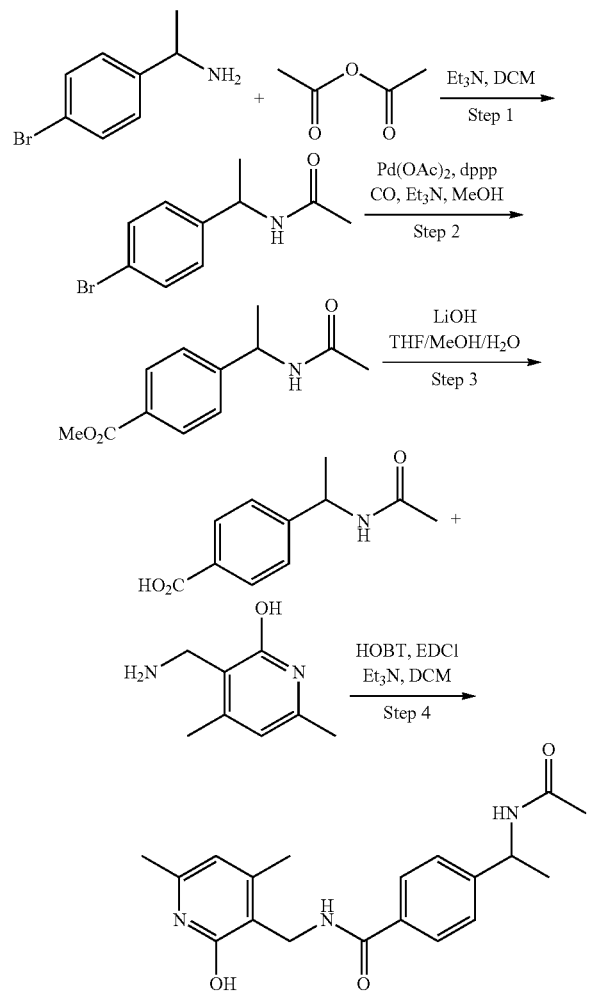

N-(1-(4-bromophenyl)ethyl)acetamide

Triethylamine (2.8 mL) was dropped to the solution of 1-(4-bromophenyl)ethanamine (2.0 g, 10.0 mmol), and acetic anhydride (1.53 g, 15.0 mmol) in dichloromethane (30 mL) at room temperature. Then the mixture was stirred at room temperature for 12 hours. The mixture was washed with sodium hydroxide solution (40 mL, 0.5M) and water (40 mL). The organic phase was dried over sodium sulfate and filtered. The filtrate was concentrated to give a residue. The residue was purified by column chromatography (silica gel, petroleum ether/ethyl acetate=1:5) to give N-(1-(4-bromophenyl)

ethyl)acetamide (2.2 g, 91%) as a white solid. $^1$H NMR (300 MHz, d$^6$-DMSO): δ 8.27 (d, J=4.8 Hz, 1H), 7.38 (d, J=8.4 Hz, 2H), 7.01 (d, J=8.4 Hz, 1H), 4.94 (m, 1H), 2.12 (s, 3H), 1.45 (d, J=6.6 Hz, 3H).

Methyl 4-(1-acetamidoethyl)benzoate

A mixture of N-(1-(4-bromophenyl)ethyl)acetamide (2.2 g, 9.1 mmol), palladium acetate (612 mg, 2.7 mmol), 1,3-bis(diphenylphosphino)propane (1.12 g, 2.7 mmol), triethylamine (6.3 mL), methanol (30 mL) was stirred at 100° C. under carbon monoxide (20 atms) for 12 hours. The mixture was concentrated to give a residue. The residue was purified by column chromatography (silica gel, petroleum ether/ethyl acetate=5:1) to give methyl 4-(1-acetamidoethyl)benzoate (2.0 g, 100%). $^1$H NMR (300 MHz, d$^6$-DMSO): δ 8.27 (d, J=4.8 Hz, 1H), 7.38 (d, J=8.4 Hz, 2H), 7.01 (d, J=8.4 Hz, 1H), 4.94 (m, 1H), 3.89 (s, 3H), 2.12 (s, 3H), 1.45 (d, J=6.6 Hz, 3H).

4-(1-acetamidoethyl)benzoic acid

A mixture of methyl 4-(1-acetamidoethyl)benzoate (2.0 g, 9.0 mmol), lithium hydroxide monohydrate (2.0 g, 48.3 mmol), water (20 mL) and methanol (20 mL) in tetrahydrofuran (60 mL) was stirred at 20° C. for 12 hours. The reaction mixture was concentrated. The residue was acidified to pH=2 with concentrated hydrochloride solution. The mixture was extracted with ethyl acetate (20 mL×2). The organic phase was dried over sodium sulfate and filtered. The filtrate was concentrated. The residue was purified by column chromatography (silica gel, petroleum ether/ethyl acetate=2:1) to give 4-(1-acetamidoethyl)benzoic acid as a white solid (1.5 g, 80%). LRMS (M+H$^+$) m/z: calcd 207.09. found 207.

1-(aminomethyl)cyclopropanecarboxamide (Compound I-29)

To a solution of 4-(1-acetamidoethyl)benzoic acid (414 mg, 2.0 mmol), 1-hydroxybenzotriozole (405 mg, 3.0 mmol), 1-(3-Dimethylaminopropyl)-3-ethylcarbodiimide hydrochloride (576 mg, 3.0 mmol), triethylamine (0.83 mL) in dichloromethane (30 mL) was added 3-(aminomethyl)-4,6-dimethylpyridin-2-ol (82 mg, 0.54 mmol). The reaction mixture was stirred at 20° C. for 13 hours. The mixture was washed with water (20 mL×2). The organic phase was dried over sodium sulfate and filtered. The filtrate was concentrated. The residue was purified by column chromatography (silica gel, dichloromethane/methanol=10:1) to give 4-(1-acetamidoethyl)-N-((2-hydroxy-4,6-dimethylpyridin-3-yl)methyl)benzamide as a white solid (250 mg, 37%). LRMS (M+H$^+$) m/z: calcd 341.17. found 341. HPLC Purity (214 nm): 98%. $^1$H NMR (300 MHz, d$^6$-DMSO): δ 11.46 (s, 1H), 8.35-8.26 (m, 2H), 7.76 (d, J=8.4 Hz, 2H), 7.31 (d, J=8.4 Hz, 2H), 5.85 (s, 1H), 4.90 (q, J=7.2 Hz, 1H), 4.28 (d, J=5.1 Hz, 2H), 2.16 (s, 3H), 2.11 (s, 3H), 1.83 (s, 3H), 1.1 (d, J=7.2 Hz, 3H).

Example 17

Synthesis of N-((2-hydroxy-4,6-dimethylpyridin-3-yl)methyl)-4-(4-methoxybutan-2-yl)benzamide (Compound I-25)

This synthesis involved 5 steps.

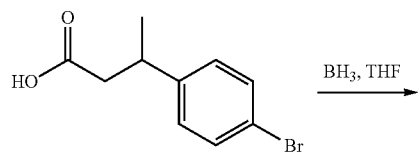

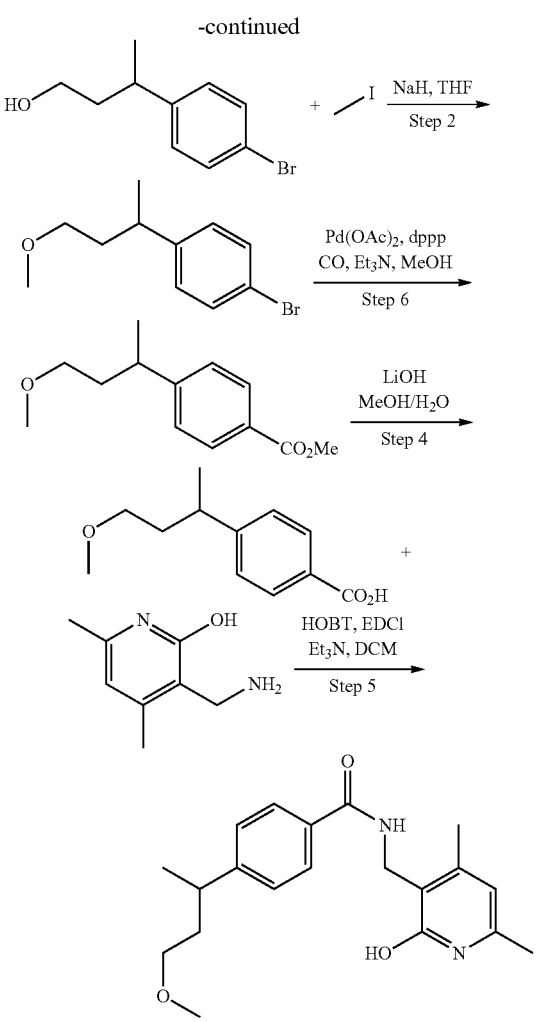

3-(4-bromophenyl)butan-1-ol

To the solution of 3-(4-bromophenyl)butanoic acid (1 g, 4.1 mmol) in tetrahydrofuran (100 mL) was added borane in tetrahydrofuran (8 mL, 1 mol/L), the solution was stirred at reflux for 2 hours, then the solution was concentrated and purified by column chromatography (silica gel, Petroleum ether/ethyl acetate=20:1) to give 3-(4-bromophenyl)butan-1-ol (791 mg, 84.6%).

1-bromo-4-(4-methoxybutan-2-yl)benzene

To the solution of 3-(4-bromophenyl)butan-1-ol (791 mg, 3.47 mmol) in tetrahydrofuran (50 mL) was added sodium hydride (278 mg, 6.94 mmol), the mixture was stirred at room temperature for 30 minutes, then iodomethane (985 mg, 6.94 mmol) was added, the mixture was stirred for 5 hours, then quenched with water (1 mL) concentrated and purified by column chromatography (silica gel, dichloromethane/methanol=20:1) to give 1-bromo-4-(4-methoxybutan-2-yl)benzene (541 mg, 64%).

Methyl 4-(4-methoxybutan-2-yl)benzoate

To the solution of 1-bromo-4-(4-methoxybutan-2-yl)benzene (541 mg, 2.2 mol) in methanol (30 mL) was added 1,3-bis(diphenylphosphino) propane (182 mg, 0.4 mol), Palladium acetate (99 mg, 0.44 mmol), and triethylamine (1.1 g, mol) the mixture was stirred at 90° C. for 12 hours under an atmosphere of carbon monoxide in sealed tube. Then the mixture was concentrated and purified by column chromatography (silica gel, Petroleum ether/ethyl acetate=20:1) to give methyl 4-(4-methoxybutan-2-yl)benzoate (211.8 mg, 43%).

4-(4-methoxybutan-2-yl)benzoic acid

To the solution of methyl 4-(4-methoxybutan-2-yl)benzoate (211 mg, 0.95 mmol) in methanol (30 mL) and water (5 mL) was added lithium hydroxide hydrate (100 mg, 2.4 mmol) were added. The mixture was stirred at room temperature for 12 hours. Then the reaction mixture was acidified by hydrochloric acid aqueous solution (1N) to adjust pH=6 and extracted with dichloromethane (10 mL×3). The organic layers were combined and concentrated to give 4-(4-methoxybutan-2-yl)benzoic acid (177 mg, 90%).

N-((2-hydroxy-4,6-dimethylpyridin-3-yl)methyl)-4-(4-hydroxybutan-2-yl)benzamide (Compound I-25)

A mixture of 4-(4-methoxybutan-2-yl)benzoic acid (177 mg, 0.85 mmol), 1-ethyl-3-(3-dimethyllaminopropyl)carbodiimide hydrochloride (245 mg, 1.3 mmol), N-hydroxybenzotriazole (176 mg, 1.3 mmol) and triethylamine (258 mg, 2.55 mmol) in dichloromethane (50 mL) was stirred for 30 minutes at room temperature. Then to the mixture, 3-(aminomethyl)-4,6-dimethylpyridin-2-ol (130 mg, 0.85 mmol) was added. The resultant mixture was stirred at room temperature for 12 hours. Then the mixture was washed with water (30 mL×3). The organic layer was concentrated to give a residue and the residue was purified by column chromatography (silica gel, dichloromethane/methanol=20:1) to give N-((2-hydroxy-4,6-dimethylpyridin-3-yl)methyl)-4-(4-hydroxybutan-2-yl)benzamide (47 mg, 17%). LRMS (M+H$^+$) m/z: calcd 324.19 found 324. $^1$H. NMR (300 MHz, CD$_3$OD): δ 12.96 (s, 1H), 7.80 (s, 1H), 7.70 (d, J=7.8 Hz, 2H), 7.24 (d, J=7.8 Hz, 2H), 5.95 (s, 1H), 4.56 (d, J=5.7 Hz, 2H), 3.20-3.14 (m, 5H), 2.93 (q, J=7.2 Hz, 1H), 2.37 (s, 3H), 2.27 (s, 3H), 1.82 (q, J=6.9 Hz, 2H), 1.23 (d, J=6.9 Hz, 3H).

Example 18

Synthesis of 4-(4-acetamidobutan-2-yl)-N-((2-hydroxy-4,6-dimethylpyridin-3-yl)methyl)benzamide (Compound I-23)

This synthesis involved 5 steps.

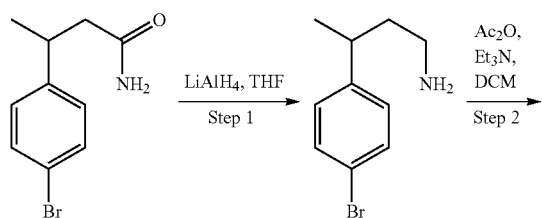

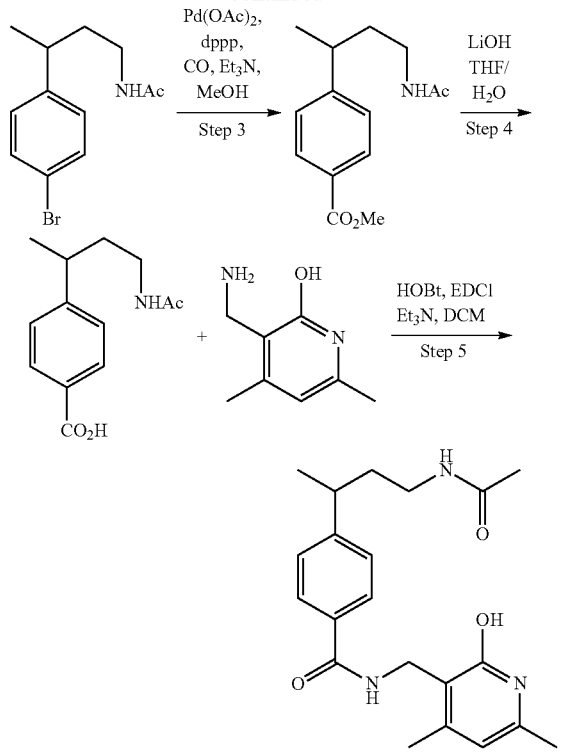

3-(4-bromophenyl)butan-1-amine

To a solution of 3-(4-bromophenyl)butanamide (0.60 g, 2.48 mmol) in anhydrous tetrahydrofuran (15 mL) was added Lithium aluminum hydride (0.14 g, 37.2 mmol), the mixture was stirred at reflux for 1.5 hours, after the completion of the reaction, the mixture was cooled to 0° C., 1N sodium hydroxide solution (10 mL) was added slowly, after the reaction, the mixture was stirred at room temperature for 15 minutes. The mixture was filtered and the filtration was collected and extracted with ethyl acetate (10 mL×3), the organic phase was collected and dried over sodium sulfate, removed the solvent under reduce pressure to give 3-(4-bromophenyl)butan-1-amine as a pale yellow oil (0.57 g, 100%) which could be used in the next step without further purification. LR S (M+H$^+$) m/z: calcd for 228.13. found 228.

N-(3-(4-bromophenyl)butyl)acetamide

At 0° C., acetic anhydride (0.59 g, 5.75 mmol) was added dropwise into a mixture of 3-(4-bromophenyl)butan-1-amine (0.57 g, 2.5 mmol), triethylamine (1.16 g, 11.5 mmol) and 4-dimethylamino-pyridine (1.0 mg, 0.008 mmol) in anhydrous dichloromethane (10 mL) the mixture was stirred at room temperature for 1.5 hours, water (20 mL) was added and extracted with dichloromethane (10 mL×3), combined and concentrated the organic layers, the residue was purified by column chromatography (silica gel, dichloromethane/Methanol=50:1) to give N-(3-(4-bromophenyl)butyl)acetamide (0.66 g, 94.4%). LRMS (M+H$^+$) m/z: calcd for 270.17. found 270.1.

Methyl 4-(4-acetamidobutan-2-yl)benzoate

To a solution of N-(3-(4-bromophenyl)butyl)acetamide (0.66 g, 2.44 mmol) in anhydrous methanol (30 mL) was added 1,3-Bis(diphenylphosphino)propane (0.31 g, 0.73 mmol), Palladium(II) acetate (0.11 g, 0.49 mmol) and triethylamine (1.23 g, 12.2 mmol) and the mixture was stirred at 100° C. overnight under a carbon monoxide atmosphere of 20 atmospheric pressure, after the completion of the reaction, the mixture was cooled to room temperature and the solvent was removed under reduced pressure, the residue was purified by column chromatography (silica gel, dichloromethane/Methanol=50:1) to give methyl 4-(4-acetamidobutan-2-yl)benzoate (0.23 g, 38%). LRMS (M+H$^+$) m/z: calcd for 249.31. found 249.

4-(4-acetamidobutan-2-yl)benzoic acid

Methyl 4-(4-acetamidobutan-2-yl)benzoate (0.23 g, 0.9 mmol) was dissolved in a mixture of in tetrahydrofuran (10 mL) and water (50 mL), then stirred at 45° C. for 12 hours, after the completion of the reaction, the organic phase was removed under reduced pressure, to the residue was added 1 N hydrochloride to adjust the pH 3-4, then the mixture was extracted with ethyl acetate (10 mL×3), collected the organic phase and dried over Sodium sulfate anhydrous, removed the solvent to afford 4-(4-acetamidobutan-2-yl)benzoic acid (0.21 g, 100%) as a pale yellow oil and directly used in next step. LRMS (M+H$^+$) m/z: calcd for 235.28. found 235.

4-(4-acetamidobutan-2-yl)-N-((2-hydroxy-4,6-dimethylpyridin-3-yl)methyl)benzamide (Compound I-23)

To a solution of 4-(4-acetamidobutan-2-yl)benzoic acid 4-(4-acetamidobutan-2-yl)benzoic acid (0.25 g, 1.06 mmol) in anhydrous dichloromethane (10 mL) was added 1H-benzo[d][1,2,3]triazol-1-ol (0.16 g, 1.17 mmol), 1-ethyl-3-(3-dimethyllaminopropyl)carbodiimide hydrochloride (0.31 g, 1.6 mmol) and triethylamine (0.22 g, 2.12 mmol) and stirred at room temperature for 0.5 hours, 3-(aminomethyl)-4,6-dimethylpyridin-2-ol (0.18 g, 1.17 mmol) was added and stirred at room temperature for 3 hours. To the reaction mixture was added water (20 mL), extracted with dichloromethane (10 mL×3), combined and concentrated the organic layers, the residue was purified by column chromatography (silica gel, dichloromethane/Methanol=30:1) to give 4-(4-acetamidobutan-2-yl)-N-((2-hydroxy-4,6-dimethylpyridin-3-yl)methyl)benzamide (8.2 mg, 2.1%). LRMS (M+H$^+$) m/z: calcd for 369.46. found 369. $^1$H NMR (300 MHz, CD$_3$OD) δ 7.72 (d, J=8.3 Hz, 2H), 7.28 (d, J=8.2 Hz, 2H), 6.08 (d, J=9.4 Hz, 1H), 4.48 (s, 2H), 3.04 (td, J=7.0, 3.0 Hz, 2H), 2.82 (dd, J=14.0, 7.1 Hz, 1H), 2.36 (s, 3H), 2.24 (s, 3H), 1.89 (d, J=11.1 Hz, 3H), 1.79 (dd, J=14.6, 7.3 Hz, 2H), 1.26 (d, J=6.9 Hz, 3H).

Example 19

Synthesis of N-((2-hydroxy-4,6-dimethylpyridin-3-yl)methyl)-4-(4-hydroxybutan-2-yl)benzamide (Compound I-24)

This synthesis involved 5 steps.

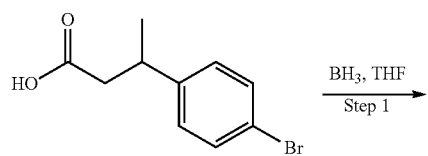

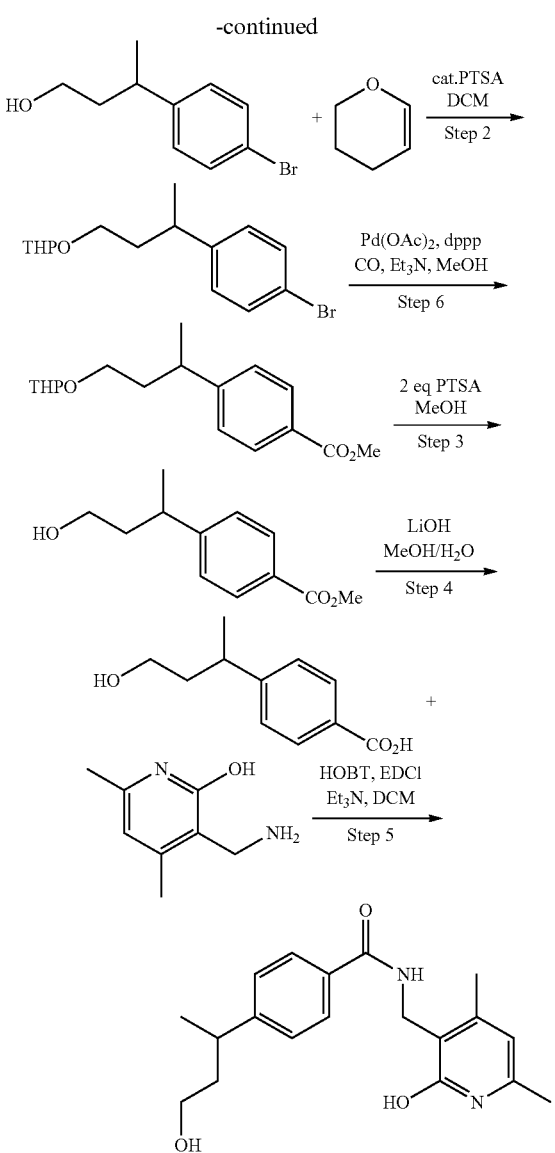

3-(4-bromophenyl)butan-1-ol

To the solution of 3-(4-bromophenyl)butanoic acid (1 g, 4.1 mmol) in tetrahydrofuran (100 ml) was added borane in tetrahydrofuran (8 ml, 1 mol/L), the solution was stirred at reflux for 2 hours, then the solution was concentrated and purified by column chromatography (silica gel, Petroleum ether/ethyl acetate=20:1) to give 3-(4-bromophenyl)butan-1-ol (791 mg, 84.6%).

2-(3-(4-bromophenyl)butoxy)-tetrahydro-2H-pyran

To the solution of 3-(4-bromophenyl)butan-1-ol (791 mg, 3.47 mmol) in dichloromethane (50 mL) was added 3,4-dihydro-2H-pyran (437 mg, 5.2 mmol) and p-toluenesulfonic acid (60 mg, 0.347 m mol), the solution was stirred for 12 hours at room temperature, then the solution was washed with water and dried with sodium sulfate, concentrated to give 2-(3-(4-bromophenyl)butoxy)-tetrahydro-2H-pyran (1.05 g, 97%).

Methyl 4-(4-(tetrahydro-2H-pyran-2-yloxy)butan-2-yl)benzoate

To the solution of 2-(3-(4-bromophenyl)butoxy)-tetrahydro-2H-pyran (1.05 mg, 3.37 mmol) in methanol (30 mL) was added 1,3-bis(diphenylphosphino) propane (278 mg, 0.67 mmol), palladium acetate (151 mg, 0.67 mmol), and triethylamine (1.7 g, 16.9 mmol), the mixture was stirred at 90° C. for 12 hours under an atmosphere of carbon monoxide in sealed tube. Then the mixture was concentrated and purified by column chromatography (silica gel, Petroleum ether/ethyl acetate=20:1) to give methyl 4-(4-(tetrahydro-2H-pyran-2-yloxy)butan-2-yl)benzoate (501.8 mg, 51%).

Methyl 4-(4-hydroxybutan-2-yl)benzoate

To the solution of methyl 4-(4-(tetrahydro-2H-pyran-2-yloxy)butan-2-yl)benzoate (501.8 mg 1.72 mmol) in methanol (60 mL) was added p-toluenesulfonic acid (592 mg, 3.44 mmol). the solution was stirred for 12 hours, then the solvent was remove and dissolved in dichloromethane (50 ml) and washed water, dried with sodium sulfate, concentrated to give methyl 4-(4-hydroxybutan-2-yl)benzoate (354 mg, 99%).

4-(4-hydroxybutan-2-yl)benzoic acid

To the solution of methyl 4-(4-hydroxybutan-2-yl)benzoate (354 mg, 1.7 mmol) in methanol (30 mL) and water (5 mL) was added lithium hydroxide hydrate (150 mg, 3.6 mmol) were added. The mixture was stirred at room temperature for 12 hours. Then the reaction mixture was acidified by hydrochloric acid aqueous solution (1N) to adjust pH=6 and extracted with dichloromethane (10 mL×3). The organic layers were combined and concentrated to give 4-(4-hydroxybutan-2-yl)benzoic acid (290 mg, 88%).

N-((2-hydroxy-4,6-dimethylpyridin-3-yl)methyl)-4-(4-hydroxybutan-2-yl)benzamide A mixture of 4-(4-hydroxybutan-2-yl)benzoic acid (290 mg, 1.5 mmol), 1-ethyl-3-(3-dimethyllaminopropyl)carbodiimide hydrochloride (432 mg, 2.25 mmol), N-hydroxybenzotriazole (3.4 mg, 2.25 mmol) and triethylamine (455 mg, 4.5 mmol) in dichloromethane (50 mL) was stirred for 30 minutes at room temperature. Then to the mixture, 3-(aminomethyl)-4,6-dimethylpyridin-2-ol (228 mg, 1.5 mmol) was added. The resultant mixture was stirred at room temperature for 12 hours. Then the mixture was washed with water (30 mL×3). The organic layer was concentrated to give a residue and the residue was purified by column chromatography (silica gel, dichloro methane/methanol=20:1) to give N-((2-hydroxy-4,6-dimethylpyridin-3-yl)methyl)-4-(4-hydroxybutan-2-yl)benzamide (41 mg, 8.3%). LRMS (M+H$^+$) m/z: calcd 328.18 found 328; $^1$H. NMR (300 MHz, CD3OD): δ 7.73 (d, J=8.1 Hz, 2H), 7.30 (d, J=8.1 Hz, 2H), 6.11 (s, 1H), 4.49 (s, 2H), 3.44-3.42 (m, 2H), 2.94 (q, J=7.2 Hz, 1H), 2.36 (s, 3H), 2.42 (s, 3H), 1.82 (q, J=6.9 Hz, 2H), 1.26 (d, J=6.9 Hz, 3H).

Example 20

IC$_{50}$ Measurements for Inhibitors Using EZH2

EZH2 Assay:

Assays were carried out by mixing rPRC2 together with biotinylated oligonucleosome substrates in the presence of the radio-labeled enzyme co-factor, S-adenosyl-L-methionine ($^3$H SAM) (Perkin Elmer) and monitoring the enzymatically mediated transfer of tritiated methyl groups from $^3$H SAM to histone lysine residues. The amount of resulting tritiated methylhistone product was measured by first capturing the biotinylated oligonucleosomes in streptavidin (SAV) coated FlashPlates (Perkin Elmer), followed by a wash step to remove un-reacted $^3$H SAM, and then counting on a Top-Count NXT 384 well plate scintillation counter (Perkin Elmer). The final assay conditions for EZH2 were as follows: 50 mM Tris Buffer pH 8.5, 1 mM DTT, 69 µM Brij-35 detergent, 5.0 mM MgCl$_2$, 0.1 mg/mL BSA, 0.2 µM $^3$H SAM, 0.2 µM biotinylated oligonucleosomes, 3.6 µM H3K27me3 peptide and 2 nM EZH2.

Compound IC$_{50}$ measurements were obtained as follows: Compounds were first dissolved in 100% DMSO as 10 mM stock solutions. Ten point dose response curves were generated by dispensing varying amounts of the 10 mM compound solution in 10 wells of the 384 well plate (Echo; Labcyte), pure DMSO was then used to backfill the wells to insure all wells have the same amount of DMSO. A 12.5 µL volume of the HMT enzyme, H3K27me3 peptide and oligonucleosome substrate in assay buffer was added to each well of the assay plate using a Multidrop Combi (ThermoFisher). Compounds were pre-incubated with the enzyme for 20 min, followed by initiation of the methyltransferase reaction by addition of 12.5 µL of 3H SAM in assay buffer (final volume=25 µL). The final concentrations of compounds ranged from a top default concentration of 80 µM down to 0.16 µM in ten 2-fold dilution steps. Reactions were carried out for 60 minutes and quenched with 20 µL per well of 1.96 mM SAH, 50 mM Tris PH 8.5, 200 mM EDTA. Stopped reactions were transferred to SAV coated Flashplates (Perkin Elmer), incubated for 120 min, washed with a plate washer, and then read on the Top-Count NXT (1.0 min/well) to measure the amount of methylhistone product formed during the reaction. The amount of methylhistone product was compared with the amount of product formed in the 0% and 100% inhibition control wells allowing the calculation of % Inhibition in the presence of the individual compounds at various concentrations. IC$_{50}$'s were computed using a 4 parameter fit non-linear curve fitting software package (XLFIT, part of the database package, ActivityBase (IDBS)) where the four parameters were IC$_{50}$, Hill slope, pre-transitional baseline (0% INH), and post-transitional baseline (100% INH); with the latter two parameters being fixed to zero and 100%, respectively, by default.

Assay for Y641N EZH2 was performed as above using reconstituted H3K27Me2 oligonucleosomes as substrate.

Table 2 shows the activity of selected compounds of this invention in the EZH2 and Y641N EZH2 activity inhibition assay. IC$_{50}$ values are reported as follows: "A" indicates an IC$_{50}$ value of less than 1 µM; "B" indicates an IC$_{50}$ value of 1 µM to 10 µM; and "C" indicates an IC$_{50}$ value of greater than 10 µM for each enzyme; "*" indicates that no inhibition was observed at the highest concentration of compound tested.

TABLE 2

IC50 Values for Compounds of Formula I against EZH2 and Y641N EZH2 Mutant Enzymes.

| Compound No. | EZH2 IC50 | Y641N EZH2 IC50 |
| --- | --- | --- |
| I-1 | B | B |
| I-2 | A | B |
| I-3 | B | C |
| I-4 | A | B |
| I-5 | A | B |
| I-6 | C | C |

TABLE 2-continued

IC50 Values for Compounds of Formula I against
EZH2 and Y641N EZH2 Mutant Enzymes.

| Compound No. | EZH2 IC50 | Y641N EZH2 IC50 |
|---|---|---|
| I-7 | A | B |
| I-8 | A | B |
| I-9 | A | B |
| I-10 | A | B |
| I-11 | B | * |
| I-12 | B | * |
| I-13 | A | A |
| I-14 | B | * |
| I-20 | C | * |
| I-29 | * | * |
| I-30 | * | * |

We claim:

1. A compound having structural formula I-i:

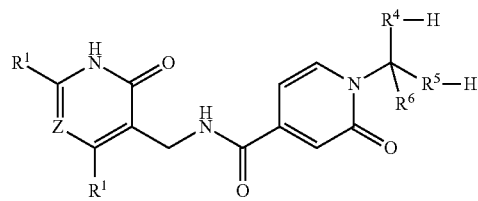

I-i or a pharmaceutically acceptable salt thereof, wherein:
Z is =CH;
each $R^1$ is $CH_3$;
—$R^4$—H is —$CH_3$;
—$R^5$—H is selected from —$CH_3$, —$CH(CH_3)_2$, —$(CH_2)_2CH_3$, and —$CH_2CH_3$; and
$R^6$ is hydrogen.

2. A pharmaceutically acceptable composition comprising:
a) the compound of claim 1 or a pharmaceutically acceptable salt thereof; and
b) a pharmaceutically acceptable carrier.

3. The compound of claim 1, wherein the compound is

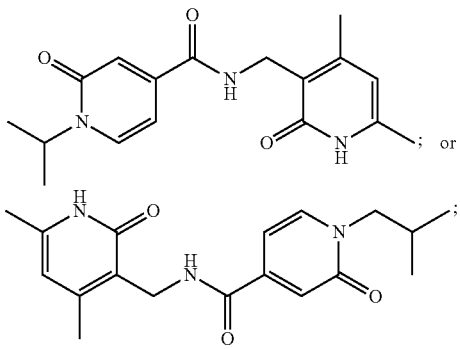

or a pharmaceutically acceptable salt thereof.

* * * * *